(12) United States Patent
Ji et al.

(10) Patent No.: US 8,486,979 B2
(45) Date of Patent: Jul. 16, 2013

(54) 1,2,4 OXADIAZOLE COMPOUNDS AND METHODS OF USE THEREOF

(75) Inventors: Jianguo Ji, Libertyville, IL (US); Chih-Hung Lee, Vernon Hills, IL (US); Kevin B. Sippy, Antioch, IL (US); Tao Li, Grayslake, IL (US); Murali Gopalakrishnan, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 1142 days.

(21) Appl. No.: 12/134,678

(22) Filed: Jun. 6, 2008

(65) Prior Publication Data
US 2008/0269236 A1    Oct. 30, 2008

Related U.S. Application Data

(63) Continuation-in-part of application No. 11/953,625, filed on Dec. 10, 2007.

(60) Provisional application No. 60/999,761, filed on Apr. 12, 2007, provisional application No. 60/874,609, filed on Dec. 12, 2006.

(51) Int. Cl.
| | |
|---|---|
| *A01N 43/82* | (2006.01) |
| *A01N 43/40* | (2006.01) |
| *A61K 31/41* | (2006.01) |
| *A61K 31/50* | (2006.01) |
| *A61K 31/501* | (2006.01) |
| *A61K 31/44* | (2006.01) |
| *C07D 471/04* | (2006.01) |
| *C07D 471/22* | (2006.01) |
| *C07D 487/04* | (2006.01) |
| *C07D 413/04* | (2006.01) |
| *C07D 413/14* | (2006.01) |
| *C07D 413/00* | (2006.01) |
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 417/00* | (2006.01) |
| *C07D 419/00* | (2006.01) |
| *C07D 421/00* | (2006.01) |

(52) U.S. Cl.
USPC ........... 514/364; 514/252.05; 514/252.06; 514/257; 514/333; 546/269.4; 546/256; 544/138; 544/238

(58) Field of Classification Search
USPC ............ 514/364, 252.05, 252.06, 257, 333; 546/269.4, 256; 544/138, 238
See application file for complete search history.

(56) References Cited

U.S. PATENT DOCUMENTS

| | | |
|---|---|---|
| 3,964,896 A | 6/1976 | Brouwer et al. |
| 4,022,901 A | 5/1977 | Narayanan et al. |
| 4,122,257 A | 10/1978 | Prossel et al. |
| 5,594,023 A | 1/1997 | Wagnon et al. |
| 5,914,328 A | 6/1999 | Lin et al. |
| 5,948,793 A | 9/1999 | Abreo et al. |
| 5,977,144 A | 11/1999 | Meyer et al. |
| 6,090,818 A | 7/2000 | Foulon et al. |
| 6,130,217 A | 10/2000 | Arnold et al. |
| 6,207,863 B1 | 3/2001 | Berrier et al. |
| 6,538,003 B1 | 3/2003 | Galli et al. |
| 6,579,880 B2 | 6/2003 | Weidner-Wells et al. |
| 6,596,732 B2 | 7/2003 | Serradeil-Le-Gal et al. |
| 6,605,610 B1 | 8/2003 | Coe et al. |
| 6,624,164 B2 | 9/2003 | Schoentjes et al. |
| 6,809,105 B2 | 10/2004 | Schrimpf et al. |
| 6,833,370 B1 | 12/2004 | Schrimpf et al. |
| 6,864,277 B2 | 3/2005 | Roux et al. |
| 6,919,359 B2 | 7/2005 | Piotrowski et al. |
| 7,041,685 B2 | 5/2006 | Cai et al. |
| 7,119,086 B2 | 10/2006 | Di et al. |
| 7,902,379 B2 | 3/2011 | Lubisch et al. |
| 8,017,631 B2 | 9/2011 | Dahl et al. |
| 8,350,055 B2 | 1/2013 | Oost et al. |
| 2003/0109545 A1 | 6/2003 | Serradeil-Le-Gal et al. |
| 2003/0114683 A1 | 6/2003 | Roux et al. |
| 2003/0139413 A1 | 7/2003 | Schoentjes et al. |
| 2003/0162767 A1 | 8/2003 | Roux et al. |
| 2004/0063601 A1 | 4/2004 | Denome et al. |
| 2004/0152724 A1 | 8/2004 | Dart et al. |
| 2004/0180878 A1 | 9/2004 | Di et al. |
| 2004/0186107 A1 | 9/2004 | Schrimpf et al. |

(Continued)

FOREIGN PATENT DOCUMENTS

| | | |
|---|---|---|
| CA | 2107348 A1 | 7/1993 |
| DE | 10148598 A1 | 10/2002 |

(Continued)

OTHER PUBLICATIONS

Skoubis et al. Neuroscience, Mar. 2006, vol. 137, pp. 583-591.*

(Continued)

*Primary Examiner* — Samira Jean-Louis
(74) *Attorney, Agent, or Firm* — Lisa V. Mueller; Michael Best & Friedrich LLP

(57) ABSTRACT

The invention relates to 1,2,4 oxadiazole compounds and analogs thereof, represented by formula (II), and compositions and methods of use thereof.

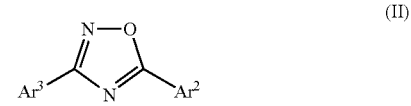

8 Claims, 17 Drawing Sheets

U.S. PATENT DOCUMENTS

| | | | |
|---|---|---|---|
| 2004/0204461 A1* | 10/2004 | Karp et al. ............... 514/364 |
| 2005/0070718 A1 | 3/2005 | Lubisch et al. |
| 2006/0019976 A1 | 1/2006 | Karp et al. |
| 2007/0021465 A1 | 1/2007 | Al-Abed et al. |
| 2007/0021607 A1 | 1/2007 | Lubisch et al. |
| 2007/0185126 A1 | 8/2007 | Lubisch et al. |
| 2008/0167286 A1 | 7/2008 | Gopalakrishnan et al. |
| 2008/0255203 A1 | 10/2008 | Lee et al. |
| 2008/0269236 A1 | 10/2008 | Ji et al. |
| 2008/0318923 A1 | 12/2008 | Sekiguchi et al. |
| 2009/0005397 A1 | 1/2009 | Lubisch et al. |
| 2009/0163492 A1 | 6/2009 | Oost et al. |
| 2009/0215790 A1 | 8/2009 | Lubisch et al. |
| 2010/0305086 A1 | 12/2010 | Gopalakrishnan et al. |
| 2011/0077241 A1 | 3/2011 | Lubisch et al. |
| 2011/0124658 A1 | 5/2011 | Netz et al. |
| 2011/0190314 A1 | 8/2011 | Gopalakrishnan et al. |

FOREIGN PATENT DOCUMENTS

| | | |
|---|---|---|
| EP | 0979814 B1 | 10/2003 |
| EP | 2226074 A2 | 9/2010 |
| EP | 2101763 B1 | 7/2012 |
| EP | 2114921 B1 | 12/2012 |
| EP | 2546250 A1 | 1/2013 |
| EP | 2546251 A1 | 1/2013 |
| EP | 2546252 A1 | 1/2013 |
| WO | 9313083 A1 | 7/1993 |
| WO | 9315051 A1 | 8/1993 |
| WO | 9518105 A1 | 7/1995 |
| WO | 96/40682 | 12/1996 |
| WO | 9825901 A1 | 6/1998 |
| WO | 99/10338 | 3/1999 |
| WO | 99/32480 | 7/1999 |
| WO | 99/65876 | 12/1999 |
| WO | WO0007600 A1 | 2/2000 |
| WO | 00/45799 | 8/2000 |
| WO | 00/71534 | 11/2000 |
| WO | 00/75110 | 12/2000 |
| WO | 01/62736 | 8/2001 |
| WO | 0155130 A2 | 8/2001 |
| WO | 0155134 A2 | 8/2001 |
| WO | 0164668 A2 | 9/2001 |
| WO | 01/81347 | 11/2001 |
| WO | 0181334 A2 | 11/2001 |
| WO | 0187295 A1 | 11/2001 |
| WO | 0198295 A1 | 12/2001 |
| WO | 02068417 A2 | 9/2002 |
| WO | 02/100826 | 12/2002 |
| WO | 03008407 A2 | 1/2003 |
| WO | 2004018607 A2 | 3/2004 |
| WO | 2005030755 A1 | 4/2005 |
| WO | 2006005609 A2 | 1/2006 |
| WO | WO2006047392 A2 | 5/2006 |
| WO | 2006/071184 | 7/2006 |
| WO | 2006080574 A1 | 8/2006 |
| WO | WO2006086068 A1 | 8/2006 |
| WO | 2006/096358 | 9/2006 |
| WO | 2006100081 A2 | 9/2006 |
| WO | 2006100082 A2 | 9/2006 |
| WO | 2006/114400 | 11/2006 |
| WO | 2007149395 A2 | 12/2007 |
| WO | 2008/028903 | 3/2008 |
| WO | 2008073942 | 6/2008 |
| WO | 2008080970 A1 | 7/2008 |
| WO | 2008080971 A1 | 7/2008 |
| WO | 2008080972 A1 | 7/2008 |
| WO | 2008080973 A1 | 7/2008 |
| WO | 2009148452 A1 | 12/2009 |
| WO | 2010138600 A2 | 12/2010 |
| WO | 2010148598 A1 | 12/2010 |

OTHER PUBLICATIONS

Bitner et al., Brain Res. 871:66-74 (2000).
Bundgaard, E., ed., Design of Prodrugs, Elsevier Science Publishers, Amsterdam (1986) Table of Contents.
Chaplan et al., J. Neurosci. Methods 53:55-63 (1994).
Cucchiaro et al., J. Pharmacol. Exp. Ther. 313:389-394 (2005).
Curtis et al., Pharmacology 61:127-135 (2002).
Decker et al., Curr. Top. Med. Chem. 4:369-384 (2004).
Decker et al., Expert Opinion on Investigational Drugs 10:1819-1830 (2001).
Ferreira et al., J. Pharm. Exp. Ther. 294:230-238 (2000).
Furniss et al., Vogel's Textbook of Practical Organic Chemistry, $5^{th}$ Edition (1989) Table of Contents.
Greene, et al., Protective Groups in Organic Synthesis, $3^{rd}$ Edition, John Wiley & Sons, New York (1999) Table of Contents.
Isobe et al., J. Organ. Chem. 64:6989-6992 (1999).
Khan et al., J. Neurocytol. 33:543-556 (2004).
Kim et al., Pain 50:355 (1992).
Lauretti, G.T., Expert Reviews in Neurotherapeutics 6:613-622 (2006).
March Advanced Organic Chemistry, $3^{rd}$ Ed., John Wiley &Sons, New York p. 1157 (1985).
Mark et al., Encyclopedia of Chemical Technology, John Wiley & Sons, New York (1980) Table of Contents.
Marubio et al., Nature 398:805-810 (1999).
Narahashi et al., Biol. Pharm. Bull. 27:1701-1706 (2004).
Pasternack, G.W., Clin. Neuropharmcol. 16:1 (1993).
Rashid, et al., Pain 125:125-135 (2006).
Rueter et al., CNS Drug Rev. 10(2): 167-182 (2004).
Sobol et al., J. Med. Chem. 47:4316-4326 (2004).
Wang et al., Tetrahedron Lett. 47:105-108 (2006).
International Search Report dated Jan. 20, 2009.
Bonte, J.P., et al., "Acyl-6 benzoxazolinones," Eur. J. Med. Chem., 1974, 9, 491-496.
Gopalakrishnan, M. et al., "Ion channels—Ligand gated. Comprehensive Medicinal Chemistry II, Edited by Triggle D.J. et al.,," Major Reference Works, 2006, Unit 2.22, pp. 877-918, Elsevier.
Higuchi T., et al., "Pro-drugs as Novel Delivery Systems," Bioreversible Carriers in Drug Design, 1987, 14, American Pharmaceutical Association and Pergamon Press.
Humphrey et al., "A Novel Synthesis of 3-Bromo-1,2,4-oxadiazoles", J. Heterocyclic Chem, 1989, 26, 23-24.
International Search Report for application No. PCT/US2007/087090, Mailed on Oct. 20, 2008, 6 pages.
IUPAC Commission on Nomenclature of Organic Chemistry: Rules for the Nomenclature of Organic Chemistry Section E: Stereochemistry, Pure Appl Chem, 1976, 45, 11-30.
Lin Yang i, et al., "New Synthesis of 1,2,4-Triazoles and 1,2,4-Oxadiazoles", J. Org. Chem, 1979, 44 (23), 4160-4164.
McClelland Robert A., "Kinetics and Mechanism of Amide Acetal Hydrolysis", Journal of the American Chemical Society, 1978, 100 (6), 1844-1849.
Banker G.S. et al, "Modern Paharmaceutics, 3ed.," 1996, pp. 451 and 596, Marcel Dekker, New York.
Barberis C., et al., "Structural Bases of Vasopressin/oxytocin Receptor Function," Journal of Endocrinology, 1998, vol. 156 (2), pp. 223-239.
Brain C.T., et al., "Novel Procedure for the Synthesis of 1,3,4-oxadiazoles from 1,2-diacylhydrazines Using Polymer-Supported Burgess Reagent Under Microwave Conditions, " Tetrahedron Letters, 1999, vol. 40, pp. 3275-3278.
Bundgaard H., ed., in: Design of Prodrugs, Elsevier Science, 1985, Table of Contents.
Cheung B.S., et al., "Etiologic Significance of Arginine Vasopressin in Motion Sickness," Journal of Clinical Pharmacology, 1994, vol. 34 (6), pp. 664-670.
Co-pending U.S. Appl. No. 61/058,735, filed Jun. 4, 2008.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Dunbar G.C., et al., "Effect of Ispronicline, a Neuronal Nicotinic Acetylcholine Receptor Partial Agonist, in Subjects with Age Associated Memory Impairment (AAMI)," Journal of Psychopharmacology, 2007, vol. 21 (2), pp. 171-178.

Emsley R.A., et al., "Vasopressin Secretion and Memory Impairment in Alcoholic Korsakoff's Syndrome," Alcohol and Alcoholism, 1995, vol. 30 (2), pp. 223-229.

Ersek K., et al., "The Cognitive Effects of Opioids," Pain Management Nursing, 2004, vol. 5 (2), pp. 75-93.

Ettmayer P., et al., "Lessons Learned from Marketed and Investigational Prodrugs," Journal Medicinal Chemistry, 2004, vol. 47 (10), pp. 2393-2404.

European Search Report for Application No. EP10163998, mailed on Jan. 28, 2011, 5 pages.

European Search Report for Application No. EP12177640, mailed on Dec. 12, 2012, 2 pages.

European Search Report for Application No. EP12177642, mailed on Dec. 12, 2012, 2 pages.

European Search Report for Application No. EP12177644, mailed on Dec. 12, 2012, 1 page.

Everts H.G., et al., "Differential Modulation of Lateral Septal Vasopressin Receptor Blockade in Spatial Learning, Social Recognition, and Anxiety-Related Behaviors in Rats," Behavioural Brain Research, 1999, vol. 99 (1), pp. 7-16.

Ex Parte Quayle Action mailed Sep. 11, 2008 for U.S. Appl. No. 10/574,211, filed Jan. 22, 2007.

Ex Parte Quayle Action mailed Aug. 21, 2012 for U.S. Appl. No. 12/839,612, filed Jul. 20, 2010.

Final Office Action mailed Apr. 27, 2012 for U.S. Appl. No. 12/521,713, filed Sep. 7, 2010.

Final Office Action mailed Sep. 27, 2012 for U.S. Appl. No. 13/080,071, filed Apr. 5, 2011.

Final Office Action mailed Sep. 29, 2011 for U.S. Appl. No. 12/787,937, filed May 26, 2010.

Franklin S. R., et al., "Positive Allosteric Modulation of Alpha $ Beta 2 Nicotinic Receptors Potrntiates Some CNS Effects of the Alpha 4 Beta 2 Agonist, ABT-594," Biochemical Pharmacology, 2009, vol. 78 (7), pp. 921.

Grant P.J., et al., "Effects of Physiological Concentrations of Vasopressin on Haemostatic Function in Man," Clinical Science, 1985, vol. 69 (4), pp. 471-476.

Greene T.W., et al., "Protection for the Amino group," Protective Groups in Organic Synthesis, 1999, Third Edition, pp. 494-653.

Griebel G., et al., "Anxiolytic- and Antidepressant-Like Effects of the Non-Peptide Vasopressin V1b Receptor Antagonist, SSR149415, Suggest an Innovative Approach for the Treatment of Stress-Related Disorders," Proceedings of the National Academy of Sciences, 2002, vol. 99 (9), pp. 6370-6375.

Hays R.M., et al., "Vasopressin Antagonists—Progress and Promise," The New England Journal of Medicine, 2006, vol. 355 (20), pp. 2146-2148.

Higuchi T., et al., eds., Pro-drugs as Novels Delivery Systems, vol. 14, ACS Symposium Series, 1975, Table of Contents.

Hulme C., et al., "Quaternary Substituted PDE4 Inhibitors I: the Synthesis and in Vitro Evaluation of a Novel Series of Oxindoles," Bioorganic & Medicinal Chemistry Letters, 1998, vol. 8 (2), pp. 175-178.

International Preliminary Report on Patentability and Written Opinion for Application No. PCT/US08/066002, mailed on Dec. 6, 2010, 8 pages.

International Preliminary Report on Patentability and Written Opinion for Application No. PCT/US2007/087090, mailed on Jun. 16, 2009, 11 pages.

International Preliminary Report on Patentability and Written Opinion for Application No. PCT/US2010/036213, mailed on Nov. 29, 2011, 14 pages.

International Search Report for Application No. PCT/US2007/087091, mailed on May 8, 2008, 3 pages.

International Search Report for Application No. PCT/US2010/036213, mailed on Nov. 24, 2010, 8 pages.

Itoh S., et al., "Attenuated Stress-induced Catecholamine Release in Mice Lacking the Vasopressin V1b Receptor," American Journal of Physiology. Endocrinology and Metabolism, 2006, vol. 291 (1), pp. E147-E151.

Japundzic-Zigon N., et al., "Effects of Nonpeptide and Selective V1 and V2 Antagonists on Blood Pressure Short-Term Variability in Spontaneously Hypertensive Rats," Journal of Pharmacological Sciences, 2004, vol. 95 (1), pp. 47-55.

Jonat S., et al., "Effect of DDAVP on Nocturnal Enuresis in a Patient with Nephrogenic Diabetes Insipidus," Archives of Disease in Childhood, 1999, vol. 81 (1), pp. 57-59.

Khan M.T., et al., "Structure-Activity Relationships of Tyrosinase Inhibitory Combinatorial Library of 2,5-Disubstituted-1,3,4-Oxadiazole Analogues," Bioorganic & Medicinal Chemistry, 2005, vol. 13 (10), pp. 3385-3395.

Kirrane T., et al., "Effects of Amphetamine on Cognitive Impairment in Schizotypal Personality Disorder," Biological Psychiatry, 1996, vol. 39 (7), pp. 581.

Kocevar M., et al., "Ring Transformations of Some 4-Aminopteridine 3-Oxides and Derivatives," Tetrahedron, 1982, vol. 39 (5), pp. 823-829.

Koch Uwe et al., "2-(2-thienyl)-5,6-dihydroxy-4-carboxypyri midines as inhibitors of the hepatitis C virus NS5B polymerase: Discovery, SAR, modeling, and mutagenesis," Journal of Medicinal Chemistry, vol. 49(5), pp. 1693-1705, 2006.

Kocsis J., et al., "Effect of a Vasopressin Antagonist d(CH2)5Tyr(Met)AVP on the Development of Renal Vasospasm Induced by Estrin Plus Vasopressin Administration in Rats," Investigative Radiology, 1987, vol. 22 (12), pp. 973-977.

Kocsis J., et al., "Histochemical and Ultrastructural Study of Renal Cortical Necrosis in Rats Treated with Oestrone + Vasopressin, and its Prevention with a Vasopressin Antagonist," British Journal of Experimental Pathology, 1987, vol. 68 (1), pp. 35-43.

Lee C.R., et al., "Vasopressin: a New Target for the Treatment of Heart Failure," American Heart Journal, 2003, vol. 146 (1), pp. 9-18.

Lynch J.J., et al., "ABT-594 (A Nicotinic Acetylcholine Agonist): Anti-allodynia in a Rat Chemotherapy-induced Pain Model," European Journal of Pharmacology, 2005, vol. 509 (1), pp. 43-48.

March J., "Advanced Organic Chemistry: Reactions, Mechanisms, and Structure" 3rd Edition, John Wilsey & Sons, 1985, Table of Contents.

Mark N.F., et al., "Kirk-Othmer Encyclopedia of Chemical Technology" Second Completely Revised Edition, John Wiley & Sons Inc., 1972, Table of Contents.

Maturi M.F., et al., "Coronary Vasoconstriction Induced by Vasopressin. Production of Myocardial Ischemia in Dogs by Constriction of Nondiseased Small Vessels," Circulation, 1991, vol. 83 (6), pp. 2111-2121.

Non-Final Office Action mailed Aug. 4, 2009 for U.S. Appl. No. 11/440,569, filed May 25, 2006.

Non-Final Office Action mailed Jun. 5, 2009 for U.S. Appl. No. 10/574,211, filed Jan. 22, 2007.

Non-Final Office Action mailed Dec. 9, 2008 for U.S. Appl. No. 11/440,569, filed May 25, 2006.

Non-Final Office Action mailed Dec. 9, 2010 for U.S. Appl. No. 11/953,625, filed Dec. 10, 2007.

Non-Final Office Action mailed Jan. 10, 2012 for U.S. Appl. No. 12/839,612, filed Jul. 20, 2010.

Non-Final Office Action mailed Feb. 11, 2013 for U.S. Appl. No. 13/590,261, filed Aug. 21, 2012.

Non-Final Office Action mailed Apr. 18, 2011 for U.S. Appl. No. 12/787,937, filed May 26, 2010.

Non-Final Office Action mailed Aug. 19, 2011 for U.S. Appl. No. 12/521,713, filed Sep. 7, 2010.

Non-Final Office Action mailed Mar. 19, 2012 for U.S. Appl. No. 13/080,071, filed Apr. 5, 2011.

Non-Final Office Action mailed Jan. 22, 2009 for U.S. Appl. No. 10/574,211, filed Jan. 22, 2007.

Non-Final Office Action mailed Feb. 24, 2012 for U.S. Appl. No. 12/839,595, filed Jul. 20, 2010.

Non-Final Office Action mailed Nov. 30, 2010 for U.S. Appl. No. 10/574,211, filed Jan. 22, 2007.

Notice of Allowance mailed Oct. 1, 2010 for U.S. Appl. No. 11/440,569, filed May 25, 2006.

Notice of Allowance mailed Dec. 2, 2009 for U.S. Appl. No. 10/574,211, filed Jan. 22, 2007.

Notice of Allowance mailed Sep. 4, 2012 for U.S. Appl. No. 12/839,612, filed Jul. 20, 2010.

Notice of Allowance mailed May 5, 2010 for U.S. Appl. No. 10/574,211, filed Jan. 22, 2007.
Notice of Allowance mailed Jan. 10, 2011 for U.S. Appl. No. 10/574,211, filed Jan. 22, 2007.
Notice of Allowance mailed Jul. 10, 2012 for U.S. Appl. No. 12/521,713, filed Sep. 7, 2010.
Notice of Allowance mailed Mar. 12, 2010 for U.S. Appl. No. 11/440,569, filed May 25, 2006.
Notice of Allowance mailed Nov. 13, 2012 for U.S. Appl. No. 12/521,713, filed Sep. 7, 2010.
Notice of Allowance mailed Jun. 24, 2010 for U.S. Appl. No. 11/440,569, filed May 25, 2006.
Notice of Allowance mailed Jun. 26, 2012 for U.S. Appl. No. 12/839,595, filed Jul. 20, 2010.
Office action mailed Dec. 1, 2011 for European Application No. 08770247.8 filed Jun. 6, 2008.
Office action mailed Sep. 10, 2012 for European Application No. 10720520.5 filed May 26, 2010.
Office action mailed Nov. 17, 2011 for European Application No. 10163998.7 filed Dec. 12, 2007.
Office action mailed Jun. 18, 2012 for European Application No. 10163998.7 filed Dec. 12, 2007.
Office action mailed Mar. 29, 2012 for European Application No. 08770247.8 filed Jun. 6, 2008.
Oshikawa S., et al., "Vasopressin Stimulates Insulin Release from Islet Cells through V1b Receptors: a Combined Pharmacological/knockout Approach," Molecular Pharmacology, 2004, vol. 65 (3), pp. 623-629.
Pavo I., et al., "Vasopressin Deficiency Decreases the Frequency of Gastroduodenal Ulceration in Humans," Journal of Physiology, 2000, vol. 94 (1), pp. 63-66.
Poulain R.F., et al., "Parallel Synthesis of 1,2,4-oxadiazoles from carboxylic Acids Using an Improved, Uronium-based Activation," Tetrahedron Letters, 2001, vol. 42 (8), pp. 1495-1498.
Prescott D.M., "Methods in Cell Biology", Academic Press, 1976, Table of Contents.
Qian X., et al., "Syntheses and Insecticidal Activities of Novel 2,5-Disubstituted- 1,3,4-Oxadiazoles," Journal of Chemical Technology and Biotechnology, 1996, vol. 67 (2), pp. 124-130.
Reynaud P. et al., "A New Synthetic Route to 1,3,4-oxadiazoles. Pharmacological Study of Some New Derivatives", Journal of Heterocyclic Chemistry, 1992, vol. 29 (4), pp. 991-993.
Ring R.H., et al., "The Central Vasopressinergic System: Examining the Opportunities for Psychiatric Drug Development," Current Pharmaceutical Design, 2005, vol. 11 (2), pp. 205-225.
Roche E.B., ed., Bioreversible Carries in Drug Design Theory and Application, Pergamon Press, 1987, Table of Contents.
Ryckmans T., et al., "Modulation of the Vasopressin System for the Treatment of CNS Diseases," Current opinion in drug discovery & development, 2010, vol. 13 (5), pp. 538-547.

Scheurer M.A., et al., "Vasopressin to Attenuate Pulmonary Hypertension and Improve Systemic Blood Pressure after Correction of Obstructed Total Anomalous Pulmonary Venous Return," The Journal of Thoracic and Cardiovascular Surgery, 2005, vol. 129 (2), pp. 464-466.
Serradeil-Le Gal C., et al., "Characterization of (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist," Journal of Pharmacology and Experimental Therapeutics, 2002, vol. 300 (3), pp. 1122-1130.
Stella V.J., "Prodrugs as Therapeutics," Expert Opinion on Therapeutic Patents, 2004, vol. 14 (3), pp. 277-280.
Street L.J., et al., "Synthesis and Serotonergic Activity of 5-(Oxadiazolyl)tryptamines: Patent Agonists for 5-HT1D Receptors," Journal of Medicinal Chemistry, 1993, vol. 36 (11), pp. 1529-1538.
Supplementary Partial European Search Report for Application No. 08770247, mailed on Mar. 16, 2012, 4 pages.
Testa B., et al., "Prodrug Research: Futile or Fertile?," Biochemical Pharmacology, 2004, vol. 68, pp. 2097-2106.
Thibonnier M., "Development and Therapeutic Indications of Orally-active Non-peptide Vasopressin Receptor Antagonists," Expert Opinion on Investigational Drugs, 1998, vol. 7 (5), pp. 729-740.
Thibonnier M., et al., "Vasopressin Receptor Antagonists in Heart Failure," Current Opinion in Pharmacology, 2003, vol. 3 (6), pp. 683-687.
U.S. Appl. No. 11/953,590, filed Dec. 10, 2007.
Venkatesh S., et al., "Role of the Development Scientist in Compound Lead Selection and Optimization," Journal of Pharmaceutical Sciences, 2000, vol. 89 (2), pp. 145-154.
Webster M., "Ninth New Collegiate Dictionary" Definition of Prevention, Springfield, Massachusetts, 2000, pp. 933.
Wersinger S.R., et al., "Vasopressin V1b Receptor Knockout Reduces Aggressive Behavior in Male Mice," Molecular Psychiatry, 2002, vol. 7 (9), pp. 975-984.
Wiffen P.J., et al., Gabapentin for Acute and Chronic Pain (Review), Cochrane Database of Systematic Reviews, 2005, vol. 20 (3), pp. 1-23.
Wilens T.E., et al., "ABT-089, A Neuronal Nicotinic Receptor Partial Agonist, for the Treatment of Attention-Deficit/Hyperactivity Disorder in Adults: Results of a Pilot Study," Biological Psychiatry, 2006, vol. 59 (11), pp. 1065-1070.
Wolff, Mandred E., "Burger's Medicinal Chemistry and Drug Discovery," Principles and Practice, 1995, 975-977, 5th Ed, vol. 1, John Wiley & Sons.
Yatagai T., et al., "Close Association of Severe Hyponatremia with Exaggerated Release of Arginine Vasopressin in Elderly Subjects with Secondary Adrenal Insufficiency," European Journal of Endocrinology, 2003, vol. 148 (2), pp. 221-226.

* cited by examiner

1,2,4 OXADIAZOLE COMPOUNDS AND METHODS OF USE THEREOF

CROSS-REFERENCE TO RELATED APPLICATIONS

This application is a continuation-in-part application of U.S. patent application Ser. No. 11/953,625, filed Dec. 10, 2007, which claims priority from U.S. Patent Application Ser. No. 60/999,761, filed Apr. 12, 2007 and U.S. Patent Application 60/874,609, filed Dec. 12, 2006, each of which is herein incorporated by reference in its entirety.

BACKGROUND OF THE INVENTION

1. Technical Field

The invention relates to novel compounds and compositions comprising oxadiazole derivatives, and methods of using the same.

2. Description of Related Technology

The endogenous cholinergic neurotransmitter, acetylcholine (ACh), exerts its biological effect via two types of cholinergic receptors, the muscarinic acetylcholine receptors (mAChR) and the nicotinic acetylcholine receptors (nAChR). nAChRs are pentameric assemblies of subunits surrounding a central pore that gates the flux of $Na^+$, $K^+$ and $Ca^{2+}$ ions. At least 16 subunit proteins, i.e. $\alpha 2$-$\alpha 10$, $\beta 1$-$\beta 10$, $\gamma$, $\delta$ and $\epsilon$, have been identified in neuronal tissues. These subunits provide for a great variety of homomeric and heteromeric combinations that account for the diverse receptor subtypes. For example, functional neuronal nAChR or neuronal nicotinic receptor (NNR) assemblies can be homomeric, comprising $\alpha 7$ or $\alpha 8$ or $\alpha 9$ subunits, or heteromeric, usually with at least one subunit from the $\alpha$ group ($\alpha 2$, $\alpha 3$, $\alpha 4$, $\alpha 6$) and the remainder from the $\beta$ group ($\beta 2$, $\beta 4$). In the central nervous system, $\alpha 4\beta 2$-containing NNR and $\alpha 7$-containing NNR subtypes are the most widespread and mediate synaptic and, possibly, paracrine functions. These NNRs are expressed at high levels in areas involved with learning and memory, and play key roles in modulating neurotransmission in these regions. Reduced cholinergic activity and dysregulation of NNRs have been correlated with disease states involving cognitive deficits, progressive dementia, and epilepsy. Accordingly, these NNRs are implicated in a range of physiological and patho-physiological functions related to cognitive function, learning and memory, reward, motor control, arousal and analgesia (reviewed in Gopalakrishnan, M. et al., Ion channels—Ligand-gated. Comprehensive Medicinal Chemistry II, Edited by Triggle D. J. et al., Major Reference Works, Elsevier. Unit 2.22, pp 877-918, 2006).

Neuronal nicotinic receptors, especially $\alpha 4\beta 2$ neuronal nicotinic acetylcholine receptors (nAChRs) have been targeted for pain and various central nervous system diseases. Antisense knockdown of the $\alpha 4$ subunit was found to decrease the analgesic effect of agonists (Bitner R S, et al., Brain Res. 871:66-74, 2000). Reduced antinociceptive responses to nicotine also is seen in $\alpha 4$ gene knockout animals (Marubio L M, et al., Nature 398:805-810, 1999). Both $\alpha 4$ and $\beta 2$ nAChRs are responsible for mediating nicotinic analgesia at supraspinal responses and spinal sites (Decker, M W, et al, Curr Top Med Chem., 4: 369-384, 2004). Antinociceptive effects through $\alpha 4\beta 2$ nAChRs are generally attributed to stimulation of brainstem monoaminergic transmission, particularly in the raphe (Cucchiaro G, et al., J Pharmacol Exp Ther. 313:389-394, 2005). However, $\alpha 4\beta 2$ stimulation of GABAergic and glycinergic inhibitory transmission in the spinal cord also may contribute (Rashid M H, et al., Pain 125:125-135, 2006).

Central $\alpha 3*$ nAChRs may contribute to nicotinic analgesia (Khan I M, et al., J Neurocytol. 33:543-556, 2004), but $\alpha 3\beta 4$ ligands are of little interest because of likely autonomic side effects. Indeed, the goal has been to avoid $\alpha 3*$ neuronal nicotinic receptor (NNR), as the dose-limiting emetic liability of nonselective compounds has been attributed to activation of $\alpha 3$ containing nAChRs. $\alpha 3*$ nAChRs are expressed in the enteric nervous system as well as in other components of the peripheral and central nervous systems. Area postrema and nucleus tractus solitarius are brainstem nuclei thought to be involved in nausea and emesis. $\alpha 3*$ nAChRs in the dorsal motor nucleus of the vagus and in nucleus tractus solitarius have been implicated in gastric and blood pressure responses to nicotine injected locally (Ferreira M, et al J. Pharmacol. Exp. Ther., 294:230-238, 2000).

Compounds with varying degrees of selectivity for $\alpha 4\beta 2$ nAChRs over other nicotinic subtypes ($\alpha 3$, $\alpha 7$, $\alpha 1$-containing) have been discovered over the years. For example, ABT-594 (referred to as Compound A in this application) was efficacious across a number of rodent models of nociception including acute thermal, chemogenic, neuropathic, and visceral pain (Decker M W, et al., Expert Opinion on Investigational Drugs, 10:1819-1830, 2001). Available data suggest that ligands with selectivity for the $\alpha 4\beta 2$ nAChRs over $\alpha 3\beta 4$ efficacy is preferred for low adverse event profiles. In theory, the therapeutic index could be expanded by (a) reducing $\alpha 3\beta 4$ activity or (b) increasing $\alpha 4\beta 2$ efficacy without increasing $\alpha 3\beta 4$ activity. The latter may be achieved by an $\alpha 4\beta 2$ selective positive allosteric modulator (PAM) either alone or in combination with exogenous $\alpha 4\beta 2$ agonist. Positive allosteric modulators can potentiate effects by enhancing the efficacy and or potency of agonists. Accordingly, an $\alpha 4\beta 2$ selective positive allosteric modulator can selectively enhance effects at the preferred $\alpha 4\beta 2$ nAChRs over other nAChR subtypes.

Initially known positive allosteric modulators of the $\alpha 4\beta 2$ nAChRs have been nonselective and not very potent. For example, nefiracetam has been reported to potentiate $\alpha 4\beta 2$ nAChR responses (Narahashi T, et al., Biol. Pharm. Bull., 27:1701-1706, 2004). More recently, subtype selective PAMs have been disclosed. Compounds like 3-(3-pyridin-3-yl-1,2,4-oxadiazol-5-yl)benzonitrile and others have been described with robust $\alpha 4\beta 2$ PAM effects with little modulatory activity at other subtypes such as $\alpha 3\beta 4$ (e.g., see WO 2006/114400, published Nov. 2, 2006).

Pain is an unmet medical need and the methods and possibilities for treatments of such indications are insufficient. Although continued efforts are being made to treat pain using nAChR agonists, robust efficacy in pain may be limited by the range of side effects associated with their use, albeit to differing degrees. In light of the significance of chronic pain and the limitations in their treatment, it would be beneficial to identify new methods of treating such disorders, particularly in a manner that reduces adverse ganglionic effects such as at the gastrointestinal systems (e.g. emesis). It would be particularly beneficial to identify compounds and compositions that offer an opportunity to wide the therapeutic window of nicotinic (nAChR) agonists in pain. Enhanced efficacy with nAChR ligands for the treatment of other central nervous system diseases such as cognitive and attention deficits is also desirable.

SUMMARY OF THE INVENTION

The invention relates to oxadiazole compounds, compositions comprising such compounds, and methods of using such compounds and compositions.

In one aspect, the invention is directed to compounds of formula II

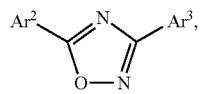

wherein Ar$^1$ and Ar$^2$ are independently optionally substituted aryl or heteroaryl, or a pharmaceutically acceptable salt thereof.

Another aspect of the invention relates to pharmaceutical compositions comprising compounds of the invention. Such compositions can be administered in accordance with a method of the invention, typically as part of a therapeutic regimen for treatment or prevention of conditions and disorders related to nAChR activity, and more particularly α4β2 nAChR positive allosteric modulator activity.

Yet another aspect of the invention relates to a method of modulating α4β2 nAChR positive allosteric modulator activity. The method is useful for treating, preventing or both treating and preventing conditions and disorders related to α4β2 nAChR positive allosteric modulator activity, particularly in mammals.

One embodiment of this invention provides compositions that are useful for treatment of diseases or disorders related to the nicotinic acetylcholine receptor (nAChR) with enhanced efficacy and less side effects than nicotinic agents alone.

Another embodiment of the invention relates to methods and compositions wherein the efficacy of a nicotinic (nAChR) agent is enhanced by co-dosing a nicotinic ligand with a positive allosteric modulator (PAM) of nAChR subtype α4β2. Another embodiment of the invention relates to methods and compositions for treatment of individuals with nAChR-mediated diseases or disorders, and particularly for pain or CNS disorders, which involves a combination of a nicotinic ligand with an α4β2 positive allosteric modulator.

In one embodiment, the invention relates to methods and compositions comprising (i) a nicotinic acetylcholine receptor ligand; and (ii) a nicotinic acetylcholine receptor subtype α4β2 selective positive allosteric modulator, in admixture with at least one pharmaceutically acceptable excipient.

DETAILED DESCRIPTION OF THE INVENTION

Definition of Terms

Figure 1A:
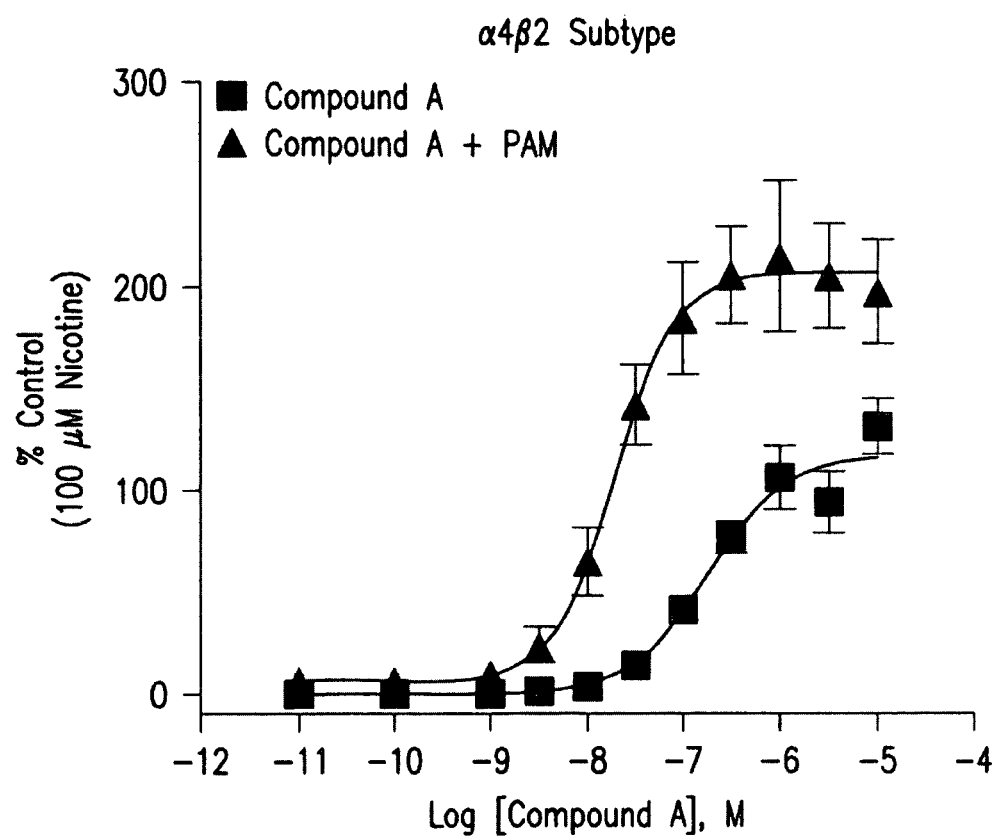
FIGS. 1A and 1B depict responses of a representative nicotinic acetylcholine receptor ligand, 5-[(2R)-azetidin-2-ylmethoxy]-2-chloropyridine (Compound A) in the absence and presence of a nicotinic acetylcholine receptor subtype α4β2 positive allosteric modulator, 3-(3-(pyridin-3-yl)-1,2,4-oxadiazol-5-yl)benzonitrile (PAM, Compound 1), at human α4β2 or α3β4 nicotinic acetylcholine receptor subtypes expressed in HEK-293 cells. The data demonstrate a leftward shift in potency (EC$_{50}$ value) at α4β2, but not α3β4, nAChRs.

For a variable that occurs more than one time in any substituent or in the compound of the invention or any other formulae herein, its definition at each occurrence is independent of its definition at every other occurrence. Combinations of substituents are permissible only if such combinations result in stable compounds.

As used throughout this specification and the appended claims, the designation $C_x$-$C_y$, wherein x and y are integers from 1 to 10 refer to a range of carbon atoms in the hydrocarbon portion of the group which it modifies, for example, the designation "$C_1$-$C_6$ haloalkyl" refers to at least one halogen appended to the parent molecular moiety through an alkyl group having from 1 to 6 carbon atoms.

As used in the specification and the appended claims, unless specified to the contrary, the following terms have the meaning indicated:

The term "acyl hydrazide", as used herein, means a —C(O)NHNH$_2$ group.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl", as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl", as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxycarbonylamino", as used herein, means an alkoxycarbonyl group, as defined herein, appended to the parent molecular moiety through an amino group, as defined herein. Representative examples of alkoxycarbonyamino include, but are not limited to, t-butoxycarbonylamino and methoxycarbonylamino.

The term "alkoxycarbonylaminoalkyl", as used herein, means an alkoxycarbonylamino group, as defined herein, appended to the parent molecular moiety through an alkyl group, as defined herein. Representative examples of alkoxycarbonyaminoalkyl include, but are not limited to, t-butoxycarbonylaminomethyl and methoxycarbonylaminopropyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino", as used herein, means an alkyl group, as defined herein, appended to the parent molecular moiety through an amino group, as defined herein. Representative examples of alkylamino include, but are not limited to, methylamino, ethylamino, and t-butylamino.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl", as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonyloxyalkyl", as used herein, means an alkylcarbonyloxy group, as defined herein, appended to the parent molecular moiety through an alkyl group.

The term "alkylene", as used herein, means a divalent group derived from a straight or branched chain hydrocarbon of from 1 to 10 carbon atoms. Representative examples of alkylene include, but are not limited to, —CH$_2$—, —CH (CH₃)—, —C(CH₃)₂—, —CH₂CH₂—, —CH₂CH₂CH₂—, —CH₂CH₂CH₂CH₂—, and —CH₂CH(CH₃)CH₂—.

The term "alkylsulfinyl", as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl", as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl", as used herein, means an alkylsulfonyl group, as defined herein, appended to the parent molecular moiety through an alkyl group, as defined The term "alkylthio", as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkylthioalkyl", as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino", as used herein, means a —NH₂ group.

The term "aminoalkyl", as used herein, means at least one amino group, as defined herein, is appended to the parent molecular moiety through an alkyl group, as defined herein. Representative examples of hydroxyalkyl include, but are not limited to, aminomethyl, 2-aminoethyl, 3-aminopropyl, and 2-ethyl-4-aminoheptyl.

The term "amido", as used herein, means an amino (H₂N—), alkylamino (alkylN(H)—), dialkylamino (alkyl₂N—), arylamino (arylN(H)—), arylalkylamino (arylalkylN(H)—) or another substituted amine group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "aryl," as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 0, 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylcarbonyloxyalkyl, alkylsulfinyl, alkylsulfinylalkyl, alkylsulfonyl, alkylsulfonylalkyl, alkylthio, alkylthioalkyl, alkynyl, arylalkyl, arylalkoxy, aryloxy, carboxy, carboxyalkyl, cyano, cyanoalkyl, formyl, formylalkyl, halogen, haloalkyl, haloalkoxy, hydroxy, hydroxyalkyl, mercapto, nitro, —NZ¹Z², and (NZ³Z⁴)carbonyl.

The term "arylalkoxy", as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy", as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl", as used herein, means a —C(O)— group.

The term "carboxy", as used herein, means a —CO₂H group.

The term "carboxyalkyl", as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The terms "comprise", "comprises" and "comprising", as used herein, are transitional terms, which are synonymous with "including," "containing," or "characterized by," are inclusive or open-ended and do not exclude additional, unrecited elements or method steps.

The term "concurrent administration" refers to administering the α4β2 receptor ligand to a patient, who has been prescribed (or has consumed) at least one an α4β2 PAM, at an appropriate time so that the patient's symptoms may subside. This may mean simultaneous administration of an α4β2 PAM and an α4β2 receptor ligand, or administration of the medications at different, but appropriate times. Establishing such a proper dosing schedule will be readily apparent to one skilled in the art, such as a physician treating various pain states.

The term "cyano", as used herein, means a —CN group.

The term "cyanoalkyl", as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl", as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl", as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —NZ$^1$Z$^2$, and (NZ$^3$Z$^4$)carbonyl.

The term "cycloalkylalkyl", as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "dialkylamino," as used herein, refers to two independent alkyl groups, as defined herein, appended to the parent molecular moiety through an amino group, as defined herein. Representative examples of dialkylamino include, but are not limited to, dimethylamino, diethylamino, ethylmethylamino, butylmethylamino, ethylhexylamino, and the like.

The term "dialkylaminoalkyl", as used herein, means a dialkyl group, as defined herein, appended to the parent molecular moiety through an alkyl group, as defined herein. Representative examples of dialkylaminoalkyl include, but are not limited to, dimethylaminomethyl and dimethylaminoethyl.

The term "dialkylsulfonylformimidamide" as used herein, means a —SO$_2$N═CH—N(alkyl)$_2$ group.

The term "formyl", as used herein, means a —C(O)H group.

The term "formylalkyl", as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkylcarbonyl", as used herein, means a haloalkyl group, as defined herein, appended to the parent molecular moiety through a carbonyl group, as defined herein. Representative examples of haloalkylcarbonyl include, but are not limited to, trichloromethylcarbonyl and trifluoromethylcarbonyl.

The term "heteroaryl", as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl, or a monocyclic heteroaryl fused to a monocyclic heterocycle. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzo[d][1,3]dioxolyl, benzofuranyl, benzoxadiazolyl, benzo[d]imidazolyl, benzo[d]imidazle-2(3H)-thione, benzoisoxazole, benzoisothiazole, benzooxazole, benzooxazolone, benzo[d][1,2,3]thiadiazolyl, 1,3-benzothiazolyl, benzothiophenyl, benzo[d][1,2,3]triazolyl, cinnolinyl, 2,2-difluorobenzo[d][1,3]dioxolyl, furopyridine, imidazopyridinyl, indolyl, indazolyl, isobenzofuran, isoindolyl, isoquinolinyl, naphthyridinyl, oxazolopyridine, pyrazolopyrimidinyl, pyrrolopyridinyl, quinolinyl, quinoxalinyl, thienopyridinyl, and [1,2,4]triazolopyridinyl.

The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —NZ$^1$Z$^2$, (NZ$^3$Z$^4$)carbonyl and oxo. Heteroaryl groups of the invention that are substituted with a hydroxyl group may be present as tautomers. The heteroaryl groups of the invention encompass all tautomers including non-aromatic tautomers.

The term "heterocycle" or "heterocyclic", as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, nitro, mercapto, oxo, —NZ$^1$Z$^2$ and (NZ$^3$Z$^4$)carbonyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl", as used herein, is a subset of alkenyl, as defined herein, and means an alkenyl group containing from 2 to 4 carbon atoms. Examples of lower alkenyl are ethenyl, propenyl, and butenyl.

The term "lower alkoxy", as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl", as used herein, is a subset of alkyl, as defined herein, and means a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower haloalkoxy", as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl", as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "mammal" includes humans and animals, such as cats, dogs, swine, cattle, horses, and the like.

The term "methylenedioxy", as used herein, means a —OCH$_2$O— group wherein the oxygen atoms of the methylenedioxy are attached to the parent molecular moiety through two adjacent carbon atoms.

The term "nitrogen protecting group", as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "mercapto", as used herein, means a —SH group.

The term "nitro", as used herein, means a —NO$_2$ group.

The term "NZ$^1$Z$^2$", as used herein, means two groups, Z$^1$ and Z$^2$, which are appended to the parent molecular moiety through a nitrogen atom. Z$^1$ and Z$^2$ are each independently selected from the group consisting of hydrogen, alkyl, alkylcarbonyl, alkoxycarbonyl, aryl, arylalkyl, and formyl. In certain instances within the invention, Z$^1$ and Z$^2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$^3$Z$^4$", as used herein, means two groups, Z$^3$ and Z$^4$, which are appended to the parent molecular moiety through a nitrogen atom. Z$^3$ and Z$^4$ are each The term "oxo", as used herein, means a =O moiety.

The term "pharmaceutically acceptable amide," as used herein, refers to those amides, which retain, upon hydrolysis of the amide bond, the biological effectiveness and properties of the carboxylic acid and are not biologically or otherwise undesirable. Pharmaceutically acceptable amides of the invention can be derived from ammonia, primary C$_{1-6}$ alkyl amines and secondary C$_{1-6}$ dialkyl amines. In the case of secondary amines, the amine can also be in the form of a 5- or 6-membered heterocycle containing one nitrogen atom. Amides derived from ammonia, C$_{1-3}$ alkyl primary amides and C$_{1-2}$ dialkyl secondary amides are preferred. Amides of the compounds of formulas (I) and (II) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug" as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of the invention, for example, by hydrolysis in blood. A thorough discussion is provided in Higuchi T., et al., Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "pharmaceutically acceptable carrier" as used herein, means a non-toxic, solid, semi-solid or liquid filler, diluent, encapsulating material, or formulation auxiliary of any type. Examples of therapeutically suitable excipients include sugars; cellulose and derivatives thereof, oils; glycols; solutions; buffering, coloring, releasing, coating, sweetening, flavoring, and perfuming agents; and the like. These therapeutic compositions can be administered parenterally, intracisternally, orally, rectally, intraveneously, or intraperitoneally.

The term "sulfinyl", as used herein, means a —S(O)— group."

The term "sulfonamide", as used herein means an amino, alkylamino, or dialkylamino group, as defined herein, appended to the parent molecular moiety through a sulfonyl group, as defined herein. Representative examples include, but are not limited to, aminosulfonyl, methylaminosulfonyl, and diethylaminosulfonyl.

The term "sulfonyl", as used herein, means a —$SO_2$— group.

The term "tautomer", as used herein, means a proton shift from one atom of a compound to another atom of the same compound wherein two or more structurally distinct compounds are in equilibrium with each other.

The term "radiolabel" refers to a compound in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I. Compounds suitable for the composition, method, and article of manufacture for the invention are any chemical compounds for which α4β2 nicotinic receptor activity can be identified.

The term "treatment" or "treating" includes any process, action, application, therapy, or the like, wherein a subject, including human, is provided medical aid with the object of improving the subject's condition, directly or indirectly, or slowing the progression of a condition or disorder in the subject.

Although typically it may be recognized that an asterisk is used to indicate that the exact subunit composition of a receptor is uncertain, for example α4β2* indicates a receptor that contains the α4 and β2 subunit proteins in combination with other subunits.

It has been found that the efficacy of nicotinic receptor ligands surprisingly can be improved by combining a nicotinic acetylcholine receptor ligand, particularly an α4β2 receptor ligand (agonist, partial agonist), with a nicotinic acetylcholine receptor α4β2 subtype selective positive allosteric modulator (PAM). Such combinations are highly efficient for improving the efficacy of α4β2 ligand for treatment of pain and other disease indications such as cognitive deficits when compared to administration of an α4β2 receptor ligand alone.

Nicotinic Acetylcholine Subtype α4β2 Receptor Ligands

Nicotinic acetylcholine subtype α4β2 receptor ligands modulate the function by altering the activity of the receptor. Suitable compounds also can be partial agonists that partially block or partially activate the α4β2 receptor or agonists that activate the receptor. Nicotinic acetylcholine receptor α4β2 receptor ligands suitable for the invention can include full agonists or partial agonists. Compounds modulating activity of nicotinic acetylcholine receptor α4β2 subtype are suitable for the invention regardless of the manner in which they interact with the receptor.

One manner for characterizing α4β2 receptor ligands is by a binding assay. [$^3$H]-Cytisine binding values ("$K_i$ Cyt") of compounds of the invention ranged from about 0.001 nanomolar to greater than 100 micromolar. Preferred compounds for the composition demonstrate binding values of from about 0.001 nanomolar to 10 micromolar. The [$^3$H]-cytisine binding assays have been well reported; however, further details for carrying out the assays can be obtained in International Publication No. WO 99/32480; U.S. Pat. Nos. 5,948,793 and 5,914,328; WO 2004/018607; U.S. Pat. No. 6,809,105; WO 00/71534; and U.S. Pat. No. 6,833,370.

Accordingly, α4β2 receptor ligands suitable for the invention can be compounds of various chemical classes. Particularly, some examples of α4β2 receptor ligands suitable for the invention include, but are not limited to heterocyclic ether derivatives (see, for example, International Publication No. WO 99/32480, published Jul. 1, 1999; U.S. Pat. No. 5,948, 793, issued Sep. 7, 1999, and U.S. Pat. No. 5,914,328, issued Jun. 22, 1999); N-substituted diazabicyclic derivatives (see for example International Publication No. WO 2004/0186107, published Sep. 23, 2004, and U.S. Pat. No. 6,809, 105, issued Oct. 26, 2004); heterocyclic substituted amino azacycles (see for example, International Publication No. WO 00/71534, published Nov. 30, 2000, and U.S. Pat. No. 6,833,370, issued Dec. 21, 2004); all of which are hereby incorporated by reference in their entirety. Further description and methods for preparing the compounds have been reported in the patents, patent publications, and international patent publications cited.

Additional examples of α4β2 receptor ligands suitable for the invention include, but are not limited to aryl-fused azapolycyclic compounds (see for example, International Publication No. WO 2001062736, published Aug. 30, 2001); aryl-substituted olefinic amine compounds (see for example, International Publication Nos. WO 9965876, published Dec.

23, 1999, and WO 00/75110, published Dec. 14, 2000); pyridopyranoazepine derivatives (see for example, U.S. Pat. No. 6,538,003, published Mar. 25, 2003); benzylidene- and cinnamylidene-anabaseines (see for examples, International Publication No. WO 99/10338, published Mar. 4, 1999); and 3-pyridoxylalkyl heterocyclic ether compounds (see for example, International Publication No. WO 96/040682, published Dec. 19, 1996); all of which are hereby incorporated by reference in their entirety. Further description and methods for preparing the compounds have been reported in the patents and international patent publications cited.

Other compounds reported as demonstrating α4β2 ligands include, but are not limited to, TC-1734 (ispronicline), GTS-21, 4-hydroxy-GTS-21, TC-5619, TC-2696, dianicline and varenicline, which are all described in the publicly available literature.

Specific examples of compounds contemplated for the α4β2 receptor ligands include, but are not limited to,
5-[(2R)-azetidin-2-ylmethoxy]-2-chloropyridine;
(3R)-1-pyridin-3-ylpyrrolidin-3-amine;
2-methyl-3-(2-(S)-pyrrolidinylmethoxy)pyridine;
3-(5,6-dichloro-pyridin-3-yl)-1S,5S-3,6-diazabicyclo[3.2.0]heptane;
(R,R)-1-(pyridin-3-yl)octahydro-pyrrolo[3,4-b]pyrrole;
6,10-methano-6H-pyrazino[2,3-h][3]benzazepine;
7,8,9,10-tetrahydro-(2S,4E)-N-methyl-5-(5-isopropoxy-3-pyridyl)-4-penten-2-amine;
(2S,4E)-N-methyl-5-(5-methoxy-3-pyridyl)-4-penten-2-amine;
(2S,4E)-N-methyl-5-(5-ethoxy-3-pyridyl)-4-penten-2-amine;
(2S,4E)-N-methyl-3-pyrimidine-4-penten-2-amine;
(5aS,8S,10aR)-5a,6,9,10-tetrahydro-7H,11H-8,10a-methanopyrido[2',3':5,6]pyrano[2,3-d]azepine;
3-[1-(2,4-dimethoxy-phenyl)-meth-(E)-ylidene]-3,4,5,6-tetrahydro-[2,3']bipyridinyl; and
3-[1-(2-methoxy-4-hydroxyphenyl)-meth-(E)-ylidene]-3,4,5,6-tetrahydro-[2,3']bipyridinyl;
or pharmaceutically acceptable salts thereof.

Nicotinic Acetylcholine Subtype α4β2 Receptor Positive Allosteric Modulators

Positive allosteric modulators (PAMs) are compounds that potentiate receptor responses to acetylcholine without themselves triggering receptor activation or desensitization, or either, of the receptor.

One manner for characterizing α4β2 positive allosteric modulator activity is by characterization in human HEK cells expressing the human nicotinic acetylcholine receptor subtype α4β2, particularly by use of Fluorescent Image Plate Reader technology. Such assay has been reported and further details for carrying out the assays can be obtained in International Publication Nos. WO 2006/114400, published Nov. 2, 2006. Another method to identify and characterize allosteric modulator activity is by expressing the α4β2 subunits in *Xenopus* oocytes or cell lines, and by measuring effects on ligand-evoked current responses as previously described (Curtis L, et al., *Molecular Pharmacology*, 61: 127-135, 2002).

Steroid hormones represent a family of molecules with varying modulatory effects on nAChRs as well as other members of the LGIC superfamily. For example, positive allosteric modulation of human α4β2 nAChRs expressed either in *Xenopus* oocytes or in human embryonic kidney cells was reported with 17β-estradiol (Curtis L, et al., *Molecular Pharmacology*, 61: 127-135, 2002). Examples of compounds reported as selective α4β2 positive allosteric modulators are oxadiazole derivatives, for example as described in WO 2006/114400.

Another suitable α4β2 positive allosteric modulator is 3,5-diphenylisoxazole, which is commercially available from Sigma Aldrich, St. Louis, Mo., USA.

Other suitable examples of α4β2 positive allosteric modulators include, but are not limited to, oxadiazole derivatives. Suitable oxadiazole derivatives can include 1,2,4-oxadiazole derivatives and 1,3,4-oxadiazole derivatives. Examples of 1,3,4-oxadiazole derivatives are described in co-pending U.S. Patent Application No. 61/000,295, filed on Apr. 12, 2007, wherein the methods of preparation disclosed are incorporated by reference herein. Such compounds have the formula (I):

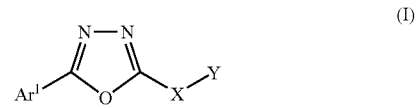

or are pharmaceutically acceptable salts and prodrugs thereof, wherein
X is a bond, O, NR$^1$, S, or C$_1$-C$_3$ alkylene;
Y represents a monocyclic aryl, cycloalkyl, heterocycle, or heteroaryl group;
Ar$^1$ represents a monocyclic aryl or a heteroaryl group; and
R$^1$ is hydrogen, alkyl, haloalkyl or arylalkyl.

X is selected from a bond, O, NR$^1$, S, or C$_1$-C$_3$ alkylene, wherein R$^1$ is selected from hydrogen, alkyl, haloalkyl, and arylalkyl. Preferably, X is a bond. Preferably, R$^1$ is hydrogen or alkyl.

Y represents a monocyclic aryl, cycloalkyl, heterocycle, or heteroaryl group, which can be substituted or unsubstituted with substituents. Examples of suitable heterocycle groups can include, but are not limited to, pyrrolidine, piperidine, and the like. Examples of suitable heteroaryl groups can include, but are not limited to, thienyl, furanyl, pyridinyl, pyrazinyl, and the like. A preferred monocyclic aryl group is substituted or unsubstituted phenyl. Suitable substituents for the monocyclic aryl, heterocycle, or heteroaryl group are, for example, alkyl, cycloalkyl, cycloalkylalkyl, halo, haloalkyl, hydroxyl, alkoxy, haloalkoxy, nitro, and cyano.

Ar$_1$ represents a monocyclic aryl, such as substituted or unsubstituted phenyl, or heteroaryl group. Examples of suitable heteroaryl groups include, but are not limited, thienyl, furanyl, pyrrolyl, pyrazolyl, thiazolyl, 1,3,4-thiadiazolyl, and pyridinyl, each of which can be unsubstituted or substituted with one, two, or three substituents selected from alkyl, cycloalkyl, cycloalkylalkyl, halo, haloalkyl, hydroxyl, alkoxy, haloalkoxy, nitro, cyano, and amino.

In one embodiment, suitable 2,5-disubstituted-1,3,4-oxadiazole derivatives can have the formula (I) wherein X is a bond; Y is aryl, cycloalkyl, heterocycle, or heteroaryl; and Ar$^1$ is monocyclic aryl or heteroaryl.

In another embodiment, suitable 2,5-disubstituted-1,3,4-oxadiazole derivatives can have the formula (I) wherein X is a bond; Y is monocyclic cycloalkyl, phenyl, thienyl, furyl, pyridinyl, pyrazinyl, pyrrolidinyl, or piperidinyl optionally substituted with one or more of the substituents selected from the group consisting of alkyl, halogen, haloalkyl, hydroxy, alkoxy, haloalkoxy, nitro and cyano; and Ar$^1$ is phenyl, thienyl, furyl, pyrrolyl, pyrazolyl, thiazolyl, 1,3,4-thiadiazolyl, pyrimidinyl, pyrazinyl, or pyridinyl optionally substituted with one or more of the substituents selected from the group consisting of alkyl, alkylcarbonyl, alkylsulfonyl, alkylthio, arylalkyl, aryloxy, arylalkyloxy, halogen, haloalkyl, hydroxy, alkoxy, haloalkoxy, nitro, cyano, and $NZ^1Z^2$, wherein $Z^1$ and $Z^2$ are hydrogen, alkyl, alkylcarbonyl, alkoxycarbonyl, aryl, arylalkyl, or formyl.

In another embodiment, the suitable 2,5-disubstituted-1,3, 4-oxadiazole derivatives can have the formula (I) wherein X is a bond; Y is pyridyl; and $Ar^1$ is phenyl, pyrimidinyl, pyrazinyl, or pyridinyl optionally substituted with one or more of the substituents selected from the group consisting of alkyl, halogen, haloalkyl, hydroxy, alkoxy, haloalkoxy, nitro, cyano, and $NZ^1Z^2$, wherein $Z^1$ and $Z^2$ are hydrogen, alkyl, alkylcarbonyl, alkoxycarbonyl, aryl, arylalkyl, or formyl.

Other suitable examples of compounds reported as α4β2 positive allosteric modulators are oxadiazole derivatives, for example as described in WO 2006/114400, published Nov. 2, 2006. Further examples of oxadiazole compounds that are suitable as α4β2 positive allosteric modulators are also provided in WO 02/100826, published Dec. 19, 2002.

Yet other suitable examples of α4β2 positive allosteric modulators include, but are not limited to, compounds of the formula (II):

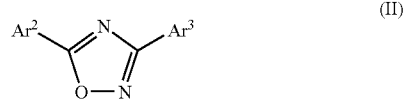

(II)

or are pharmaceutically acceptable salts thereof, wherein $Ar^2$ is aryl or heteroaryl, wherein the aryl or heteroaryl is substituted or unsubstituted, and, when substituted, the aryl or heteroaryl is substituted with 0, 1, 2, 3, or 4 substituents selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_4$-$C_{10}$ heterocycle, $C_1$-$C_6$ alkyl, —($C_1$-$C_6$ alkyl)NHC(O)O—($C_1$-$C_6$ alkyl), $C_1$-$C_6$ hydroxyalkyl, $C_1$-$C_6$ alkylcarbonyl, amino, hydroxyl, haloalkyl-C(O)—, haloalkyl-$SO_2$—, alkyl-$SO_2$—, —$SO_2NH_2$, —$SO_2NH(C_1$-$C_6$ alkyl), —$SO_2N(C_1$-$C_6$ alkyl)$_2$, cyano, nitro, $C_1$-$C_6$ acylamino, $C_1$-$C_6$ alkoxy, —C(O)$NH_2$, —C(O)O—($C_1$-$C_6$ alkyl), and carboxy; and $Ar^3$ is aryl or heteroaryl, wherein the aryl or heteroaryl is optionally substituted, and, when substituted, the aryl or heteroaryl is substituted with a substituent selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_1$-$C_6$ alkyl, $C_1$-$C_6$ hydroxyalkyl, amino, hydroxyl, haloalkyl-$SO_2$—, cyano, nitro, $C_1$-$C_6$ acylamino, $C_1$-$C_6$ alkoxy, —N($C_1$-$C_6$ alkyl)$_2$, and carboxy.

In one embodiment, suitable 3,5-disubstituted-1,2,4-oxadiazole derivatives can have the formula (I) wherein $Ar^2$ is substituted monocyclic aryl or monocyclic heteroaryl, which can be substituted or unsubstituted, and $Ar^3$ is substituted monocyclic aryl or heteroaryl, which can be substituted or unsubstituted. When the aryl or heteroaryl group for $Ar^2$ is substituted the substituent is selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_4$-$C_{10}$ heterocycle, $C_1$-$C_6$ alkyl, —($C_1$-$C_6$ alkyl)NHC(O)O—($C_1$-$C_6$ alkyl), $C_1$-$C_6$ hydroxyalkyl, $C_1$-$C_6$ alkylcarbonyl, amino, hydroxyl, haloalkyl-C(O)—, haloalkyl-$SO_2$—, alkyl-$SO_2$—, —$SO_2NH_2$, —$SO_2NH(C_1$-$C_6$ alkyl), —$SO_2N(C_1$-$C_6$ alkyl)$_2$, cyano, nitro, $C_1$-$C_6$ acylamino, $C_1$-$C_6$ alkoxy, —C(O)$NH_2$, —C(O)O—($C_1$-$C_6$ alkyl), and carboxy. When the aryl or heteroaryl group for $Ar^3$ is substituted the substituent is selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_1$-$C_6$ alkyl, $C_1$-$C_6$ hydroxyalkyl, amino, hydroxyl, haloalkyl-$SO_2$—, cyano, nitro, $C_1$-$C_6$ acylamino, $C_1$-$C_6$ alkoxy, —N($C_1$-$C_6$ alkyl)$_2$, and carboxy. Preferred for monocyclic heteroaryl are pyridine-3-yl, pyridine-4-yl, and pyridine-2 (1H)-one.

In another embodiment, suitable 3,5-disubstituted-1,2,4-oxadiazole derivatives can have the formula (II) wherein $Ar^2$ is pyridinyl, which can be substituted or unsubstituted, or substituted phenyl; and $Ar^3$ is pyridinyl, which can be substituted or unsubstituted, or substituted phenyl. The pyridinyl group, when substituted, is substituted with fluoro. The phenyl group is substituted with cyano or halo. It is preferred that the pyridinyl group for $Ar^2$ or $Ar^3$ is pyridin-3-yl. The preferred phenyl group is substitute with fluoro, sulfonamide or cyano, and preferably cyano.

Specific examples of α4β2 positive allosteric modulators are, for example, 3,5-disubstituted-1,2,4-oxadiazole derivatives, such as:

3-(3-(pyridin-3-yl)-1,2,4-oxadiazol-5-yl)benzonitrile;
3,5-di(pyridin-3-yl)-1,2,4-oxadiazole;
3-(5-(pyridin-3-yl)-1,2,4-oxadiazol-3-yl)benzonitrile;
3-(5-(6-fluoropyridin-3-yl)-1,2,4-oxadiazol-3-yl)benzonitrile;
5-(5-bromopyridin-3-yl)-3-(pyridin-3-yl)-1,2,4-oxadiazole;
3-(pyridin-3-yl)-5-(3-(trifluoromethylsulfonyl)phenyl)-1,2,4-oxadiazole;
3-(3-(6-methylpyridin-3-yl)-1,2,4-oxadiazol-5-yl)benzonitrile;
5-(5-(pyrrol-1-yl)pyridin-3-yl)-3-(pyridin-3-yl)-1,2,4-oxadiazole;
5-(3-(pyridin-3-yl)-1,2,4-oxadiazol-5-yl)pyridin-3-ol;
5-(3,4-difluorophenyl)-3-(pyridin-3-yl)-1,2,4-oxadiazole;
5-(2,3-difluorophenyl)-3-(pyridin-3-yl)-1,2,4-oxadiazole;
5-(pyrazin-2-yl)-3-(pyridin-3-yl)-1,2,4-oxadiazole;
5-(3,5-difluorophenyl)-3-(pyridin-3-yl)-1,2,4-oxadiazole;
5-(2,3,5-trifluorophenyl)-3-(pyridin-3-yl)-1,2,4-oxadiazole;
5-(2,4,5-trifluorophenyl)-3-(pyridin-3-yl)-1,2,4-oxadiazole;
5-(2,5-difluorophenyl)-3-(pyridin-3-yl)-1,2,4-oxadiazole;
5-(4-chloro-2,5-difluorophenyl)-3-(pyridin-3-yl)-1,2,4-oxadiazole;
5-(5-methylpyrazin-2-yl)-3-(pyridin-3-yl)-1,2,4-oxadiazole;
4-(3-(pyridin-3-yl)-1,2,4-oxadiazol-5-yl)benzonitrile;
2,3,6-trifluoro-5-(3-(pyridin-3-yl)-1,2,4-oxadiazol-5-yl) phenol;
2-fluoro-5-(3-(pyridin-3-yl)-1,2,4-oxadiazol-5-yl)phenol;
2-fluoro-4-(3-(pyridin-3-yl)-1,2,4-oxadiazol-5-yl)phenol;
5-(3-chloro-4-fluorophenyl)-3-(pyridin-3-yl)-1,2,4-oxadiazole;
5-(3,4-dichlorophenyl)-3-(pyridin-3-yl)-1,2,4-oxadiazole;
2-nitro-5-(3-(pyridin-3-yl)-1,2,4-oxadiazol-5-yl)phenol;
5-(2,3,6-trifluorophenyl)-3-(pyridin-3-yl)-1,2,4-oxadiazole;
2,2,2-trifluoro-1-(4-(3-(pyridin-3-yl)-1,2,4-oxadiazol-5-yl) phenyl)ethanone;
5-(3-fluorophenyl)-3-(pyridin-3-yl)-1,2,4-oxadiazole;
5-(4-fluorophenyl)-3-(pyridin-3-yl)-1,2,4-oxadiazole;
5-(2-fluorophenyl)-3-(pyridin-3-yl)-1,2,4-oxadiazole;
3-fluoro-5-(3-(pyridin-3-yl)-1,2,4-oxadiazol-5-yl)benzonitrile;
3-(2,3-difluorophenyl)-5-(pyridin-3-yl)-1,2,4-oxadiazole;
3-(3,4-difluorophenyl)-5-(pyridin-3-yl)-1,2,4-oxadiazole;
5-(2,6-difluorophenyl)-3-(pyridin-3-yl)-1,2,4-oxadiazole;
3-(3-(pyridin-3-yl)-1,2,4-oxadiazol-5-yl)benzenesulfonamide;
5-(2,4-difluorophenyl)-3-(pyridin-3-yl)-1,2,4-oxadiazole;
5-(2,3,4-trifluorophenyl)-3-(pyridin-3-yl)-1,2,4-oxadiazole;
5-(3,4,5-trifluorophenyl)-3-(pyridin-3-yl)-1,2,4-oxadiazole;

5-(4-chloro-3-fluorophenyl)-3-(pyridin-3-yl)-1,2,4-oxadiazole;
5-(3-nitrophenyl)-3-(pyridin-3-yl)-1,2,4-oxadiazole;
5-(3-(methylsulfonyl)phenyl)-3-(pyridin-3-yl)-1,2,4-oxadiazole;
3-(2-chloropyridin-4-yl)-5-(pyridin-3-yl)-1,2,4-oxadiazole;
3-(3-(pyridin-3-yl)-1,2,4-oxadiazol-5-yl)benzamide;
4-(5-(pyridin-3-yl)-1,2,4-oxadiazol-3-yl)pyridin-2(1H)-one;
tert-butyl 3-(3-(pyridin-3-yl)-1,2,4-oxadiazol-5-yl)benzoate;
2-amino-5-(3-(pyridin-3-yl)-1,2,4-oxadiazol-5-yl)phenol;
N,N-dimethyl-4-(5-(pyridin-3-yl)-1,2,4-oxadiazol-3-yl)pyridin-2-amine;
3-(3-(pyridin-3-yl)-1,2,4-oxadiazol-5-yl)benzoic acid;
5-(3-(1H-tetrazol-5-yl)phenyl)-3-(pyridin-3-yl)-1,2,4-oxadiazole;
N,N-diethyl-3-(3-(pyridin-3-yl)-1,2,4-oxadiazol-5-yl)benzenesulfonamide;
2-fluoro-5-(3-(pyridin-3-yl)-1,2,4-oxadiazol-5-yl)benzonitrile;
3-(3-(1H-tetrazol-5-yl)phenyl)-5-(pyridin-3-yl)-1,2,4-oxadiazole;
3-(6-chloropyridin-3-yl)-5-(pyridin-3-yl)-1,2,4-oxadiazole;
5-(6-chloropyridin-3-yl)-3-(pyridin-3-yl)-1,2,4-oxadiazole;
5-(5-(pyridin-3-yl)-1,2,4-oxadiazol-3-yl)pyridin-2(1H)-one;
5-(3-(pyridin-3-yl)-1,2,4-oxadiazol-5-yl)pyridin-2(1H)-one;
N-methyl-3-(3-(pyridin-3-yl)-1,2,4-oxadiazol-5-yl)benzenesulfonamide;
3-(3-(pyridin-3-yl)-1,2,4-oxadiazol-5-yl)aniline;
(3-(3-(pyridin-3-yl)-1,2,4-oxadiazol-5-yl)phenyl)methanamine;
5-(2-chloropyridin-4-yl)-3-(pyridin-3-yl)-1,2,4-oxadiazole;
4-(3-(pyridin-3-yl)-1,2,4-oxadiazol-5-yl)pyridin-2(1H)-one;
tert-butyl 3-(3-(pyridin-3-yl)-1,2,4-oxadiazol-5-yl)benzylcarbamate;
5-(3-bromophenyl)-3-(pyridin-3-yl)-1,2,4-oxadiazole;
1-(3-(3-(pyridin-3-yl)-1,2,4-oxadiazol-5-yl)phenyl)pyrrolidin-2-one;
tert-butyl 3-(3-(pyridin-3-yl)-1,2,4-oxadiazol-5-yl)phenylcarbamate;
N,N-dimethyl-1-(3-(3-(pyridin-3-yl)-1,2,4-oxadiazol-5-yl)phenyl)methanamine;
5-(3-(piperazin-1-yl)phenyl)-3-(pyridin-3-yl)-1,2,4-oxadiazole;
1-(3-(3-(pyridin-3-yl)-1,2,4-oxadiazol-5-yl)phenyl)ethanone;
3-(6-chloropyridin-3-yl)-5-(2,3-difluorophenyl)-1,2,4-oxadiazole;
3-(6-chloropyridin-3-yl)-5-(3,4-difluorophenyl)-1,2,4-oxadiazole;
(R)-3-(pyridin-3-yl)-5-(3-(pyrrolidin-2-yl)phenyl)-1,2,4-oxadiazole;
5-(3-(1H-pyrazol-3-yl)phenyl)-3-(pyridin-3-yl)-1,2,4-oxadiazole;
1-(3-(3-(pyridin-3-yl)-1,2,4-oxadiazol-5-yl)phenyl)ethanol;
3-(3-(6-chloropyridin-3-yl)-1,2,4-oxadiazol-5-yl)benzonitrile;
3-(4-fluorophenyl)-5-(pyridin-3-yl)-1,2,4-oxadiazole;
3-(5-(6-chloropyridin-3-yl)-1,2,4-oxadiazol-3-yl)benzonitrile;
3-(5-(2-fluoropyridin-3-yl)-1,2,4-oxadiazol-3-yl)benzonitrile, and
3-fluoro-5-(5-(pyridin-3-yl)-1,2,4-oxadiazol-3-yl)benzonitrile;
or pharmaceutically acceptable salts thereof.

Other specific examples of α4β2 positive allosteric modulators are, for example, 2,5-disubstituted-1,3,4-oxadiazole derivatives, such as:

2-(imidazo[1,5-a]pyridin-6-yl)-5-(pyridin-3-yl)-1,3,4-oxadiazole
2,5-di(pyridin-3-yl)-1,3,4-oxadiazole;
2-(5-bromopyridin-3-yl)-5-(pyridin-3-yl)-1,3,4-oxadiazole;
2-(pyridin-3-yl)-5-(4-(trifluoromethyl)phenyl)-1,3,4-oxadiazole;
2-(pyridin-3-yl)-5-o-tolyl-1,3,4-oxadiazole;
2-(pyridin-3-yl)-5-m-tolyl-1,3,4-oxadiazole;
2-(pyridin-3-yl)-5-p-tolyl-1,3,4-oxadiazole;
2-(5-(pyridin-3-yl)-1,3,4-oxadiazol-2-yl)phenol;
3-(5-(pyridin-3-yl)-1,3,4-oxadiazol-2-yl)phenol;
4-(5-(pyridin-3-yl)-1,3,4-oxadiazol-2-yl)phenol;
2-(3-methoxyphenyl)-5-(pyridin-3-yl)-1,3,4-oxadiazole;
2-(4-methoxyphenyl)-5-(pyridin-3-yl)-1,3,4-oxadiazole;
2-(2-fluorophenyl)-5-(pyridin-3-yl)-1,3,4-oxadiazole;
2-(3-fluorophenyl)-5-(pyridin-3-yl)-1,3,4-oxadiazole;
2-(4-fluorophenyl)-5-(pyridin-3-yl)-1,3,4-oxadiazole;
2-(2-chlorophenyl)-5-(pyridin-3-yl)-1,3,4-oxadiazole;
2-(3-chlorophenyl)-5-(pyridin-3-yl)-1,3,4-oxadiazole;
2-(4-chlorophenyl)-5-(pyridin-3-yl)-1,3,4-oxadiazole;
2-(2-bromophenyl)-5-(pyridin-3-yl)-1,3,4-oxadiazole;
2-(3-bromophenyl)-5-(pyridin-3-yl)-1,3,4-oxadiazole;
2-(4-bromophenyl)-5-(pyridin-3-yl)-1,3,4-oxadiazole;
3-(5-(pyridin-3-yl)-1,3,4-oxadiazol-2-yl)benzonitrile;
4-(5-(pyridin-3-yl)-1,3,4-oxadiazol-2-yl)benzonitrile;
N,N-dimethyl-3-(5-(pyridin-3-yl)-1,3,4-oxadiazol-2-yl)aniline;
N,N-dimethyl-4-(5-(pyridin-3-yl)-1,3,4-oxadiazol-2-yl)aniline;
2-(pyridin-3-yl)-5-(3-(trifluoromethyl)phenyl)-1,3,4-oxadiazole;
2-(pyridin-3-yl)-5-(3-(trifluoromethoxy)phenyl)-1,3,4-oxadiazole;
2-(4-phenoxyphenyl)-5-(pyridin-3-yl)-1,3,4-oxadiazole;
2-(4-(benzyloxy)phenyl)-5-(pyridin-3-yl)-1,3,4-oxadiazole;
2-(3,4-dimethylphenyl)-5-(pyridin-3-yl)-1,3,4-oxadiazole;
2-(3,5-dimethylphenyl)-5-(pyridin-3-yl)-1,3,4-oxadiazole;
2-(2,5-dimethylphenyl)-5-(pyridin-3-yl)-1,3,4-oxadiazole;
2-(2,4-dimethylphenyl)-5-(pyridin-3-yl)-1,3,4-oxadiazole;
2-(3,4-dimethylphenyl)-5-(pyridin-3-yl)-1,3,4-oxadiazole;
2-(2,3-dimethoxyphenyl)-5-(pyridin-3-yl)-1,3,4-oxadiazole;
2-(2,4-dimethoxyphenyl)-5-(pyridin-3-yl)-1,3,4-oxadiazole;
2-(2,5-dimethoxyphenyl)-5-(pyridin-3-yl)-1,3,4-oxadiazole;
2-(2,4-dimethoxyphenyl)-5-(pyridin-3-yl)-1,3,4-oxadiazole;
2-(3,5-dimethoxyphenyl)-5-(pyridin-3-yl)-1,3,4-oxadiazole;
2-(benzo[d][1,3]dioxol-5-yl)-5-(pyridin-3-yl)-1,3,4-oxadiazole;
2-(pyridin-3-yl)-5-(3,4,5-trimethoxyphenyl)-1,3,4-oxadiazole;
2-(3,4-dichlorophenyl)-5-(pyridin-3-yl)-1,3,4-oxadiazole;
2-(2,4-dichlorophenyl)-5-(pyridin-3-yl)-1,3,4-oxadiazole;
2-(2,5-dichlorophenyl)-5-(pyridin-3-yl)-1,3,4-oxadiazole;
2-(3,4-dichlorophenyl)-5-(pyridin-3-yl)-1,3,4-oxadiazole;
5-methyl-2-(5-(pyridin-3-yl)-1,3,4-oxadiazol-2-yl)phenol;
2-methyl-5-(5-(pyridin-3-yl)-1,3,4-oxadiazol-2-yl)phenol;
2-(3-fluoro-2-methylphenyl)-5-(pyridin-3-yl)-1,3,4-oxadiazole;
2-(5-fluoro-2-methylphenyl)-5-(pyridin-3-yl)-1,3,4-oxadiazole;
2-(3-fluoro-4-methylphenyl)-5-(pyridin-3-yl)-1,3,4-oxadiazole;
2-(2,3-difluorophenyl)-5-(pyridin-3-yl)-1,3,4-oxadiazole;
2-(2,4-difluorophenyl)-5-(pyridin-3-yl)-1,3,4-oxadiazole;
2-(2,5-difluorophenyl)-5-(pyridin-3-yl)-1,3,4-oxadiazole;
2-(3,5-difluorophenyl)-5-(pyridin-3-yl)-1,3,4-oxadiazole;
1-(4-(5-(pyridin-3-yl)-1,3,4-oxadiazol-2-yl)phenyl)ethanone;

2-(4-isopropylphenyl)-5-(pyridin-3-yl)-1,3,4-oxadiazole;
2-(3-methoxy-4-methylphenyl)-5-(pyridin-3-yl)-1,3,4-oxadiazole;
2-(4-ethoxyphenyl)-5-(pyridin-3-yl)-1,3,4-oxadiazole;
2-(4-(methylthio)phenyl)-5-(pyridin-3-yl)-1,3,4-oxadiazole;
2-(3-fluoro-4-methoxyphenyl)-5-(pyridin-3-yl)-1,3,4-oxadiazole;
2-(naphthalen-1-yl)-5-(pyridin-3-yl)-1,3,4-oxadiazole;
2-(naphthalen-2-yl)-5-(pyridin-3-yl)-1,3,4-oxadiazole;
4-chloro-2-(5-(pyridin-3-yl)-1,3,4-oxadiazol-2-yl)phenol;
2-(4-tert-butylphenyl)-5-(pyridin-3-yl)-1,3,4-oxadiazole;
N-(4-(5-(pyridin-3-yl)-1,3,4-oxadiazol-2-yl)phenyl)acetamide;
2-(4-propoxyphenyl)-5-(pyridin-3-yl)-1,3,4-oxadiazole;
2-(4-isopropoxyphenyl)-5-(pyridin-3-yl)-1,3,4-oxadiazole;
2-(5-chloro-2-methoxyphenyl)-5-(pyridin-3-yl)-1,3,4-oxadiazole;
2-(4-fluoronaphthalen-1-yl)-5-(pyridin-3-yl)-1,3,4-oxadiazole;
N,N-diethyl-4-(5-(pyridin-3-yl)-1,3,4-oxadiazol-2-yl) aniline;
2-(4-butoxyphenyl)-5-(pyridin-3-yl)-1,3,4-oxadiazole;
2-(2-methoxy-4-(methylthio)phenyl)-5-(pyridin-3-yl)-1,3,4-oxadiazole;
2-(4-(methylsulfonyl)phenyl)-5-(pyridin-3-yl)-1,3,4-oxadiazole;
2-(2-chloro-5-(methylthio)phenyl)-5-(pyridin-3-yl)-1,3,4-oxadiazole;
2-(2-fluoro-5-(trifluoromethyl)phenyl)-5-(pyridin-3-yl)-1,3,4-oxadiazole;
2-(2-chloro-5-(trifluoromethyl)phenyl)-5-(pyridin-3-yl)-1,3,4-oxadiazole;
2-(2-phenethylphenyl)-5-(pyridin-3-yl)-1,3,4-oxadiazole;
2-(2-bromo-5-methoxyphenyl)-5-(pyridin-3-yl)-1,3,4-oxadiazole;
2-(5-bromo-2-chlorophenyl)-5-(pyridin-3-yl)-1,3,4-oxadiazole;
2-(2-iodophenyl)-5-(pyridin-3-yl)-1,3,4-oxadiazole;
2-(3-iodophenyl)-5-(pyridin-3-yl)-1,3,4-oxadiazole;
2-(4-iodophenyl)-5-(pyridin-3-yl)-1,3,4-oxadiazole;
2-(pyridin-3-yl)-5-(pyrimidin-5-yl)-1,3,4-oxadiazole;
2-(5-methylpyrazin-2-yl)-5-(pyridin-3-yl)-1,3,4-oxadiazole;
2-(2-chloro-6-methylpyridin-3-yl)-5-(pyridin-3-yl)-1,3,4-oxadiazole;
2-(2-methyl-6-(trifluoromethyl)pyridin-3-yl)-5-(pyridin-3-yl)-1,3,4-oxadiazole;
2-(2-(ethylthio)pyridin-3-yl)-5-(pyridin-3-yl)-1,3,4-oxadiazole;
2-(2,6-dimethoxypyridin-3-yl)-5-(pyridin-3-yl)-1,3,4-oxadiazole;
2-(2-(methylthio)pyridin-3-yl)-5-(pyridin-3-yl)-1,3,4-oxadiazole;
5-chloro-3-(5-(pyridin-3-yl)-1,3,4-oxadiazol-2-yl)pyridin-2-ol;
2-(2,6-dichloro-5-fluoropyridin-3-yl)-5-(pyridin-3-yl)-1,3,4-oxadiazole;
2-(2,5-dichloropyridin-3-yl)-5-(pyridin-3-yl)-1,3,4-oxadiazole;
2-(6-chloropyridin-3-yl)-5-(pyridin-3-yl)-1,3,4-oxadiazole;
2-(2,6-dichloropyridin-3-yl)-5-(pyridin-3-yl)-1,3,4-oxadiazole;
2-chloropyridin-3-yl)-5-(pyridin-3-yl)-1,3,4-oxadiazole;
2-(pyridin-3-yl)-5-(quinolin-3-yl)-1,3,4-oxadiazole; and
2-(2,2-difluorobenzo[d][1,3]dioxol-5-yl)-5-(pyridin-3-yl)-1,3,4-oxadiazole;
or pharmaceutically acceptable salts thereof.

Novel α4β2 PAMs of the Present Invention

Various embodiments of the invention described herein include, but are not limited to, pharmaceutically acceptable salts, amides, esters and prodrugs thereof.

Another embodiment of the invention is a compound of formula (II), wherein $Ar^2$ and $Ar^3$ are independently aryl, pyrazinyl, pyridazinyl, pyrimidinyl, triazinyl, or a bicyclic heteroaryl, substituted independently with 0, 1, 2, 3, or 4 substitutents selected from the group consisting of alkoxy, alkoxycarbonyl, alkoxycarbonylamino, alkoxycarbonylaminoalkyl, alkyl, alkylamino, alkylcarbonyl, alkylsulfonyl, amido, amino, aminoalkyl, carboxy, dialkylamino, dialkylaminoalkyl, halo, haloalkyl, haloalkylcarbonyl, heteroaryl, heterocycle, hydroxy, hydroxyalkyl, cyano, nitro, oxo, sulfonamide and dialkylsulfonylformimidamide; provided that when one of $Ar^2$ and $Ar^3$ is pyridinyl or aryl, the other is not pyridinyl; when $Ar^3$ is pyridinyl, $Ar^2$ is not pyrazinyl.

Another embodiment of the invention is a compound of formula (II), wherein $Ar^2$ is optionally substituted phenyl.

Another embodiment of the invention is a compound of formula (II), wherein $Ar^2$ is optionally substituted pyridinyl or pyrimidinyl.

Another embodiment of the invention is a compound of formula (II), wherein $Ar^2$ is optionally substituted bicyclic heteroaryl.

Another embodiment of the invention is a compound of formula (II), wherein $Ar^3$ is optionally substituted pyridinyl, pyrimidinyl or pyridazinyl.

Another embodiment of the invention is a compound of formula (II), wherein $Ar^3$ is optionally substituted bicyclic heteroaryl.

Another embodiment of the invention is a compound of formula (II), wherein $Ar^2$ and $Ar^3$ are independently, optionally substituted monocyclic or bicyclic heteroaryl, wherein the monocyclic heteroaryl is six-membered heterocycle, provided that when one of $Ar^2$ and $Ar^3$ is pyridinyl, the other is not pyridinyl, and when $Ar^3$ is pyridinyl, $Ar^2$ is not pyrazinyl.

Another embodiment of the invention is a compound of formula (II), wherein $Ar^2$ and $Ar^3$ are independently, optionally substituted pyrazinyl, pyridazinyl, pyridinyl, pyrimidinyl, triazinyl, or a bicyclic heteroaryl.

Another embodiment of the invention is a compound of formula (II), wherein $Ar^2$ and $Ar^3$ are independently, optionally substituted phenyl, pyridazinyl, pyridinyl, pyrimidinyl, or bicyclic heteroaryl.

Another embodiment of the invention is a compound of formula (II), wherein one of $Ar^2$ and $Ar^3$ is optionally substituted bicyclic heteroaryl.

Another embodiment of the invention is a compound of formula (II), wherein one of $Ar^2$ and $Ar^3$ is optionally substituted bicyclic heteroaryl selected from the group consisting of benzimidazolyl, benzo[d][1,3]dioxolyl, benzofuranyl, benzo[d]imidazolyl, benzooxazole, benzo[d][1,2,3]thiadiazolyl, 1,3-benzothiazolyl, benzo[d][1,2,3]triazolyl, 2,2-difluorobenzo[d][1,3]dioxolyl, imidazopyridinyl, indolyl, indazolyl, pyrazolopyrimidinyl, pyrrolopyridinyl, and [1,2,4]triazolopyridinyl.

Another embodiment of the invention is a compound of formula (II), selected from the group of compounds exemplified in Examples 79-134 described below.

Another embodiment of the invention is a compound of formula (II), selected from the group of compounds exemplified in Examples 79-105 described below.

Another embodiment of the invention is a compound of formula (II), selected from the group of compounds exemplified in Examples 79-82, 85-89, 101, and 103-105 described below.

Another embodiment of the invention is a compound of formula (II), selected from the group of compounds exemplified in Examples 90 and 102 described below.

Another embodiment of the invention is a compound of formula (II), selected from the group of compounds exemplified in Examples 83-84 and 92-100 described below.

Another embodiment of the invention is a compound of formula (II), selected from the group of compounds exemplified in Examples 90-91 described below.

Another embodiment of the invention is a compound of formula (II), selected from the group of compounds exemplified in Examples 106-134 described below.

Another embodiment of the invention is a compound of formula (II), selected from the group of compounds exemplified in Examples 106-118, 123-131 and 134 described below.

Another embodiment of the invention is a compound of formula (II), selected from the group of compounds exemplified in Examples 119-122 and 132-133 described below.

Another embodiment of the invention is 5-(2,3-difluorophenyl)-3-(pyrimidin-5-yl)-1,2,4-oxadiazole.

Another embodiment of the invention is 5-(pyridin-3-yl)-3-(pyrimidin-5-yl)-1,2,4-oxadiazole.

Another embodiment of the invention is 2-fluoro-N,N-dimethyl-4-(3-(pyrimidin-5-yl)-1,2,4-oxadiazol-5-yl)aniline.

Another embodiment of the invention is 3-(3-(pyrimidin-5-yl)-1,2,4-oxadiazol-5-yl)benzonitrile.

Another embodiment of the invention is 5-(3,4-difluorophenyl)-3-(pyridazin-4-yl)-1,2,4-oxadiazole.

Another embodiment of the invention is 3-(pyridazin-4-yl)-5-(pyridin-3-yl)-1,2,4-oxadiazole.

Another embodiment of the invention is N,N-dimethyl-N'-(4-(3-(pyrimidin-5-yl)-1,2,4-oxadiazol-5-yl)phenylsulfonyl)-formimidamide.

Another embodiment of the invention is 5-(4-fluorophenyl)-3-(pyrimidin-5-yl)-1,2,4-oxadiazole.

Another embodiment of the invention is 5-(3-fluorophenyl)-3-(pyrimidin-5-yl)-1,2,4-oxadiazole.

Another embodiment of the invention is 3-(pyrimidin-5-yl)-5-(3,4,5-trifluorophenyl)-1,2,4-oxadiazole.

Another embodiment of the invention is 5-(2-chloropyridin-4-yl)-3-(pyrimidin-5-yl)-1,2,4-oxadiazole.

Another embodiment of the invention is 3-(3-(pyridazin-4-yl)-1,2,4-oxadiazol-5-yl)benzonitrile.

Another embodiment of the invention is 5-(3-fluorophenyl)-3-(pyridazin-4-yl)-1,2,4-oxadiazole.

Another embodiment of the invention is 3-(pyridazin-4-yl)-5-(3,4,5-trifluorophenyl)-1,2,4-oxadiazole.

Another embodiment of the invention is 5-(3,5-difluorophenyl)-3-(pyridazin-4-yl)-1,2,4-oxadiazole.

Another embodiment of the invention is 5-(4-fluorophenyl)-3-(pyridazin-4-yl)-1,2,4-oxadiazole.

Another embodiment of the invention is 3-(pyridazin-4-yl)-5-(pyrimidin-5-yl)-1,2,4-oxadiazole.

Another embodiment of the invention is 3-(pyridazin-4-yl)-5-(2,3,6-trifluorophenyl)-1,2,4-oxadiazole.

Another embodiment of the invention is 3-(pyridazin-4-yl)-5-(2,3,4-trifluorophenyl)-1,2,4-oxadiazole.

Another embodiment of the invention is N,N-dimethyl-N'-(4-(3-(pyridazin-4-yl)-1,2,4-oxadiazol-5-yl)phenylsulfonyl)formimidamide.

Another embodiment of the invention is 5-(3,4-difluorophenyl)-3-(pyrimidin-5-yl)-1,2,4-oxadiazole.

Another embodiment of the invention is 3-(3,4-difluorophenyl)-5-(pyrimidin-5-yl)-1,2,4-oxadiazole.

Another embodiment of the invention is 3-(pyrimidin-5-yl)-5-(2,3,4-trifluorophenyl)-1,2,4-oxadiazole.

Another embodiment of the invention is 3-(pyrimidin-5-yl)-5-(2,3,6-trifluorophenyl)-1,2,4-oxadiazole.

Another embodiment of the invention is 3-(pyrimidin-5-yl)-5-(2,3,4,5-tetrafluorophenyl)-1,2,4-oxadiazole.

Another embodiment of the invention is 3-(pyrimidin-5-yl)-5-(2,3,6-trifluorophenyl)-1,2,4-oxadiazole.

Another embodiment of the invention is 3-(pyrimidin-5-yl)-5-(2,3,4,5-tetrafluorophenyl)-1,2,4-oxadiazole.

Another embodiment of the invention is 5-(imidazo[1,5-a]pyridin-6-yl)-3-(pyridin-3-yl)-1,2,4-oxadiazole.

Another embodiment of the invention is 5-(1H-indol-6-yl)-3-(pyridin-3-yl)-1,2,4-oxadiazole.

Another embodiment of the invention is 5-(2,7-dimethylpyrazolo[1,5-a]pyrimidin-6-yl)-3-(pyridin-3-yl)-1,2,4-oxadiazole.

Another embodiment of the invention is 5-(2,2-difluorobenzo[d][1,3]dioxol-5-yl)-3-(pyridin-3-yl)-1,2,4-oxadiazole.

Another embodiment of the invention is 5-(2-methylbenzofuran-5-yl)-3-(pyridin-3-yl)-1,2,4-oxadiazole.

Another embodiment of the invention is 5-(benzo[d][1,2,3]thiadiazol-5-yl)-3-(pyridin-3-yl)-1,2,4-oxadiazole.

Another embodiment of the invention is 5-(1H-benzo[d]imidazol-5-yl)-3-(pyridin-3-yl)-1,2,4-oxadiazole.

Another embodiment of the invention is 5-(1H-benzo[d][1,2,3]triazol-5-yl)-3-(pyridin-3-yl)-1,2,4-oxadiazole.

Another embodiment of the invention is 5-(benzo[d]thiazol-5-yl)-3-(pyridin-3-yl)-1,2,4-oxadiazole.

Another embodiment of the invention is 3-(pyridin-3-yl)-5-(1H-pyrrolo[2,3-b]pyridin-5-yl)-1,2,4-oxadiazole.

Another embodiment of the invention is 5-(1H-indol-5-yl)-3-(pyridin-3-yl)-1,2,4-oxadiazole.

Another embodiment of the invention is 5-(benzofuran-5-yl)-3-(pyridin-3-yl)-1,2,4-oxadiazole.

Another embodiment of the invention is 5-(1-methyl-1H-benzo[d]imidazol-5-yl)-3-(pyridin-3-yl)-1,2,4-oxadiazole.

Another embodiment of the invention is 3-(imidazo[1,2-a]pyridin-6-yl)-5-(pyridin-3-yl)-1,2,4-oxadiazole.

Another embodiment of the invention is 5-(6-chloropyridin-3-yl)-3-(imidazo[1,2-a]pyridin-6-yl)-1,2,4-oxadiazole.

Another embodiment of the invention is 5-(6-fluoropyridin-3-yl)-3-(imidazo[1,2-a]pyridin-6-yl)-1,2,4-oxadiazole.

Another embodiment of the invention is 5-(5-fluoropyridin-3-yl)-3-(imidazo[1,2-a]pyridin-6-yl)-1,2,4-oxadiazole.

Another embodiment of the invention is 5-(1H-indazol-5-yl)-3-(pyridin-3-yl)-1,2,4-oxadiazole.

Another embodiment of the invention is 5-([1,2,4]triazolo[4,3-a]pyridin-6-yl)-3-(pyridin-3-yl)-1,2,4-oxadiazole.

Another embodiment of the invention is 5-(3-(pyridin-3-yl)-1,2,4-oxadiazol-5-yl)benzo[d]oxazol-2(3H)-one.

Another embodiment of the invention is 5-(3-(pyridin-3-yl)-1,2,4-oxadiazol-5-yl)-1H-benzo[d]imidazole-2(3H)-thione.

Another embodiment of the invention is 1,3-dimethyl-5-(3-(pyridin-3-yl)-1,2,4-oxadiazol-5-yl)-1H-benzo[d]imidazol-2(3H)-one.

Another embodiment of the invention is 6-(3-(pyridin-3-yl)-1,2,4-oxadiazol-5-yl)benzo[d]oxazol-2(3H)-one.

Another embodiment of the invention is 5-(3-(pyridin-3-yl)-1,2,4-oxadiazol-5-yl)-1H-benzo[d]imidazol-2(3H)-one.

Another embodiment of the invention is 6-(3-(Pyridin-3-yl)-1,2,4-oxadiazol-5-yl)benzo[d]oxazol-2-amine.

Another embodiment of the invention is 6-(3-(pyridin-3-yl)-1,2,4-oxadiazol-5-yl)benzo[d]oxazole.

Another embodiment of the invention is 5-(5-(pyridin-3-yl)-1,2,4-oxadiazol-3-yl)benzo[d]oxazol-2(3H)-one.

Another embodiment of the invention is 5-(5-(6-chloropyridin-3-yl)-1,2,4-oxadiazol-3-yl)benzo[d]oxazol-2(3H)-one.

Another embodiment of the invention is 5-(benzo[d][1,3]dioxol-5-yl)-3-(pyridin-3-yl)-1,2,4-oxadiazole.

Another embodiment of the invention is 3-(Pyridin-3-yl)-5-(pyrimidin-5-yl)-1,2,4-oxadiazole.

Another embodiment of the invention is 5-(Pyridazin-4-yl)-3-(pyridin-3-yl)-1,2,4-oxadiazole.

Another embodiment of the invention is 3-(3,4-difluorophenyl)-5-(pyrimidin-5-yl)-1,2,4-oxadiazole.

Compound names are assigned by using Struct=Name naming algorithm, which is part of the CHEMDRAW® ULTRA v. 9.0.7 software suite.

Geometric isomers can exist in the present compounds. The invention contemplates the various geometric isomers and mixtures thereof resulting from the disposition of substituents around a carbon-carbon double bond, a carbon nitrogen double bond, a cycloalkyl group, or a heterocycloalkyl group. Substituents around a carbon-carbon or carbon-nitrogen double bond are designated as being of Z or E configuration and substituents around a cycloalkyl or heterocycloalkyl are designated as being of cis or trans configuration.

Within the present invention it is to be understood that compounds disclosed herein can exhibit the phenomenon of tautomerism. Thus, when the formulae drawings within this specification represent one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or formulae drawings.

Preparation of Compounds

Preparation of Compounds Suitable for the Composition of the Invention can be understood in connection with the following synthetic schemes and examples, which illustrate a means by which the compounds can be prepared. Methods for preparing suitable nicotinic acetylcholine receptor ligands and suitable nicotinic acetylcholine subtype α4β2 allosteric modulators are readily available in the literature. Suitable compounds can be prepared by conventional methods for chemical synthesis with readily available starting materials. Nicotinic acetylcholine receptor ligands and nicotinic acetylcholine subtype α4β2 allosteric modulators also may be commercially available.

Abbreviations which have been used in the descriptions of the schemes and the examples that follow are: butyllithium (BuLi), N-(3-dimethylaminopropyl)-N'-ethylcarbodiimide hydrochloride (EDC), ethyl acetate (EtOAc), ethanol (EtOH), 1-hydroxybenzotriazole (HOBT), high-pressure liquid chromatography (HPLC), tetrahydrofuran (THF), triethylamine (NEt₃ or Et₃N), triphenylphosphine (PPh₃), polymer-supported triphenylphosphine (PS-PPh₃), methanol (MeOH), dimethylsulfoxide (DMSO), trifluoroacetic acid (TFA), palladium acetate (Pd(OAc)₂), acetate (OAc), tris (dibenzylidineacetone) palladium (0) (Pd₂(dba)₃), 1,1'-Bis (diphenylphosphino)ferrocene]dichloropalladium(II) (PdCl₂ (dppf)), Dulbecco's Modified Eagle's Medium (DMEM), fetal bovine serum (FBS), N-methyl-D-glucamine (NMDG), and 4-(2-hydroxyethyl)-1-piperazineethanesulfonic acid (HEPES).

Oxadiazole derivatives suitable for the composition of the invention can be prepared according to conventional methods. Some suitable methods for preparing such oxadiazole derivatives are provided in the Schemes and Examples below. However, such further illustration is intended only for reference and is not intended in any way to limit the scope of the invention.

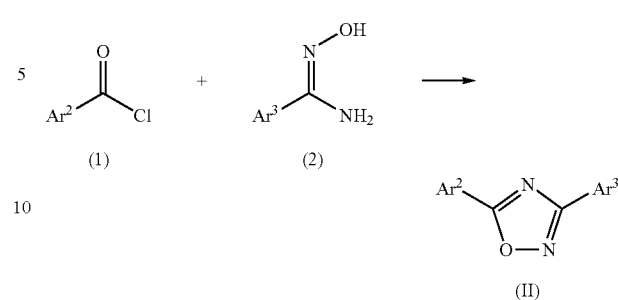

As shown in Scheme 1, compounds of formula (II), wherein Ar² and Ar³, are as defined in formula (II) above, can be prepared as described in Scheme 1. Aryl or heteroaryl compounds of general formula (1), can be treated with formula (2) with heat in a solvent including, but not limited to pyridine, to provide of general formula (II).

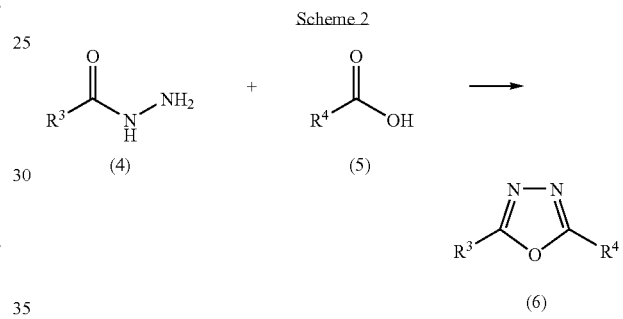

As shown in Scheme 2, compounds of formula (4) can be reacted with compounds of formula (5) in POCl₃ at temperatures from 40-100° C. over 1-24 hours to provide compounds of formula (6); wherein R³ is Ar¹ and R⁴ is Y, or R³ is Y and R⁴ is Ar¹. Alternatively, compounds of formula (4) can be reacted with compounds of formula (5) in the presence of triphenylphosphine, which may optionally be polymer bound, and trichloroacetonitrile in acetonitrile. The mixture may be heated in a microwave oven at 100-175° C. for 5-30 minutes as described by Wang, Y.; Sauer, D. R.; Djuric, S. W. Tetrahedron. Lett. 2006, 47, 105-108. Another alternative includes combining compounds of formula (4) and compounds of formula (5) in a solvent such as methylene chloride in the presence of 2-chloro-1,3-dimethylimidazolinium chloride and a base such as triethylamine at 15-35° C. for 10-120 hours as described by Isobe, T.; Ishikawa, T. J. Org. Chem. 1999, 64, 6989-6992.

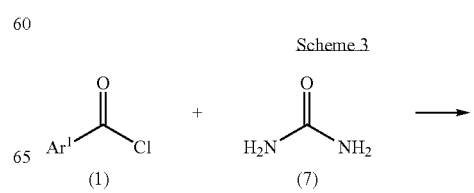

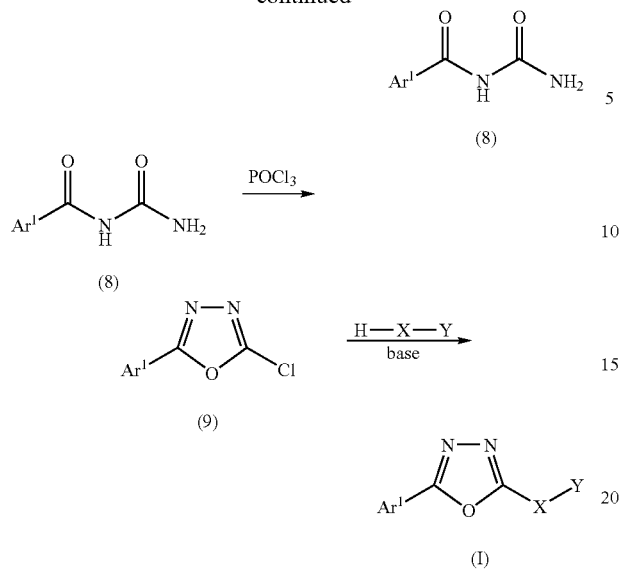

As shown in Scheme 3, compounds of formula (1) can be reacted with urea (7) in a solvent such as dichloromethane in the presence of a base such as triethylamine at 25-40° C. for 1-12 hours to provide compounds of formula (8) as described in Sobol, E.; Bialer, M.; Yagen, B. J. Med. Chem. 2004, 47, 4316-4326. Alternatively, compounds of formula (1) and (7) may be combined in pyridine at 20-110° C. for 1-24 hours to provide compounds of formula (8). Compounds of formula (8) can be treated with POCl$_3$ at 25-100° C. for 1-24 hours to provide compounds of formula (9). Compounds of formula (9) can be reacted with H—X—Y in the presence of a base such as lithium bis(trimethylsilyl)amide, sodium bis(trimethylsilyl)amide, potassium bis(trimethylsilyl)amide, potassium t-butoxide, sodium hydride, potassium carbonate, sodium carbonate, cesium or carbonate in a solvent such as tetrahydrofuran, 1-methyl-2-pyrrolidinone, dimethyl sulfoxide, or acetonitrile at temperatures from −20° C. to 150° C. over 1-48 hours to provide compounds of formula (I).

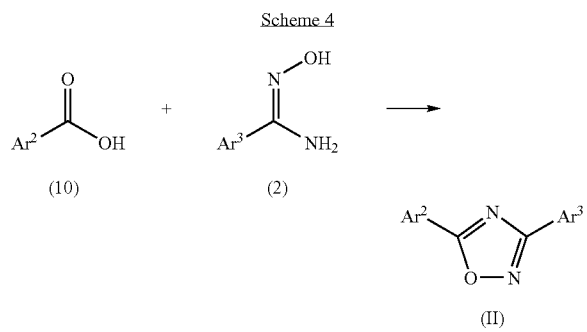

As shown in Scheme 4, compounds of formula (II), wherein Ar$^2$ and Ar$^3$, are as defined in formula (II), can be prepared as described in Scheme 4. Aryl or heteroaryl compounds of general formula (10), can be treated with compounds of formula (2) in the presence of a coupling agent such as N-(3-methylaminopropyl)-N'-ethylcarbodiimide hydrochloride and 1-hydroxybenzotriazole with heat in a solvent including, but not limited to dimethylformamide, to provide compounds of general formula (II).

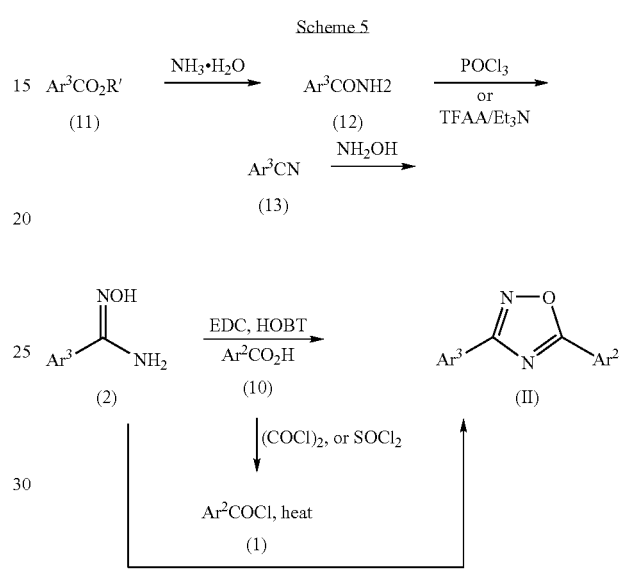

As shown in Scheme 5, compounds of formula (II), wherein Ar$^2$ and Ar$^3$, are as previously defined, can be prepared as described in Scheme 5. Compounds of formula (13), which can be either obtained from a commercial source or prepared from compounds of formula (11). Amides of formula (12) can be prepared by reacting compounds of formula (11) with ammonium hydroxide. Subsequent dehydration of compound of formula (12) with a dehydrating agent, such as but not limited to phosphorous oxychloride or trifluoroacetic anhydride (TFAA)/triethylamine provide compounds of formula (13). Compounds of formula (13) can be reacted with hydroxylamine to give compounds of formula (2). Compounds of formula (2) react with an aromatic carboxylic acids of formula (10) in the presence of a coupling agent, such as but not limited to N-(3-dimethylaminopropyl)-N'-ethylcarbodiimide hydrochloride (EDC)/1-hydroxybenzotriazole (HOBT), in dimethylformamide at 80-120° C. to give compounds of formula (II). Alternatively, compounds of formula (II) can also be prepared by heating a mixture of compounds of formula (2) and compound of formula (1) which can be obtained from either a commercial source or by the treatment of compound of formula (10) with a chlorinating agent, such as oxalyl chloride or thionyl chloride, in a solvent such as but not limited to pyridine or THF at 60-110° C.

Scheme 6

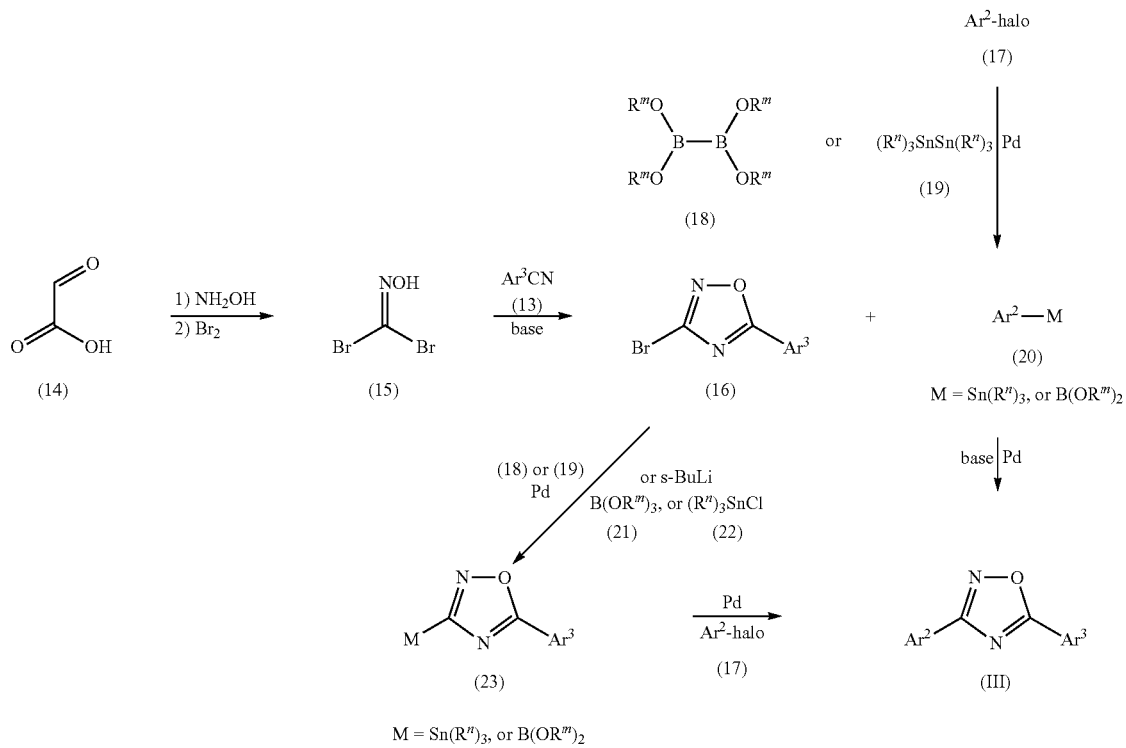

Compounds of formula (III), wherein Ar² and Ar³ are as defined in formulas (II), can be prepared as described in Scheme 6. Compounds of formula (14) can be first reacted with hydroxylamine at ambient temperature and then treated with bromine in dichloromethane at temperatures from 0-20° C. to provide compounds of formula (15) as described by Berrier, J. V. and Umarvadia, A. S. in EP0979814. The compounds of formula (15) reacts with compounds of formula (13) in the presence a base, such as but not limited to triethylamine, Na₂CO₃ and K₂CO₃, in a solvent, such as toluene, at temperature ranging 80-110° C. over 10-40 hours to provide compounds of formula (16) as described by Humphrey, G. R.; Wright, S. H. B. in *J. Heterocyclic Chem*. (1989, 26, 23-24). Compounds of formula (17), wherein halo is chloro, bromo or iodo, when treated with an organoboranes of formula (18) or ditin compounds of formulas (19), such as bis(pinacolato) diboron or hexmethlyditin, respectively, wherein R'" or R" are hydrogen, alkyl or aryl, in the presence of a palladium catalyst, such as, but not limited to Pd(OAc)₂, PdCl₂(PPh₃)₂, Pd(PPh₃)₄, PdCl₂(dppf), Pd₂(dba)₃ provide the corresponding tin or boronic acid or boronic esters of formula (20), wherein M is —Sn—(R")₃ or —B(OR'")₂. Compounds of formula (16) can be reacted with compounds of formula (20) in the presence of a palladium catalyst, such as, but not limited to Pd(OAc)₂, PdCl₂(PPh₃)₂, Pd(PPh₃)₄, PdCl₂(dppf), Pd₂(dba)₃, and a base, such as but not limited to CsF, Na₂CO₃, K₂CO₃ and K₃PO₄, will provide compounds of formula (III). Alternatively, compounds of formula (16) when treated with organoboranes of formula (18) or ditin compounds of formulas (19), such as bis(pinacolato)diboron or hexmethlyditin, respectively, in the presence of a palladium catalyst provide organotin compounds, organoboronic acids or organoboronic esters compounds of formula (23), wherein M is —Sn—(R")₃ or —B(OR'")₂. Compounds of formula (23) can also be prepared by the initial treatment of compounds of formula (16) with s-BuLi at temperature ranging from –90° C. to –60° C. and then reaction with a boronic ester of formula (21) or an organotin compound of formula (22). Compounds of formula (23) can be reacted with compounds of formula (17) in the presence of a palladium catalyst, such as, but not limited to Pd(OAc)₂, PdCl₂(PPh₃)₂, Pd(PPh₃)₄, PdCl₂(dppf), Pd₂(dba)₃, and a base, such as but not limited to CsF, Na₂CO₃, K₂CO₃ and K₃PO₄ to provide compounds of formula (III).

Scheme 7

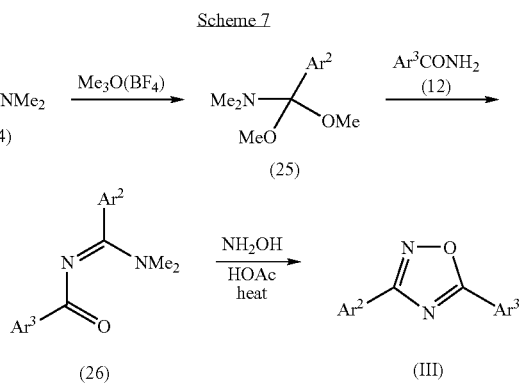

The compounds of formula (III), wherein Ar² and Ar³ are as previously defined can be prepared as shown in Scheme 7. Compounds of formula (24), where in Ar² is defined in formulas (II) and (III), when treated with trimethyloxonium tetrafluoroborate in dichloromethane provide compounds of formula (25) as described by McClelland, R. A. in *J. Am.*

Chem. Soc. (1978, 100, 1844-1849). Compounds of formula (25) can be reacted with compounds of formula (12), wherein $Ar^3$ is defined in formulas (II) and (III), at temperature ranging from 80-140° C. over 1-6 hours to give compounds of formula (26). Compounds of formula (26) react with hydroxylamine in acetic acid at room temperature to 90° C. to provide the compounds of formula (III) as described by Lin, Y.-I., et al., *J. Org. Chem.*, 44, 4160-4164, 1979.

In addition, compounds of formula (II) and (III), wherein at least one of $Ar^1$ and $Ar^2$ is a N-containing heteroaryl, can be converted to compounds with $N^+$—$O^-$ by treatment with an oxidizing agent. Examples of the oxidizing agent include, but are not limited to aqueous hydrogen peroxide and m-chloroperbenzoic acid. The reaction is generally performed in a solvent such as, but not limited to acetonitrile, water, dichloromethane, acetone or a mixture thereof, preferably a mixture of acetonitrile and water, at a temperature from about 0° C. to about 80° C., for a period of about 1 hour to about 4 days.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss et al., pub. Longman Scientific & Technical, Essex CM20 2JE, England.

Compounds and processes suitable for preparing compounds for the composition of the invention will be better understood in connection with the following Examples, which are intended as an illustration of and not a limitation upon the scope of the invention.

Preparation of 2,5-Disubstituted-1,3,4-Oxadiazole Derivatives

Suitable 2,5-disubstituted-1,3,4-oxadiazole derivatives were prepared using readily available starting materials. For example, International Publication WO 02/100826, published Dec. 19, 2002, describes the preparation of some oxadiazole derivatives. However, Compounds of formula (I) also can be prepared according to the following general methods.

Method A: A carboxylic acid (0.5 mmol) and an acyl hydrazide (0.5 mmol) were combined in $POCl_3$ (2 mL) and stirred at 80-90° C. for 2-4 hours. The reaction mixture was then cooled down to ambient temperature and poured into ice water (10-20 g) and basified with saturated aqueous sodium carbonate to pH=8-9. The resultant precipitate was filtered, dried and purified with chromatography on silica gel to provide the corresponding 2,5-disubstituted-1,3,4-oxadiazole. The free base was then dissolved in EtOAc (5-10 mL) and treated with HCl (Aldrich, 4 M in dioxane, 2-3 eq.) at ambient temperature for 5-10 hours. The precipitate was filtered and dried to provide the corresponding 2,5-disubstituted-1,3,4-oxadiazole hydrochloric acid salt.

Method B: A Smith Process vial (0.5-2 ml) was charged with a stir bar. To the vessel were added a carboxylic acid (0.1 mmol), nicotinic hydrazide (Aldrich, 13.7 mg, 0.1 mmol), PS-$PPh_3$ (Fluka, 2.2 mmol/g, 136 mg, 0.3 mmol) and Acetonitrile (anhydrous, Aldrich, 2 mL), followed by $CCl_3CN$ (Aldrich, 28.8 mg, 0.20 mmol). The reaction vessel was sealed and heated to 150° C. for 15 minutes using an Emrys™ Optimizer Microwave (Personal Chemistry). After cooling, the reaction vessel was uncapped and the resin was removed by filtration. The mixture was purified by preparative HPLC [Waters, column: Nova-Pak® HR C18 6 µm 60 Å Prep-Pak® (25 mm×100 mm), solvent: acetonitrile/water (v. 1% TFA), 5/95 to 95/5, flow rate of 40 mL/minute. Fractions were collected based upon UV signal threshold, and selected fractions were subsequently analyzed by flow injection analysis mass spectrometry using positive APCI ionization on a Finnigan LCQ using 70:30 methanol:10 mM $NH_4OH$(aq) at a flow rate of 0.8 mL/minute.]. Some mixtures were purified by an alternative preparative HPLC method [Waters, column: Sunfire OBD C8 5 µm (30 mm×75 mm); solvent: acetonitrile/10 mM aqueous ammonium acetate, 10/90 to 100/0; flow rate of 50 mL/minute]. Fractions were collected based upon target mass signal threshold, and selected fractions were subsequently analyzed by flow injection analysis mass spectrometry using the previously described method.

Preparation of 2,5-Disubstituted-1,24-Oxadiazole Derivatives

Suitable 2,5-disubstituted-1,2,4-oxadiazole derivatives were prepared using readily available starting materials. For example, International Publication WO 02/100826, published Dec. 19, 2002, describes the preparation of some oxadiazole derivatives. However, compounds of formula (II) and (III) also can be prepared according to the following general methods.

Method C: To a solution of an aryl or heteroaryl carboxylic acid (1.0 mmol) in dimethylformamide (anhydrous, 5 mL) was added N-(3-dimethylaminopropyl)-N'-ethylcarbodiimide hydrochloride (EDC) (Aldrich, 192 mg, 1.00 mmol) and 1-hydroxybenzotriazole (HOBt) hydrate (Fluka, 153 mg, 1.00 mmol). The mixture was stirred at ambient temperature for 20 minutes. N'-Hydroxy aryl or heteroaryl carboximidamide (1.0 mmol) was added and the mixture was stirred for 6-10 hours, and then warmed to 140° C. for 2-4 hours. The reaction was cooled to ambient temperature and triturated with water (10 mL). The precipitate was filtered and dried under vacuum to give the titled compound. When the reaction mixture failed to give a precipitate, the reaction mixture was extracted with EtOAc (3×30 mL). The combined extracts were concentrated and the residue was purified with chromatography ($SiO_2$, hexane/EtOAc) or preparative HPLC [Waters, column: Xbridge™ Prep C18 5 µm, OBD™ 30×100 mm, solvent: acetonitrile/water (pH=10, prepared with $NH_4HCO_3/NH_3.H_2O$) or acetonitrile/water (v/v 0.1% TFA), 5/95 to 95/5, flow rate of 40 mL/minute. Fractions were collected based upon UV signal threshold.].

Method D: To a solution of N'-Hydroxy aryl or heteroaryl carboximidamide (1.0 mmol) in pyridine (5 mL) was added an aryl or heteroaryl carbonyl chloride (1.0 mmol). The mixture was then stirred at the temperature ranging from 80-100° C. for 2-10 hours. The reaction was cooled to ambient temperature and triturated with water (10 mL). The precipitate was filtered and dried under vacuum to give the titled compound. When the reaction mixture failed to give a precipitate, the reaction mixture was extracted with EtOAc (3×30 mL). The combined extracts were concentrated and the residue was purified with chromatography ($SiO_2$, hexane/EtOAc) or preparative HPLC [Waters, column: Xbridge™ Prep C18 5 µm, OBD™ 30×100 mm, solvent: acetonitrile/water (pH=10) or acetonitrile/water (v/v 0.1% TFA), 5/95 to 95/5, flow rate of 40 mL/minute. Fractions were collected based upon UV signal threshold.].

EXAMPLE 1

3-(3-(pyridin-3-yl)-1,2,4-oxadiazol-5-yl)benzonitrile

3-Pyridylamideoxime (Aldrich, 5.5 g, 40 mmol) was dissolved in 60 mL of pyridine and 3-cyanobenzoyl chloride (Aldrich, 6.6 g, 40 mmol) was added. The reaction mixture was heated to reflux for 4 hours and then cooled to room temperature. The solution was poured into water (500 mL), filtered, and the solid were collected and dried under vacuum. $^1$H NMR (300 MHz, CD$_3$OD) δ ppm 7.87 (td, J=8.0, 0.7 Hz, 1 H), 8.10 (dt, J=8.1, 1.4 Hz, 1 H), 8.23 (ddd, J=8.1, 5.6, 0.8 Hz, 1 H), 8.56 (ddd, J=8.0, 1.7, 1.2 Hz, 1 H), 8.64 (td, J=1.7, 0.7 Hz, 1 H), 9.04 (dd, J=5.4, 1.0 Hz, 1 H), 9.23 (dt, J=8.1, 1.7 Hz, 1 H), 9.57 (d, J=1.7 Hz, 1 H); MS (+ESI) m/z 249 (M+H)$^+$.

EXAMPLE 2

3,5-di(pyridin-3-yl)-1,2,4-oxadiazole

3-Pyridylamideoxime (5.5 g, 40 mmol) was dissolved in 60 mL of pyridine and nicotinoyl chloride hydrochloride (7.2 g, 40 mmol) was added. The reaction mixture was heated to reflux for 4 hours and then cooled to room temperature. The solution was poured into water (500 mL), basified, filtered, and the solid was collected and dried under vacuum. $^1$H NMR (300 MHz, DMSO-d$_6$) δ 7.75-7.65 (m, 2H), 8.49-8.45 (m, 1 H), 8.60-8.57 (m, 1 H), 8.84-8.82 (dd, J=1.7 Hz, 1 H), 8.92-8.90 (dd, J=1.7 Hz, 1 H), 9.28 (m, 1 H), 9.37 (m, 1 H) ppm; MS (DCI/NH$_3$) m/z 225 (M+H)$^+$.

EXAMPLE 3

3-(5-(pyridin-3-yl)-1,2,4-oxadiazol-3-yl)benzonitrile

EXAMPLE 3A

3-Cyano-N'-hydroxybenzimidamide

Hydroxylamine (Aldrich, 7.65 g, 100 mmol) in ethanol (100 mL) was treated with 10 N sodium hydroxide (10 mL, 100 mmol). To this solution, isophthalonitrile (Aldrich, 12.8 g, 100 mmol) in 100 mL ethanol was added. The reaction mixture was heated to reflux for 3 hours and then cooled to room temperature. The solvent was removed under vacuum and the residue was purified with flash column chromatography (5% methanol/dichloromethane) to provide the titled compound. $^1$H NMR (300 MHz, DMSO-d$_6$) δ 5.98 (bs, 2 H), 7.59 (t, J=7.4 Hz, 1 H), 8.06-8.0 (m, 2 H), 9.89 (s, 1 H) ppm; MS (DCI/NH$_3$) m/z 162 (M+H)$^+$.

EXAMPLE 3B 3-(5-(pyridin-3-yl)-1,2,4-oxadiazol-3-yl)benzonitrile

3-Cyano-N'-hydroxybenzimidamide (0.322 g, 1 mmol) was dissolved in pyridine (10 mL) and nicotinoyl chloride (Aldrich, 0.141 g, 1 mmol) was added. The reaction mixture was heated to reflux for 3 hours and cooled to room temperature. The cooled reaction mixture was quenched with water (25 mL) and filtered. The solid was further purified with flash column chromatography (5% methanol/dichloromethane) to give the titled compound. $^1$H NMR (300 MHz, DMSO-d$_6$) δ 7.75-7.71 (dd, J=5.7, 4.1 Hz, 1 H), 7.85 (t, J=7.8 Hz, 1 H), 8.15-8.12 (d, J=7.8 Hz, 1 H) 8.44-8.42 (m, 1 H), 8.50 (m, 1 H), 8.60-8.56 (m, 1 H), 8.93-8.91 (dd, J=1.7 Hz, 1 H), 9.37-9.38 (d, J=1.7 Hz, 1 H) ppm; MS (DCI/NH$_3$) m/z 249 (M+H)$^+$.

EXAMPLE 4

3-(5-(6-fluoropyridin-3-yl)-1,2,4-oxadiazol-3-yl)benzonitrile

EXAMPLE 4A

3-Cyano-N'-hydroxybenzimidamide

Hydroxylamine (Aldrich, 7.65 g, 100 mmol) in ethanol (100 mL) was treated with 10 N NaOH (10 mL, 100 mmol). To this solution, isophthalonitrile (Aldrich, 12.8 g, 100 mmol) in 100 mL of ethanol was added. The reaction mixture was heated to reflux for 3 hours and then cooled to room temperature. The solvent was removed under vacuum and the residue was purified with flash column chromatography (5% methanol/dichloromethane) to give the titled product. $^1$H NMR (300 MHz, DMSO-d$_6$) δ 5.98 (bs, 2 H), 7.59 (t, J=7.4 Hz, 1 H), 8.06-8.0 (m, 2 H), 9.89 (s, 1 H) ppm; MS (DCI/NH$_3$) m/z 162 (M+H)$^+$.

EXAMPLE 4B 3-(5-(6-fluoropyridin-3-yl)-1,2,4-oxadiazol-3-yl)benzonitrile

3-Cyano-N'-hydroxybenzimidamide (0.322 g, 1 mmol) was dissolved in pyridine 10 mL and 6-fluoronicotinoyl chloride (Frontier Scientific, 0.160 g, 1 mmol) was added. The reaction mixture was heated to reflux for 3 hours and then cooled to room temperature. The cooled reaction mixture was quenched with water (25 mL) and filtered. The solid was further purified with flash column chromatography (5% methanol/dichloromethane) to give the titled product. $^1$H NMR (300 MHz, DMSO-d$_6$) δ 7.56-7.52 (m, 1 H), 7.85 (t, J=7.9 Hz, 1 H), 8.15-8.12 (m, 1 H), 8.43-8.41 (m, 1 H), 8.49 (m, 1 H), 8.8-8.74 (m, 1 H), 9.11-9.0 (m, 1 H) ppm; MS (DCI/NH$_3$) m/z 267 (M+H)$^+$.

EXAMPLE 5

5-(5-bromopyridin-3-yl)-3-(pyridin-3-yl)-1,2,4-oxadiazole

The title compound was prepared according to the procedure of Example 1 using N'-hydroxynicotinimidamide (Aldrich) and 5-bromonicotinoyl chloride (Alfa). $^1$H NMR (300 MHz, DMSO-d$_6$) δ 8.65-8.69 (m, 1 H), 8.45-8.49 (m, 1 H), 8.79 (t, J=1.7 Hz, 1 H), 8.84 (dd, J=1.7, 2.0 Hz, 1 H), 9.07 (d, J=2 Hz, 1 H), 9.28-9.29 (m, 1 H), 9.34 (d, J=1.7 Hz, 1 H) ppm; MS (DCI/NH$_3$) m/z 303 (M+H)$^+$.

EXAMPLE 6

3-(pyridin-3-yl)-5-(3-(trifluoromethylsulfonyl)phenyl)-1,2,4-oxadiazole

EXAMPLE 6A 3-(trifluoromethylsulfonyl)benzoic acid

A solution of 3-(trifluoromethylthio)benzoic acid (222 mg, 1 mmol) in dichloromethane (10 mL) was stirred with chromium(VI) oxide (Aldrich, 2.0 mmol) at ambient temperature for 12 hours. The title compound was obtained by directly loading the reaction mixture onto a silica gel column and eluting with dichloromethane/methanol (9:1). $^1$H NMR (300 MHz, DMSO-d$_6$) δ 8.8 (s, 1 H), 8.28 (m, 1 H), 8.05 (m, 1 H), 7.9 (m, 1 H) ppm; MS (DCI/NH$_3$) m/z 255 (M+H)$^+$.

EXAMPLE 6B 3-(trifluoromethylsulfonyl)benzoyl chloride

A solution of the product of Example 6A (198 mg, 0.8 mmol) in dichloromethane (10 mL) was stirred with oxalyl dichloride (Aldrich, 2.0 mmol) and 1 drop of dimethylformamide at ambient temperature for 2 hours. The title compound was obtained by removing the solvent under vacuum as a yellow oil (250 mg) and the compound was used directly in the next step.

EXAMPLE 6C 3-(pyridin-3-yl)-5-(3-(trifluoromethylsulfonyl)phenyl)-1,2,4-oxadiazole The title compound was prepared according to the procedure of Example 1 using N-hydroxynicotinimidamide (Aldrich) and the compound of Example 6B. $^1$H NMR (300 MHz, DMSO-d$_6$) δ 7.73 (dd, J=4, 5.0 Hz, 1 H), 7.85 (t, J=8 Hz, 1 H), 8.13 (m, 1 H), 8.43 (m, 1 H) 8.5 (m, 1 H), 8.6 (m, 1 H), 8.92 (m, 1 H), 9.37 (m, 1 H) ppm; MS (DCI/NH$_3$) m/z 356 (M+H)$^+$.

EXAMPLE 7

3-(3-(6-methylpyridin-3-yl)-1,2,4-oxadiazol-5-yl)benzonitrile

EXAMPLE 7A

N'-hydroxy-6-methylnicotinimidamide

Hydroxylamine (Aldrich, 0.765 g, 10 mmol) in ethanol (10 mL) was treated with a solution 6-methylnicotinonitrile (Aldrich, 12.8 g, 100 mmol) in ethanol (10 mL). The reaction mixture was heated to reflux for 3 hours and then cooled to room temperature. The solvent was removed under vacuum and the residue was purified with flash column chromatography (5% methanol/dichloromethane) give the titled compound. $^1$H NMR (300 MHz, DMSO-d$_6$) δ 2.2 (s, 3 H), 6.02 (bs, 2 H), 7.59 (m, 1 H), 8.06-8.0 (m, 2 H), 10.2 (s, 1 H) ppm; MS (DCI/NH$_3$) m/z 152 (M+H)$^+$.

EXAMPLE 7B 3-(3-(6-methylpyridin-3-yl)-1,2,4-oxadiazol-5-yl)benzonitrile

The titled compound was prepared according to the procedure of Example 1 using N'-hydroxynicotinimidamide (Example 7A) and 3-cyanobenzoyl chloride (Aldrich). $^1$H NMR (300 MHz, DMSO-d$_6$) δ 2.59 (s, 3H), 7.52 (d, J=8.1 Hz, 1 H), 7.39 (t, J=8.5 Hz, 1 H), 8.23-8.21 (m, 1 H), 8.36-8.32 (m, 1 H), 8.53-8.49 (m, 1 H), 8.64 (m, 1 H), 9.14 (m, 1 H), ppm; MS (DCI/NH$_3$) m/z 263 (M+H)$^+$.

EXAMPLE 8

5-(5-(pyrrol-1-yl)pyridin-3-yl)-3-(pyridin-3-yl)-1,2,4-oxadiazole

To a solution of 5-(1H-pyrrol-1-yl)nicotinic acid (Maybridge, 188 mg, 1.00 mmol) in dimethylformamide (anhydrous, 5 mL) was added N-(3-methylaminopropyl)-N'-ethylcarbodiimide hydrochloride (EDC) (Aldrich, 192 mg, 1.00 mmol) and 1-hydroxybenzotriazole (HOBT) hydrate (Fluka, 153 mg, 1.00 mmol). The mixture was stirred at ambient temperature for 20 minutes. N'-Hydroxynicotinimidamide (137 mg, 1.0 mmol) was added and the mixture was stirred for 6-10 hours, and then warmed to 140° C. for 2-4 hours. The reaction was cooled to ambient temperature and triturated with water (10 mL). The precipitate was filtered and dried under vacuum to give the titled compound. $^1$H NMR (300 MHz, DMSO-d$_6$) δ 6.34-6.44 (m, 2 H), 7.60-7.82 (m, 3 H), 8.50 (dt, J=8.1, 1.9 Hz, 1H), 8.71 (dd, J=2.5, 1.9 Hz, 1 H), 8.84 (dd, J=4.6, 1.5 Hz, 1 H), 9.21 (d, J=1.7 Hz, 1 H), 9.26 (d, J=2.4 Hz, 1 H), 9.31 (d, J=1.7 Hz, 1 H) ppm; MS (DCI/NH3) m/z 290 (M+H)$^+$.

EXAMPLE 9

5-(3-(pyridin-3-yl)-1,2,4-oxadiazol-5-yl)pyridin-3-ol

The title compound was prepared according to the procedure of Example 8 using N'-hydroxynicotinimidamide (Aldrich) and 5-hydroxynicotinic acid (Matrix Scientific). $^1$H NMR (300 MHz, DMSO-d$_6$) δ 7.66 (ddd, J=8.0, 4.9, 1.0 Hz, 1 H), 7.86 (dd, J=2.7, 2.0 Hz, 1 H), 8.31-8.55 (m, 2 H), 8.83 (s, 2 H), 9.26 (s, 1 H) ppm; MS (DCI/NH$_3$) m/z 241 (M+H)$^+$.

EXAMPLE 10

5-(3,4-difluorophenyl)-3-(pyridin-3-yl)-1,2,4-oxadiazole

The title compound was prepared according to the procedure of Example 8 using N'-hydroxynicotinimidamide (Aldrich) and 3,4-difluorobenzoic acid (Aldrich). $^1$H NMR (300 MHz, CD$_3$OD) δ 7.52-7.67 (m, 2 H), 8.12 (ddd, J=8.7, 4.3, 1.5 Hz, 1 H), 8.19 (ddd, J=10.8, 7.5, 2.0 Hz, 1 H), 8.55 (dt, J=8.1, 1.9 Hz, 1 H), 8.74 (dd, J=5.1, 1.7 Hz, 1 H), 9.29 (dd, J=2.0, 0.7 Hz, 1 H) ppm; MS (DCI/NH$_3$) m/z 260 (M+H)$^+$.

EXAMPLE 11

5-(2,3-difluorophenyl)-3-(pyridin-3-yl)-1,2,4-oxadiazole

The title compound was prepared according to the procedure of Example 8 using N'-hydroxynicotinimidamide (Aldrich) and 2,3-difluorobenzoic acid (Aldrich). $^1$H NMR (300 MHz, CD$_3$OD) δ 7.51-7.67 (m, 2 H), 8.08-8.14 (m, 1 H), 8.18 (ddd, J=10.7, 7.5, 2.0 Hz, 1 H), 8.55 (dt, J=8.0, 1.9 Hz, 1 H), 8.74 (dd, J=5.2, 1.6 Hz, 1 H), 9.29 (dd, J=2.4, 0.8 Hz, 1 H) ppm; MS (DCI/NH$_3$) m/z 260 (M+H)$^+$.

EXAMPLE 12

5-(pyrazin-2-yl)-3-(pyridin-3-yl)-1,2,4-oxadiazole

The titled compound was prepared according to the procedure of Example 8 using N'-hydroxynicotinimidamide (Aldrich) and pyrazine-2-carboxylic acid (Aldrich). $^1$H NMR (300 MHz, CD₃OD) δ 7.66 (ddd, J=8.0, 4.9, 1.0 Hz, 1 H), 8.60 (dt, J=8.0, 1.9 Hz, 1 H), 8.77 (dd, J=5.0, 1.8 Hz, 1 H), 8.86-8.89 (m, 1 H), 8.89-8.91 (m, 1 H), 9.34 (dd, J=2.4, 0.8 Hz, 1H), 9.56 (d, J=1.6 Hz, 1 H) ppm; MS (DCI/NH₃) m/z 226 (M+H)⁺.

EXAMPLE 13

5-(3,5-difluorophenyl)-3-(pyridin-3-yl)-1,2,4-oxadiazole

The title compound was prepared according to the procedure of Example 8 using N'-hydroxynicotinimidamide (Aldrich) and 3,5-difluorobenzoic acid (Aldrich). ¹H NMR (300 MHz, CD₃OD) δ 7.37 (tt, J=9.0, 2.3 Hz, 1 H), 7.65 (ddd, J=7.9, 5.0, 1.0 Hz, 1 H), 7.82-7.91 (m, 2 H), 8.56 (dt, J=7.9, 2.0 Hz, 1 H), 8.75 (dd, J=4.8, 1.6 Hz, 1 H), 9.30 (dd, J=2.0, 0.8 Hz, 1 H) ppm; MS (DCI/NH₃) m/z 260 (M+H)⁺.

EXAMPLE 14

5-(2,35-trifluorophenyl)-3-(pyridin-3-yl)-1,2,4-oxadiazole

The title compound was prepared according to the procedure of Example 8 using N'-hydroxynicotinimidamide (Aldrich) and 2,3,5-trifluorobenzoic acid (Aldrich). ¹H NMR (300 MHz, CD₃OD) δ 7.55-7.68 (m, 2 H), 7.83-7.90 (m, 1 H), 8.57 (dt, J=8.1, 1.9 Hz, 1H), 8.75 (dd, J=5.1, 1.7 Hz, 1 H), 9.30 (dd, J=2.2, 0.8 Hz, 1 H) ppm; MS (DCI/NH₃) m/z 278 (M+H)⁺.

EXAMPLE 15

5-(2,4,5-trifluorophenyl)-3-(pyridin-3-yl)-1,2,4-oxadiazole

The title compound was prepared according to the procedure of Example 8 using N'-hydroxynicotinimidamide (Aldrich) and 2,4,5-trifluorobenzoic acid (Aldrich). ¹H NMR (300 MHz, CD₃OD) δ 7.55 (td, J=10.3, 6.4 Hz, 1 H), 7.64 (ddd, J=8.1, 5.0, 0.8 Hz, 1 H), 8.23 (ddd, J=10.3, 8.6, 6.4 Hz, 1 H), 8.56 (dt, J=8.1, 1.9 Hz, 1 H), 8.75 (dd, J=5.1, 1.7 Hz, 1 H), 9.29 (d, J=1.4 Hz, 1 H) ppm; MS (DCI/NH₃) m/z 278 (M+H)⁺.

EXAMPLE 16

5-(2,5-difluorophenyl)-3-(pyridin-3-yl)-1,2,4-oxadiazole

The title compound was prepared according to the procedure of Example 8 using N'-hydroxynicotinimidamide (Aldrich) and 2,5-difluorobenzoic acid (Aldrich). ¹H NMR (300 MHz, CD₃OD) δ 7.41-7.56 (m, 2 H), 7.65 (ddd, J=7.9, 5.0, 1.0 Hz, 1 H), 7.98-8.04 (m, 1 H), 8.57 (dt, J=8.0, 1.9 Hz, 1 H), 8.75 (dd, J=5.2, 1.6 Hz, 1 H), 9.31 (dd, J=2.0, 0.8 Hz, 1 H); MS (DCI/NH₃) m/z 260 (M+H)⁺.

EXAMPLE 17

5-(4-chloro-2,5-difluorophenyl)-3-(pyridin-3-yl)-1,2,4-oxadiazole

The title compound was prepared according to the procedure of Example 8 using N'-hydroxynicotinimidamide (Aldrich) and 4-chloro-2,5-difluorobenzoic acid (Aldrich). ¹H NMR (300 MHz, CD₃OD) δ 7.65 (ddd, J=8.0, 4.9, 1.0 Hz, 1 H), 7.73 (dd, J=9.7, 5.9 Hz, 1 H), 8.18 (dd, J=8.8, 6.1 Hz, 1 H), 8.57 (dt, J=8.1, 1.9 Hz, 1 H), 8.75 (dd, J=4.7, 1.7 Hz, 1 H), 9.30 (dd, J=2.2, 0.8 Hz, 1 H) ppm; MS (DCI/NH₃) m/z 294 (M+H)⁺.

EXAMPLE 18

5-(5-methylpyrazin-2-yl)-3-(pyridin-3-yl)-1,2,4-oxadiazole

The title compound was prepared according to the procedure of Example 8 using N'-hydroxynicotinimidamide (Aldrich) and 5-methylpyrazine-2-carboxylic acid (Aldrich). ¹H NMR (300 MHz, CD₃OD) δ 2.71 (s, 3 H), 7.66 (ddd, J=8.0, 5.1, 0.8 Hz, 1 H), 8.59 (dt, J=7.9, 1.8 Hz, 1 H), 8.74-8.78 (m, 2 H), 9.33 (dd, J=2.0, 0.8 Hz, 1 H), 9.40 (d, J=1.2 Hz, 1 H) ppm; MS (DCI/NH₃) m/z 240 (M+H)⁺.

EXAMPLE 19

4-(3-(pyridin-3-yl)-1,2,4-oxadiazol-5-yl)benzonitrile

The title compound was prepared according to the procedure of Example 1 using N'-hydroxynicotinimidamide (Aldrich) and 4-cyanobenzoyl chloride (Aldrich). ¹H NMR (300 MHz, CD₃OD) δ 7.65 (ddd, J=8.0, 4.9, 1.0 Hz, 1 H), 8.02 (d, J=8.8 Hz, 2 H), 8.42 (d, J=8.8 Hz, 2 H), 8.57 (dt, J=8.1, 1.9 Hz, 1 H), 8.75 (dd, J=4.7, 1.7 Hz, 1 H), 9.31 (dd, J=2.2, 0.8 Hz, 1 H) ppm; MS (DCI/NH₃) m/z 249 (M+H)⁺.

EXAMPLE 20

2,3,6-trifluoro-5-(3-(pyridin-3-yl)-1,2,4-oxadiazol-5-yl)phenol

The title compound was prepared according to the procedure of Example 8 using N'-hydroxynicotinimidamide (Aldrich) and 2,4,5-trifluoro-3-hydroxybenzoic acid (Aldrich). ¹H NMR (300 MHz, CD₃OD) δ 7.63-7.76 (m, 2 H), 8.44 (dt, J=7.9, 2.0 Hz, 1 H), 8.83 (dd, J=4.8, 1.6 Hz, 1 H), 9.25 (d, J=1.6 Hz, 1 H) ppm; MS (DCI/NH₃) m/z 294 (M+H)⁺.

EXAMPLE 21

2-fluoro-5-(3-(pyridin-3-yl)-1,2,4-oxadiazol-5-yl)phenol

The title compound was prepared according to the procedure of Example 8 using N'-hydroxynicotinimidamide (Aldrich) and 4-fluoro-3-hydroxybenzoic acid (Aldrich). ¹H NMR (300 MHz, DMSO-d₆) δ 7.45 (dd, J=11.1, 8.7 Hz, 1 H), 7.62-7.71 (m, 2 H), 7.78 (dd, J=8.3, 2.0 Hz, 1 H), 8.43 (dt, J=7.9, 1.8 Hz, 1 H), 8.82 (dd, J=5.0, 1.8 Hz, 1 H), 9.24 (d, J=2.0 Hz, 1 H) ppm; MS (DCI/NH₃) m/z 258 (M+H)⁺.

EXAMPLE 22

2-fluoro-4-(3-(pyridin-3-yl)-1,2,4-oxadiazol-5-yl)phenol

The title compound was prepared according to the procedure of Example 8 using N'-hydroxynicotinimidamide (Aldrich) and 3-fluoro-4-hydroxybenzoic acid (Aldrich). ¹H NMR (300 MHz, CD₃OD) δ 7.09 (t, J=8.7 Hz, 1 H), 7.63 (ddd, J=7.9, 5.2, 0.8 Hz, 1 H), 7.86-7.93 (m, 2 H), 8.53 (dt, J=7.9, 2.0 Hz, 1 H), 8.72 (dd, J=4.8, 1.6 Hz, 1 H), 9.27 (dd, J=2.4, 0.8 Hz, 1 H) ppm; MS (DCI/NH$_3$) m/z 258 (M+H)$^+$.

EXAMPLE 23

5-(3-chloro-4-fluorophenyl)-3-(pyridin-3-yl)-1,2,4-oxadiazole

The title compound was prepared according to the procedure of Example 8 using N'-hydroxynicotinimidamide (Aldrich) and 3-chloro-4-fluorobenzoic acid (Aldrich). $^1$H NMR (300 MHz, CD$_3$OD) δ 7.54 (t, J=8.8 Hz, 1 H), 7.64 (ddd, J=8.1, 5.0, 0.8 Hz, 1 H), 8.24 (ddd, J=8.6, 4.6, 2.0 Hz, 1 H), 8.39 (dd, J=7.0, 2.2 Hz, 1 H), 8.55 (dt, J=8.1, 1.9 Hz, 1 H), 8.74 (dd, J=4.9, 1.5 Hz, 1 H), 9.29 (dd, J=2.2, 0.8 Hz, 1 H) ppm; MS (DCI/NH$_3$) m/z 276 (M+H)$^+$.

EXAMPLE 24

5-(3,4-dichlorophenyl)-3-(pyridin-3-yl)-1,2,4-oxadiazole

The title compound was prepared according to the procedure of Example 8 using N'-hydroxynicotinimidamide (Aldrich) and 3,4-dichlorobenzoic acid (Aldrich). $^1$H NMR (300 MHz, CD$_3$OD) δ 7.64 (ddd, J=8.0, 5.1, 0.8 Hz, 1 H), 7.82 (d, J=8.3 Hz, 1 H), 8.14-8.19 (m, 1 H), 8.40 (d, J=2.0 Hz, 1 H), 8.56 (dt, J=7.9, 2.0 Hz, 1 H), 8.75 (dd, J=5.2, 1.6 Hz, 1 H), 9.29 (dd, J=2.2, 1.0 Hz, 1 H) ppm; MS (DCI/NH$_3$) m/z 292 (M+H)$^+$.

EXAMPLE 25

2-nitro-5-(3-(pyridin-3-yl)-1,2,4-oxadiazol-5-yl)phenol

The title compound was prepared according to the procedure of Example 8 using N'-hydroxynicotinimidamide (Aldrich) and 3-hydroxy-4-nitrobenzoic acid (Maybridge). $^1$H NMR (300 MHz, DMSO-d$_6$) δ 6.51 (d, J=9.1 Hz, 1 H), 6.92-7.31 (s (broad), 1 H), 7.61 (ddd, J=7.9, 4.8, 0.8 Hz, 1 H), 7.68 (dd, J=9.1, 2.4 Hz, 1 H), 8.40 (dt, J=7.9, 2.0 Hz, 1 H), 8.53 (d, J=2.4 Hz, 1 H), 8.77 (dd, J=4.8, 1.6 Hz, 1 H), 9.20 (d, J=1.6 Hz, 1 H) ppm; MS (DCI/NH$_3$) m/z 285 (M+H)$^+$.

EXAMPLE 26

5-(2,36-trifluorophenyl)-3-(pyridin-3-yl)-1,2,4-oxadiazole

The title compound was prepared according to the procedure of Example 8 using N'-hydroxynicotinimidamide (Aldrich) and 2,3,6-trifluorobenzoic acid (Aldrich). $^1$H NMR (300 MHz, CD$_3$OD) δ 7.26-7.35 (m, J=9.4, 9.4, 3.8, 2.0 Hz, 1 H), 7.62-7.77 (m, 2 H), 8.57 (dt, J=8.0, 1.9 Hz, 1 H), 8.76 (dd, J=4.8, 1.6 Hz, 1 H), 9.30 (dd, J=2.4, 0.8 Hz, 1 H) ppm; MS (DCI/NH$_3$) m/z 278 (M+H)$^+$.

EXAMPLE 27

2,2,2-trifluoro-1-(4-(3-(pyridin-3-yl)-1,2,4-oxadiazol-5-yl)phenyl)ethanone trifluoroacetate The title compound was prepared according to the procedure of Example 8 using N'-hydroxynicotinimidamide (Aldrich) and 4-(2,2,2-trifluoroacetyl)benzoic acid (Aldrich). $^1$H NMR (300 MHz, CD$_3$OD) δ 7.81 (ddd, J=7.9, 5.2, 0.8 Hz, 1 H), 7.96 (d, J=8.3 Hz, 2 H), 8.28 (d, J=8.7 Hz, 2 H), 8.76 (dt, J=8.2, 1.8 Hz, 1 H), 8.82 (dd, J=5.2, 1.6 Hz, 1 H), 9.38 (d, J=1.6 Hz, 1 H) ppm; MS (DCI/NH$_3$) m/z 320 (M+H)$^+$.

EXAMPLE 28

5-(3-fluorophenyl)-3-(pyridin-3-yl)-1,2,4-oxadiazole

The title compound was prepared according to the procedure of Example 8 using N'-hydroxynicotinimidamide (Aldrich) and 3-fluorobenzoic acid (Aldrich). $^1$H NMR (300 MHz, CD$_3$OD) δ 7.43-7.51 (m, J=8.5, 8.5, 2.6, 1.0 Hz, 1 H), 7.61-7.72 (m, 2 H), 7.98 (ddd, J=9.1, 2.6, 1.4 Hz, 1 H), 8.08 (ddd, J=8.0, 1.3, 1.0 Hz, 1 H), 8.56 (dt, J=8.0, 1.9 Hz, 1 H), 8.74 (dd, J=5.2, 1.6 Hz, 1 H), 9.30 (dd, J=2.0, 0.8 Hz, 1 H) ppm; MS (DCI/NH$_3$) m/z 242 (M+H)$^+$.

EXAMPLE 29

5-(4-fluorophenyl)-3-(pyridin-3-yl)-1,2,4-oxadiazole

The title compound was prepared according to the procedure of Example 8 using N'-hydroxynicotinimidamide (Aldrich) and 4-fluorobenzoic acid (Aldrich). $^1$H NMR (300 MHz, CD$_3$OD) δ 7.39 (t, J=8.9 Hz, 2 H), 7.64 (ddd, J=7.9, 4.8, 0.8 Hz, 1 H), 8.27-8.35 (m, 2 H), 8.55 (ddd, J=8.1, 2.0, 1.8 Hz, 1 H), 8.74 (dd, J=5.0, 1.8 Hz, 1 H), 9.29 (dd, J=2.2, 1.0 Hz, 1 H) ppm; MS (DCI/NH$_3$) m/z 242 (M+H)$^+$.

EXAMPLE 30

5-(2-fluorophenyl)-3-(pyridin-3-yl)-1,2,4-oxadiazole

The title compound was prepared according to the procedure of Example 8 using N'-hydroxynicotinimidamide (Aldrich) and 2-fluorobenzoic acid (Aldrich). $^1$H NMR (300 MHz, CD$_3$OD) δ 7.38-7.49 (m, 2 H), 7.64 (ddd, J=8.0, 4.9, 1.0 Hz, 1 H), 7.70-7.79 (m, 1 H), 8.28 (td, J=7.5, 1.9 Hz, 1 H), 8.57 (dt, J=8.1, 1.9 Hz, 1 H), 8.74 (dd, J=4.7, 1.7 Hz, 1 H), 9.31 (dd, J=2.2, 0.8 Hz, 1 H) ppm; MS (DCI/NH$_3$) m/z 242 (M+H)$^+$.

EXAMPLE 31

3-fluoro-5-(3-(pyridin-3-yl)-1,2,4-oxadiazol-5-yl)benzonitrile

The title compound was prepared according to the procedure of Example 8 using N'-hydroxynicotinimidamide (Aldrich) and 3-cyano-5-fluorobenzoic acid (Aldrich). $^1$H NMR (300 MHz, CD$_3$OD) δ 7.65 (ddd, J=8.0, 5.1, 0.8 Hz, 1 H), 7.95 (ddd, J=8.1, 2.6, 1.6 Hz, 1 H), 8.32 (ddd, J=8.7, 2.6, 1.4 Hz, 1 H), 8.46 (t, J=1.4 Hz, 1 H), 8.58 (ddd, J=8.1, 2.0, 1.8 Hz, 1 H), 8.76 (dd, J=5.2, 1.6 Hz, 1 H), 9.31 (dd, J=2.0, 0.8 Hz, 1 H) ppm; MS (DCI/NH$_3$) m/z 267 (M+H)$^+$.

EXAMPLE 32

3-(2,3-difluorophenyl)-5-(pyridin-3-yl)-1,2,4-oxadiazole hydrochloric acid

EXAMPLE 32A 3-(2,3-difluorophenyl)-5-(pyridin-3-yl)-1,2,4-oxadiazole

The title compound was prepared according to the procedure of Example 1 using 2,3-difluoro-N'-hydroxybenzimidamide (Tyger Scientific) and nicotinoyl chloride hydrochloride (Aldrich). $^1$H NMR (300 MHz, DMSO-d$_6$) δ 7.42-7.61 (m, 1 H), 7.67-7.85 (m, 2 H), 7.91-8.04 (m, 1 H), 8.57 (dt, J=8.1, 1.9 Hz, 1 H), 8.92 (dd, J=4.8, 1.6 Hz, 1 H), 9.36 (dd, J=2.4, 0.8 Hz, 1 H) ppm; MS (DCI/NH$_3$) m/z 260 (M+H)$^+$.

EXAMPLE 32B 3-(2,3-difluorophenyl)-5-(pyridin-3-yl)-1,2,4-oxadiazole hydrochloric acid A solution of the product of Example 32A (320 mg, 1.23 mmol) in ethyl acetate (5 mL) was stirred with hydrochloric acid (Aldrich, 4 M in dioxane, 0.5 mL, 2.0 mmol) at ambient temperature for 4 hours. The titled compound was collected by filtration and dried under vacuum. $^1$H NMR (300 MHz, CD$_3$OD) δ 7.35-7.46 (m, 1 H), 7.49-7.63 (m, 1 H), 7.93-8.07 (m, 1 H), 8.24 (dd, J=8.1, 5.8 Hz, 1 H), 9.10 (dd, J=5.8, 1.4 Hz, 1 H), 9.23 (dt, J=8.0, 1.8 Hz, 1 H), 9.66 (d, J=2.0 Hz, 1 H) ppm; MS (DCI/NH$_3$) m/z 260 (M+H)$^+$.

EXAMPLE 33

3-(3,4-difluorophenyl)-5-(pyridin-3-yl)-1,2,4-oxadiazole hydrochloric acid

EXAMPLE 33A 3-(3,4-difluorophenyl)-5-(pyridin-3-yl)-1,2,4-oxadiazole

The title compound was prepared according to the procedure of Example 1 using 3,4-difluoro-N'-hydroxybenzimidamide (Tyger Scientific) and nicotinoyl chloride hydrochloride (Aldrich). $^1$H NMR (300 MHz, DMSO-d$_6$) δ 7.74 (dd, J=7.5, 4.4 Hz, 1 H), 8.60 (dt, J=7.8, 2.1 Hz, 1 H), 8.93 (dd, J=4.8, 1.6 Hz, 1 H), 9.38 (dd, J=2.2, 1.0 Hz, 1 H), 9.44-9.48 (m, 3 H) ppm; MS (DCI/NH$_3$) m/z 260 (M+H)$^+$.

EXAMPLE 33B 3-(3,4-difluorophenyl)-5-(pyridin-3-yl)-1,2,4-oxadiazole hydrochloric acid A solution of the product of Example 32A (280 mg, 1.08 mmol) in ethyl acetate (5 mL) was stirred with hydrochloric acid (Aldrich, 4 M in dioxane, 0.5 mL, 2.0 mmol) at ambient temperature for 4 hours. The title compound was collected by filtration and dried under vacuum. $^1$H NMR (300 MHz, CD$_3$OD) δ 7.52 (td, J=10.5, 8.3 Hz, 1 H), 8.00-8.17 (m, 2 H), 8.26 (ddd, J=8.1, 5.8, 0.7 Hz, 1 H), 9.08-9.14 (m, 1 H), 9.22-9.30 (m, 1 H), 9.66 (d, J=2.0 Hz, 1 H) ppm; MS (DCI/NH$_3$) m/z 260 (M+H)$^+$.

EXAMPLE 34

5-(2,6-difluorophenyl)-3-(pyridin-3-yl)-1,2,4-oxadiazole

The title compound was prepared according to the procedure of Example 8 using N'-hydroxynicotinimidamide (Aldrich) and 2,6-difluorobenzoic acid (Aldrich). $^1$H NMR (300 MHz, CD$_3$OD) δ 7.29 (t, J=8.6 Hz, 2 H), 7.65 (ddd, J=8.0, 4.9, 1.0 Hz, 1 H), 7.77 (tt, J=8.6, 6.1 Hz, 1 H), 8.57 (ddd, J=8.3, 1.9, 1.7 Hz, 1 H), 8.75 (dd, J=4.7, 1.7 Hz, 1 H), 9.30 (dd, J=2.2, 0.8 Hz, 1 H) ppm; MS (DCI/NH$_3$) m/z 260 (M+H)$^+$.

EXAMPLE 35

3-(3-(pyridin-3-yl)-1,2,4-oxadiazol-5-yl)benzenesulfonamide

The title compound was prepared according to the procedure of Example 8 using N'-hydroxynicotinimidamide (Aldrich) and 3-sulfamoylbenzoic acid (Oakwood). $^1$H NMR (300 MHz, CD$_3$OD) δ 7.65 (ddd, J=8.0, 4.9, 1.0 Hz, 1 H), 7.83 (t, J=7.9 Hz, 1 H), 8.21 (ddd, J=7.9, 1.8, 1.0 Hz, 1 H), 8.45 (dt, J=7.9, 1.4 Hz, 1 H), 8.58 (dt, J=8.0, 1.9 Hz, 1 H), 8.73-8.77 (m, 2 H), 9.31 (dd, J=2.2, 1.0 Hz, 1 H) ppm; MS (DCI/NH$_3$) m/z 303 (M+H)$^+$.

EXAMPLE 36

5-(2,4-difluorophenyl)-3-(pyridin-3-yl)-1,2,4-oxadiazole

The title compound was prepared according to the procedure of Example 8 using N'-hydroxynicotinimidamide (Aldrich) and 2,4-difluorobenzoic acid (Aldrich). $^1$H NMR (300 MHz, CD$_3$OD) δ 7.23-7.36 (m, 2 H), 7.64 (ddd, J=8.1, 5.0, 0.8 Hz, 1 H), 8.35 (td, J=8.5, 6.4 Hz, 1 H), 8.56 (dt, J=7.8, 1.9 Hz, 1 H), 8.74 (dd, J=5.1, 1.7 Hz, 1 H), 9.30 (dd, J=2.2, 0.8 Hz, 1 H) ppm; MS (DCI/NH$_3$) m/z 260 (M+H)$^+$.

EXAMPLE 37

5-(2,3,4-trifluorophenyl)-3-(pyridin-3-yl)-1,2,4-oxadiazole

The title compound was prepared according to the procedure of Example 8 using N'-hydroxynicotinimidamide (Aldrich) and 2,3,4-trifluorobenzoic acid (Aldrich). $^1$H NMR (300 MHz, CD$_3$OD) δ 7.37-7.48 (m, J=9.3, 9.3, 7.1, 2.4 Hz, 1 H), 7.64 (ddd, J=7.9, 5.0, 1.0 Hz, 1 H), 8.08-8.18 (m, 1 H), 8.56 (dt, J=8.0, 1.9 Hz, 1 H), 8.75 (dd, J=5.0, 1.8 Hz, 1 H), 9.30 (dd, J=2.0, 0.8 Hz, 1 H) ppm; MS (DCI/NH$_3$) m/z 278 (M+H)$^+$.

EXAMPLE 38

5-(3,4,5-trifluorophenyl)-3-(pyridin-3-yl)-1,2,4-oxadiazole

The title compound was prepared according to the procedure of Example 8 using N'-hydroxynicotinimidamide (Aldrich) and 3,4,5-trifluorobenzoic acid (Aldrich). $^1$H NMR (300 MHz, CD$_3$OD) δ 7.64 (ddd, J=8.0, 4.9, 1.0 Hz, 1 H), 8.01-8.13 (m, 2 H), 8.56 (ddd, J=8.1, 1.8, 1.6 Hz, 1 H), 8.75 (dd, J=4.8, 1.6 Hz, 1 H), 9.29 (dd, J=2.0, 0.8 Hz, 1 H) ppm; MS (DCI/NH$_3$) m/z 278 (M+H)$^+$.

EXAMPLE 39

5-(4-chloro-3-fluorophenyl)-3-(pyridin-3-yl)-1,2,4-oxadiazole

The title compound was prepared according to the procedure of Example 8 using N'-hydroxynicotinimidamide (Aldrich) and 4-chloro-3-fluorobenzoic acid (Aldrich). $^1$H NMR (300 MHz, CD$_3$OD) δ 7.64 (ddd, J=7.9, 5.0, 1.0 Hz, 1 H), 7.78 (dd, J=8.3, 7.5 Hz, 1 H), 8.07 (dd, J=8.3, 2.0, 0.8 Hz, 1 H), 8.12 (dd, J=9.5, 2.0 Hz, 1 H), 8.55 (dt, J=7.9, 2.0 Hz, 1 H), 8.74 (dd, J=5.0, 1.8 Hz, 1 H), 9.28-9.30 (m, 1 H) ppm; MS (DCI/NH$_3$) m/z 276 (M+H)$^+$.

EXAMPLE 40

5-(3-nitrophenyl)-3-(pyridin-3-yl)-1,2,4-oxadiazole

The title compound was prepared according to the procedure of Example 8 using N'-hydroxynicotinimidamide (Aldrich) and 3-nitrobenzoyl chloride (Aldrich). $^1$H NMR (300 MHz, CDCl$_3$) δ 7.44-7.55 (m, 1 H), 7.82 (t, J=8.3 Hz, 1 H), 8.43-8.60 (m, 3 H), 8.80 (dd, J=4.7, 1.7 Hz, 1 H), 9.07-9.13 (m, 1 H), 9.42 (d, J=2.0 Hz, 1 H) ppm; MS (DCI/NH$_3$) m/z 269 (M+H)$^+$.

EXAMPLE 41

5-(3-(methylsulfonyl)phenyl)-3-(pyridin-3-yl)-1,2,4-oxadiazole

The title compound was prepared according to the procedure of Example 8 using N'-hydroxynicotinimidamide (Aldrich) and 3-(methylsulfonyl)benzoic acid (Aldrich). $^1$H NMR (300 MHz, CD$_3$OD) δ 3.24 (s, 3 H), 7.65 (ddd, J=8.0, 4.9, 1.0 Hz, 1 H), 7.89-7.96 (m, 1 H), 8.28 (ddd, J=8.0, 1.9, 1.0 Hz, 1 H), 8.55-8.61 (m, 2 H), 8.75 (dd, J=5.1, 1.7 Hz, 1 H), 8.78 (t, J=1.5 Hz, 1 H), 9.32 (dd, J=2.2, 0.8 Hz, 1 H) ppm; MS (DCI/NH$_3$) m/z 302 (M+H)$^+$.

EXAMPLE 42

3-(2-chloropyridin-4-yl)-5-(pyridin-3-yl)-1,2,4-oxadiazole

EXAMPLE 42A

2-chloro-N'-hydroxyisonicotinimidamide

A solution of 2-chloroisonicotinonitrile (Aldrich, 0.73 g, 5.27 mmol), and hydroxylamine (Aldrich, 50 wt %, 0.348 g, 5.27 mmol) in methanol (10 mL) was heated to reflux and stirred for 1 hour. The volatiles were removed under reduced pressure to give the title compound. $^1$H NMR (300 MHz, DMSO-d$_6$) δ 6.09 (s, 2 H), 7.67 (dd, J=5.4, 1.4 Hz, 1H), 7.73 (d, J=2.0 Hz, 1 H), 8.40 (d, J=5.2 Hz, 1 H), 10.22 (s, 1 H) ppm; MS (DCI/NH$_3$) m/z 172 (M+H)$^+$, 174 (M+H)$^+$.

EXAMPLE 42B

3-(2-chloropyridin-4-yl)-5-(pyridin-3-yl)-1,2,4-oxadiazole

The title compound was prepared according to the procedure of Example 1 using the product of Example 42A and nicotinoyl chloride hydrochloride (Aldrich). $^1$H NMR (300 MHz, DMSO-d$_6$) δ 7.73 (ddd, J=8.0, 4.9, 1.0 Hz, 1 H), 8.04-8.13 (m, 2 H), 8.59 (dt, J=7.9, 2.0 Hz, 1 H), 8.71 (d, J=5.2 Hz, 1 H), 8.92 (dd, J=5.0, 1.8 Hz, 1 H), 9.38 (dd, J=2.2, 1.0 Hz, 1 H) ppm; MS (DCI/NH$_3$) m/z 259 (M+H)$^+$, 261 (M+H)$^+$.

EXAMPLE 43

3-(3-(pyridin-3-yl)-1,2,4-oxadiazol-5-yl)benzamide

A solution of the product of Example 1 (248 mg, 1 mmol) in THF (10 ml) was stirred with potassium trimethylsilanolate (257 mg, 2.000 mmol) at 65° C. for 10 hours. It was then quenched with water (20 mL) and stirred at ambient temperature for 2 hours. The precipitate was filtered and dried under vacuum to give the title compound. $^1$H NMR (300 MHz, DMSO-d$_6$) δ 7.67 (ddd, J=7.9, 4.8, 0.8 Hz, 1 H), 7.78 (t, J=7.7 Hz, 1 H), 8.23 (dt, J=8.1, 1.4, 1.2 Hz, 1 H), 8.30 [s (broad, 2H], 8.36 (dt, J=8.1, 1.3 Hz, 1 H), 8.48 (dt, J=7.9, 2.0 Hz, 1 H), 8.68-8.73 (m, 1 H), 8.83 (dd, J=4.8, 1.6 Hz, 1 H), 9.28 (dd, J=2.2, 1.0 Hz, 1 H) ppm; MS (DCI/NH$_3$) m/z 267 (M+H)$^+$.

EXAMPLE 44

4-(5-(pyridin-3-yl)-1,2,4-oxadiazol-3-yl)pyridin-2 (1H)-one hydrochloric acid A solution of the product of Example 42 (100 mg, 0.39 mmol) in concentrated hydrochloric acid (Aldrich, 36.5%, 3.0 mL) was heated in an Emry™ Creator microwave to 150° C. at 300 watts for 60 minutes. It was then concentrated. The residue was stirred in ethanol/ethyl acetate (v. 1/1, 5 mL) at ambient temperature for 1 hour. The title compound was collected by filtration and dried. $^1$H NMR (300 MHz, DMSO-d$_6$) δ 6.75 (dd, J=6.7, 1.6 Hz, 1 H), 7.04 (d, J=1.6 Hz, 1 H), 7.61 (d, J=5.9 Hz, 1 H), 7.67-7.81 (m, 1 H), 8.56 (dt, J=8.0, 1.9 Hz, 1 H), 8.91 (dd, J=5.0, 1.8 Hz, 1 H), 9.31-9.40 (m, 1 H) ppm; MS (DCI/NH$_3$) m/z 241 (M+H)$^+$.

EXAMPLE 45 tert-butyl 3-(3-(pyridin-3-yl)-1,2,4-oxadiazol-5-yl)benzoate

N'-Hydroxynicotinimidamide (274 mg, 2.00 mmol) was coupled with 3-(tert-butoxycarbonyl)benzoic acid (Aldrich) according to the procedure described in Example 8. $^1$H NMR (300 MHz, CD$_3$OD) δ 1.65 (s, 9 H), 7.65 (ddd, J=7.9, 4.8, 0.8 Hz, 1 H), 7.71-7.77 (m, 1 H), 8.26 (ddd, J=7.7, 1.8, 1.6 Hz, 1 H), 8.42-8.46 (m, 1 H), 8.57 (dt, J=7.9, 2.0 Hz, 1 H), 8.73-8.78 (m, 2 H), 9.31 (dd, J=2.2, 1.0 Hz, 1 H) ppm; MS (DCI/NH$_3$) m/z 324 (M+H)$^+$.

EXAMPLE 46

2-amino-5-(3-(pyridin-3-yl)-1,2,4-oxadiazol-5-yl)phenol

A solution of the product of Example 25 (284 mg, 1 mmol) in tetrahydrofuran (10 mL) was stirred with Raney®-nickel (Aldrich, 100 mg) under hydrogen at ambient temperature for 2 hours. The catalyst was then removed by filtration and the organic solution concentrated to give the title compound. $^1$H NMR (300 MHz, DMSO-d$_6$) δ 5.67 (s, 2 H), 6.74 (d, J=8.1 Hz, 1 H), 7.41-7.50 (m, 2 H), 7.62 (dd, J=8.3, 4.6 Hz, 1 H), 8.39 (dt, J=8.2, 1.9, 1.7 Hz, 1 H), 8.78 (dd, J=4.7, 1.7 Hz, 1 H), 9.20 (d, J=1.7 Hz, 1 H), 9.74 (s, broad), 1 H) ppm; MS (DCI/NH$_3$) m/z 255 (M+H)$^+$.

EXAMPLE 47

N,N-dimethyl-4-(5-(pyridin-3-yl)-1,2,4-oxadiazol-3-yl)pyridin-2-amine

A solution of the product of Example 42 (100 mg, 0.39 mmol) in dimethylformamide (2.0 mL) and ammonium hydroxide (0.5 mL) was sealed and heated to 150° C. in an Emry™ Creator microwave to 150° C. at 300 watts for 60 minutes. It was then concentrated. The residue was stirred in water (5 mL) at ambient temperature for 1 hour. The title compound was collected by filtration and dried. $^1$H NMR (300 MHz, DMSO-d$_6$) δ 3.12 (s, 6 H), 7.18 (dd, J=5.2, 1.2 Hz, 1 H), 7.21 (t, J=1.2 Hz, 1 H), 7.66-7.78 (m, 1 H), 8.31 (dd, J=4.8, 0.8 Hz, 1 H), 8.57 (ddd, J=8.3, 2.0, 1.6 Hz, 1 H), 8.91 (dd, J=5.0, 1.8 Hz, 1 H), 9.35 (d, J=2.4 Hz, 1 H) ppm; MS (DCI/NH$_3$) m/z 268 (M+H)$^+$.

EXAMPLE 48

3-(3-(pyridin-3-yl)-1,2,4-oxadiazol-5-yl)benzoic acid

A solution of the product of Example 45 (180 mg, 0.56 mmol) in methylene chloride (5 mL) was stirred with trifluoroacetic acid (1 mL) at room temperature for 4 hours. It was then concentrated and the residue was stirred in water (15 mL) for 1 hour. The precipitate was collected by filtration and dried to give the title compound. $^1$H NMR (300 MHz, DMSO-d$_6$) δ 7.66 (ddd, J=7.9, 4.8, 0.8 Hz, 1 H), 7.83 (t, J=7.5 Hz, 1 H), 8.28 (ddd, J=8.0, 1.5, 1.2 Hz, 1 H), 8.42-8.51 (m, 2 H), 8.70 (t, J=1.6 Hz, 1 H), 8.83 (dd, J=5.0, 1.8 Hz, 1 H), 9.28 (dd, J=2.2, 1.0 Hz, 1 H) ppm; MS (DCI/NH$_3$) m/z 268 (M+H)$^+$.

EXAMPLE 49

5-(3-(1H-tetrazol-5-yl)phenyl)-3-(pyridin-3-yl)-1,2,4-oxadiazole hydrochloric acid A solution of the product of Example 1 (248 mg, 1.0 mmol) in toluene (anhydrous, 10 mL) was stirred with azidotributylstannane (Aldrich, 498 mg, 1.50 mmol) at 110° C. for 15 hours. It was then cooled to ambient temperature and stirred with 5 mL of sodium hydroxide (1 N) at ambient temperature for 1 hour. The organic solution was separated, the aqueous mixture was acidified to pH=2-3 with hydrochloric acid (10 wt. %) and stirred for 2 hours. The precipitate was collected by filtration and dried to give the title product. $^1$H NMR (300 MHz, DMSO-d$_6$) δ 7.70-7.76 (m, 1 H), 7.86-7.98 (m, 1 H), 8.23 (ddd, J=7.8, 1.7, 1.0 Hz, 0.2 H), 8.38-8.46 (m, 1.6 H), 8.49-8.53 (m, 0.2 H), 8.56 (ddd, J=8.1, 1.9 Hz, 0.8 H), 8.65 (ddd, J=1.7, 0.7 Hz, 0.2 H), 8.83-8.92 (m, 2 H), 9.30 (dd, J=2.2, 0.8 Hz, 0.2 H), 9.33 (dd, J=2.2, 0.8 Hz, 0.8 H) ppm; MS (DCI/NH$_3$) m/z 292 (M+H)$^+$.

EXAMPLE 50

N,N-diethyl-3-(3-(pyridin-3-yl)-1,2,4-oxadiazol-5-yl)benzenesulfonamide

EXAMPLE 50A

3-(N,N-diethylsulfamoyl)benzoic acid

Diethylamine (Aldrich, 2.5 mL, 24 mmol) was added to a solution of 3-(chlorosulfonyl)benzoic acid (Aldrich, 2.0 g, 9.1 mmol) in anhydrous dichloromethane (20 mL) at 0° C. The mixture was then stirred at 0° C. for 2 hours. The volatiles were removed under reduced pressure. The residue was treated with aqueous potassium hydrogensulfate (1 M, 10 mL) and then extracted with ethyl acetate (3×50 mL). The combined extracts were dried over magnesium sulfate filtered and then concentrated to give the title compound. $^1$H NMR (300 MHz, CD$_3$OD) δ 1.13 (t, J=7.1 Hz, 6 H), 3.22-3.30 (m, 4 H), 7.69 (t, J=7.8 Hz, 1H), 8.03 (ddd, J=7.9, 1.9, 1.4 Hz, 1 H), 8.25 (dt, J=7.8, 1.4 Hz, 1 H), 8.40 (t, J=1.7 Hz, 1 H) ppm; MS (DCI/NH$_3$) m/z 275 (M+NH$_4$)$^+$.

EXAMPLE 50B

N,N-Diethyl-3-(3-(pyridin-3-yl)-1,2,4-oxadiazol-5-yl)benzenesulfonamide

The title compound was prepared according to the procedure of Example 8 using N'-hydroxynicotinimidamide (Aldrich) and the product of Example 50A. $^1$H NMR (300 MHz, CD$_3$OD) δ 1.17 (t, J=7.1 Hz, 6 H), 3.29-3.37 (m, 4 H), 7.65 (ddd, J=8.1, 5.0, 0.8 Hz, 1 H), 7.86 (t, J=7.6 Hz, 1 H), 8.14 (ddd, J=7.9, 1.8, 1.2 Hz, 1 H), 8.48 (dt, J=7.9, 1.5 Hz, 1 H), 8.58 (dt, J=8.1, 1.9 Hz, 1 H), 8.62 (t, J=1.5 Hz, 1 H), 8.75 (dd, J=5.1, 1.7 Hz, 1 H), 9.31 (dd, J=2.2, 0.8 Hz, 1 H) ppm; MS (DCI/NH$_3$) m/z 359 (M+H)$^+$.

EXAMPLE 51

2-fluoro-5-(3-(pyridin-3-yl)-1,2,4-oxadiazol-5-yl)benzonitrile

The title compound was prepared according to the procedure of Example 8 using N'-hydroxynicotinimidamide (Aldrich) and 3-cyano-4-fluorobenzoic acid (Aldrich). $^1$H NMR (300 MHz, CD$_3$OD) δ ppm 7.62-7.71 (m, 2 H), 8.54-8.63 (m, 2 H), 8.69 (dd, J=5.9, 2.2 Hz, 1 H), 8.75 (dd, J=4.9, 1.5 Hz, 1 H), 9.30 (dd, J=2.0, 1.0 Hz, 1 H); MS (DCI/NH$_3$) m/z 267 (M+H)$^+$.

EXAMPLE 52

3-(3-(1H-tetrazol-5-yl)phenyl)-5-(pyridin-3-yl)-1,2,4-oxadiazole hydrochloric acid The title compound was prepared according to the procedure of Example 49 using the product of Example 3 and azidotributylstannane (Aldrich). $^1$H NMR (300 MHz, DMSO-d$_6$) δ 7.74 (dd, J=7.3, 5.4 Hz, 1 H), 7.87 (t, J=7.7 Hz, 1 H), 8.25-8.43 (m, 2 H), 8.53-8.70 (m, 1 H), 8.75-8.85 (m, 1 H), 8.88-9.00 (m, 1 H), 9.32-9.58 (m, 1 H) ppm; MS (DCI/NH$_3$) m/z 292 (M+H)$^+$.

EXAMPLE 53

3-(6-chloropyridin-3-yl)-5-(pyridin-3-yl)-1,2,4-oxadiazole

EXAMPLE 53A

6-Chloro-N'-hydroxynicotinimidamide

A solution of 2-chloroisonicotinonitrile (Aldrich, 5.0 g, 36.1 mmol) and hydroxylamine (Aldrich, 50% wt, 2.38 g, 36.0 mmol) in methanol (100 ml) was heated to reflux and stirred for 1 hour. The volatiles were removed under reduced pressure to give the title compound. $^1$H NMR (300 MHz, DMSO-d$_6$) δ 6.03 (s, 2 H), 7.54 (d, J=8.7 Hz, 1 H), 8.07 (dd, J=8.3, 2.4 Hz, 1 H), 8.67 (d, J=2.8 Hz, 1 H), 9.94 (s, 1 H) ppm; MS (DCI/NH$_3$) m/z 172 (M+H)$^+$, 189 (M+H)$^+$.

EXAMPLE 53B

3-(6-chloropyridin-3-yl)-5-(pyridin-3-yl)-1,2,4-oxadiazole

The title compound was prepared according to the procedure of Example 1 using the product of Example 53A and nicotinoyl chloride hydrochloride (Aldrich). $^1$H NMR (300 MHz, CD$_3$OD) δ 7.62-7.75 (m, 2 H), 8.53 (dd, J=8.1, 2.4 Hz, 1 H), 8.60-8.67 (m, 1 H), 8.85 (dd, J=5.1, 1.7 Hz, 1 H), 9.14 (dd, J=2.4, 0.7 Hz, 1 H), 9.39 (dd, J=2.2, 0.8 Hz, 1 H) ppm; MS (DCI/NH$_3$) m/z 259 (M+H)$^+$, 261 (M+H)$^+$.

EXAMPLE 54

5-(6-chloropyridin-3-yl)-3-(pyridin-3-yl)-1,2,4-oxadiazole

The title compound was prepared according to the procedure of Example 1 using N'-hydroxynicotinimidamide (Tyger) and 6-chloronicotinoyl chloride (Aldrich). $^1$H NMR (300 MHz, CDCl$_3$) δ 7.48 (dd, J=7.6, 5.3 Hz, 1 H), 7.57 (d, J=8.5 Hz, 1 H), 8.40-8.48 (m, 2 H), 8.80 (dd, J=4.7, 1.7 Hz, 1 H), 9.24 (d, J=2.4 Hz, 1 H), 9.40 (d, J=2.4 Hz, 1 H) ppm; MS (DCI/NH$_3$) m/z 259 (M+H)$^+$, 261 (M+H)$^+$.

EXAMPLE 55

5-(5-(pyridin-3-yl)-1,2,4-oxadiazol-3-yl)pyridin-2(1H)-one

A solution of the product of Example 53B (0.10 g, 0.39 mmol) in concentrated hydrochloric acid (1.0 mL) was heated in a microwave to 150° C. at 300 watts for 60 minutes. It was then concentrated under reduced pressure and the residue was purified by chromatography [silica gel, CHCl$_3$/methanol (with 10% v/v ammonium hydroxide), v. 90/10] to provide the title compound. $^1$H NMR (300 MHz, DMSO-d$_6$) δ 6.28-6.73 (m, 1 H), 7.64-7.74 (m, 1 H), 7.98 (dd, J=9.5, 2.7 Hz, 1 H), 8.14 (d, J=2.4 Hz, 1 H), 8.49-8.56 (m, 1H), 8.89 (dd, J=4.7, 1.7 Hz, 1 H), 9.32 (d, J=1.4 Hz, 1 H), 12.17 (s, 1 H) ppm; MS (DCI/NH$_3$) m/z 241 (M+H)$^+$, 258 (M+NH$_4$)$^+$.

EXAMPLE 56

5-(3-(pyridin-3-yl)-1,2,4-oxadiazol-5-yl)pyridin-2(1H)-one

The title compound was prepared according to the procedure of Example 55 using the product of Example 54. $^1$H NMR (300 MHz, DMSO-d$_6$) δ 6.55 (d, J=9.2 Hz, 1 H), 7.63 (dd, J=7.6, 5.3 Hz, 1 H), 8.05 (dd, J=9.8, 2.7 Hz, 1 H), 8.31-8.47 (m, 2 H), 8.80 (d, J=3.4 Hz, 1 H), 9.22 (s, 1 H), 12.41 (s, 1 H) ppm; MS (DCI/NH$_3$) m/z 241 (M+H)$^+$, 258 (M+NH$_4$)$^+$.

EXAMPLE 57

N-methyl-3-(3-(pyridin-3-yl)-1,2,4-oxadiazol-5-yl)benzenesulfonamide

EXAMPLE 57A 3-(N-methylsulfamoyl)benzoic acid

The title compound was prepared according to the procedure of Example 50A using 3-(chlorosulfonyl)benzoic acid (Aldrich) and methylamine (Aldrich). $^1$H NMR (300 MHz, CD$_3$OD) δ 2.54 (s, 3 H), 7.70 (t, J=7.8 Hz, 1 H), 8.02-8.07 (m, 1 H), 8.23-8.28 (m, 1 H), 8.45 (t, J=1.9 Hz, 1 H) ppm; MS (DCI/NH$_3$) m/z 233 (M+NH$_4$)$^+$.

EXAMPLE 57B

N-methyl-3-(3-(pyridin-3-yl)-1,2,4-oxadiazol-5-yl)benzenesulfonamide

The title compound was prepared according to the procedure of Example 8 using N'-hydroxynicotinimidamide (Aldrich) and the product of Example 57A. $^1$H NMR (300 MHz, CD$_3$OD) δ 2.60 (s, 3 H), 7.65 (ddd, J=8.1, 5.0, 0.8 Hz, 1 H), 7.87 (t, J=8.1 Hz, 1 H), 8.15 (ddd, J=8.0, 1.9, 1.0 Hz, 1 H), 8.48 (ddd, J=7.8, 1.7, 1.0 Hz, 1 H), 8.58 (dt, J=8.1, 1.9 Hz, 1 H), 8.67 (t, J=1.5 Hz, 1 H), 8.75 (dd, J=4.7, 1.7 Hz, 1 H), 9.31 (dd, J=2.2, 0.8 Hz, 1 H) ppm; MS (DCI/NH$_3$) m/z 317 (M+H)$^+$.

EXAMPLE 58

3-(3-(pyridin-3-yl)-1,2,4-oxadiazol-5-yl)aniline dihydrochloride

EXAMPLE 58A 3-(3-(pyridin-3-yl)-1,2,4-oxadiazol-5-yl)aniline

The title compound was prepared according to the procedure of Example 46 using the product of Example 40. $^1$H NMR (300 MHz, DMSO-d$_6$) δ ppm 5.60 (s, 2 H), 6.84-6.93 (m, 1 H), 7.24-7.33 (m, 2 H), 7.41 (d, J=1.7 Hz, 1 H), 7.60-7.67 (m, 1 H), 8.38-8.45 (m, 1 H), 8.81 (dd, J=5.1, 1.7 Hz, 1 H), 9.23 (d, J=2.4 Hz, 1 H) ppm; MS (DCI/NH$_3$) m/z 239 (M+H)$^+$, 256 (M+NH$_4$)$^+$.

EXAMPLE 58B 3-(3-(pyridin-3-yl)-1,2,4-oxadiazol-5-yl)aniline dihydrochloride A solution of the product of Example 58A (60 mg, 0.25 mmol) in ethyl acetate (2 mL) was stirred with hydrochloric acid (Aldrich, 4 M in dioxane, 0.14 mL, 0.55 mmol) at ambient temperature for 4 hours. The title compound was collected by filtration and dried under vacuum. $^1$H NMR (300 MHz, DMSO-d$_6$) δ 7.44 (d, J=7.9 Hz, 1 H), 7.62 (t, J=7.9 Hz, 1 H), 7.80 (dd, J=7.9, 5.2 Hz, 1 H), 7.85-7.96 (m, 2 H), 8.60 (d, J=7.9 Hz, 1 H), 8.90 (d, J=4.8 Hz, 1 H), 9.31 (s, 1 H) ppm; MS (DCI/NH$_3$) m/z 239 (M+H)$^+$, 256 (M+NH$_4$)$^+$.

EXAMPLE 59

(3-(3-(pyridin-3-yl)-1,2,4-oxadiazol-5-yl)phenyl)methanamine bis(hydrochloric acid)

A solution of the product of Example 62 (120 mg, 0.34 mmol) in ethyl acetate (5 mL) was stirred with hydrochloric acid (Aldrich, 4 M in dioxane, 0.5 mL, 2.0 mmol) at ambient temperature for 4 hours. The precipitate was collected by filtration and dried under vacuum to give the title compound. $^1$H NMR (300 MHz, DMSO-d$_6$) δ 4.21 (q, J=5.9 Hz, 2 H), 7.65-7.79 (m, 2 H), 7.86 (dt, J=8.0, 1.3 Hz, 1 H), 8.24 (dt, J=7.7, 1.4 Hz, 1 H), 8.35-8.45 (m, 3 H), 8.48 (dt, J=8.1, 1.9 Hz, 1 H), 8.85 (dd, J=4.9, 1.2 Hz, 1 H), 9.28 (d, J=1.4 Hz, 1 H) ppm; MS (DCI/NH$_3$) m/z 253 (M+H)$^+$.

EXAMPLE 60

5-(2-chloropyridin-4-yl)-3-(pyridin-3-yl)-1,2,4-oxadiazole

The title compound was prepared according to the procedure of Example 1 using N'-hydroxynicotinimidamide (Aldrich) and 2-chloroisonicotinoyl chloride (Maybridge). $^1$H NMR (300 MHz, DMSO-$d_6$) δ 7.68 (ddd, J=7.9, 4.8, 0.8 Hz, 1 H), 8.16 (dd, J=5.1, 1.4 Hz, 1 H), 8.23 (dd, J=1.5, 0.8 Hz, 1 H), 8.42-8.54 (m, 1 H), 8.77 (dd, J=5.1, 0.7 Hz, 1 H), 8.84 (dd, J=4.7, 1.7 Hz, 1 H), 9.28 (dd, J=2.2, 0.8 Hz, 1 H) ppm; MS (DCI/NH$_3$) m/z 259 (M+H)$^+$, 261 (M+H)$^+$.

EXAMPLE 61

4-(3-(pyridin-3-yl)-1,2,4-oxadiazol-5-yl)pyridin-2(1H)-one hydrochloric acid The title compound was prepared according to the procedure of Example 44 using the product of Example 60. $^1$H NMR (300 MHz, DMSO-$d_6$) δ 6.81 (dd, J=6.6, 1.9 Hz, 1 H), 7.09-7.14 (m, 1 H), 7.67-7.76 (m, 2 H), 8.51 (dt, J=8.0, 1.9, 1.7 Hz, 1 H), 8.86 (dd, J=4.9, 1.5 Hz, 1 H), 9.28 (d, J=1.4 Hz, 1 H) ppm; MS (DCI/NH$_3$) m/z 241 (M+H)$^+$.

EXAMPLE 62 tert-butyl 3-(3-(pyridin-3-yl)-1,2,4-oxadiazol-5-yl)benzylcarbamate

The title compound was prepared according to the procedure of Example 8 using N'-hydroxynicotinimidamide (Aldrich) and 3-((tert-butoxycarbonylamino)methyl)benzoic acid (Fluka). $^1$H NMR (300 MHz, DMSO-$d_6$) δ 1.42 (s, 9 H), 4.27 (d, J=6.1 Hz, 2 H), 7.51-7.72 (m, 4 H), 8.01-8.17 (m, 2 H), 8.45 (dt, J=8.1, 1.9 Hz, 1 H), 8.82 (dd, J=5.1, 1.7 Hz, 1H), 9.26 (dd, J=2.2, 0.8 Hz, 1 H) ppm; MS (DCI/NH$_3$) m/z 353 (M+H)$^+$.

EXAMPLE 63

5-(3-bromophenyl)-3-(pyridin-3-yl)-1,2,4-oxadiazole

The title compound was prepared according to the procedure of Example 1 using N'-hydroxynicotinimidamide (Aldrich) and 3-bromobenzoyl chloride (Aldrich). $^1$H NMR (300 MHz, DMSO-$d_6$) δ 7.60-7.71 (m, 2 H), 7.98 (ddd, J=8.1, 2.0, 1.0 Hz, 1 H), 8.22 (ddd, J=7.4, 1.6, 1.3 Hz, 1 H), 8.35 (t, J=1.8 Hz, 1 H), 8.46 (dt, J=7.9, 2.0 Hz, 1 H), 8.83 (dd, J=4.8, 1.6 Hz, 1 H), 9.27 (dd, J=2.4, 0.8 Hz, 1 H) ppm; MS (DCI/NH$_3$) m/z 302 (M+H)$^+$, 304 (M+H)$^+$.

EXAMPLE 64

1-(3-(3-(pyridin-3-yl)-1,2,4-oxadiazol-5-yl)phenyl)pyrrolidin-2-one

A solution of the product of Example 63 (200 mg, 0.66 mmol) and pyrrolidin-2-one (Aldrich, 85 mg, 0.99 mmol) in toluene (anhydrous 10 mL) was degassed and purged with nitrogen three times, cesium carbonate (Aldrich, 324 mg, 0.993 mmol) and tris(dibenzylideneacetone)dipalladium(0) (Aldrich, 12.1 mg, 0.013 mmol), 4,5-bis(diphenylphosphino)-9,9-dimethylxanthene (Aldrich, 23.0 mg, 0.040 mmol, xantphos) were added, degassed and purged with nitrogen three times. The mixture was then heated to 100° C. and stirred under nitrogen for 15 hours. It was then cooled to ambient temperature and diluted with ethyl acetate (50 mL), washed with brine (2×5 mL), concentrated, purified with chromatography (v. ethyl acetate/hexane=1/1, R$_f$=0.1) to give the title compound. $^1$H NMR (300 MHz, DMSO-$d_6$) δ 2.04-2.19 (m, 2 H), 2.57 (t, J=7.9 Hz, 2 H), 3.95 (t, J=6.9 Hz, 2 H), 7.60-7.75 (m, 2 H), 7.84-8.10 (m, 2 H), 8.46 (dt, J=7.9, 2.0 Hz, 1 H), 8.64 (t, J=2.0 Hz, 1 H), 8.82 (dd, J=5.0, 1.8 Hz, 1 H), 9.26 (dd, J=2.4, 0.8 Hz, 1 H) ppm; MS (DCI/NH$_3$) m/z 307 (M+H)$^+$.

EXAMPLE 65 tert-butyl 3-(3-(pyridin-3-yl)-1,2,4-oxadiazol-5-yl)phenylcarbamate

The title compound was prepared according to the procedure of Example 8 using N'-hydroxynicotinimidamide (Aldrich) and 3-(tert-butoxycarbonylamino)benzoic acid (Aldrich). $^1$H NMR (300 MHz, CDCl$_3$) δ 1.56 (s, 9 H), 6.71 (s, 1 H), 7.39-7.58 (m, 2 H), 7.68 (d, J=7.9 Hz, 1 H), 7.89 (d, J=9.1 Hz, 1 H), 8.24 (s, 1 H), 8.45 (d, J=7.9 Hz, 1 H), 8.77 (d, J=4.8 Hz, 1 H), 9.40 (s, 1 H) ppm; MS (DCI/NH$_3$) m/z 339 (M+H)$^+$, 356 (M+NH$_4$)$^+$.

EXAMPLE 66

N,N-dimethyl-1-(3-(3-(pyridin-3-yl)-1,2,4-oxadiazol-5-yl)phenyl)methanamine, bishydrochloric acid salt The free base of the title compound was prepared according to the procedure of Example 8 using N'-hydroxynicotinimidamide (Aldrich) and 3-((dimethylamino)methyl)benzoic acid (Aldrich). A solution of this free base in ethyl acetate (5 mL) was treated with hydrochloric acid (Aldrich, 0.5 mL, 4M in dioxane) at ambient temperature for 2 hours. The title compound was collected by filtration and dried under vacuum. $^1$H NMR (300 MHz, CD$_3$OD) δ 2.93 (s, 6 H), 4.51 (s, 2 H), 7.82 (t, J=7.8 Hz, 1 H), 7.90 (dt, J=7.8, 1.5 Hz, 1 H), 8.23 (dd, J=8.0, 5.9 Hz, 1 H), 8.42 (dt, J=7.7, 1.4 Hz, 1 H), 8.49 (t, J=1.5 Hz, 1 H), 9.04 (d, J=5.1 Hz, 1 H), 9.21 (dt, J=8.1, 1.7 Hz, 1 H), 9.56 (s, 1 H) ppm; MS (DCI/NH$_3$) m/z 281 (M+H)$^+$.

EXAMPLE 67

5-(3-(piperazin-1-yl)phenyl)-3-(pyridin-3-yl)-1,2,4-oxadiazole bis(hydrochloric acid)

EXAMPLE 67A tert-butyl 4-(3-(3-(pyridin-3-yl)-1,2,4-oxadiazol-5-yl)phenyl)piperazine-1-carboxylate A solution of the product of Example 63 (200 mg, 0.66 mmol) and tert-butyl piperazine-1-carboxylate (Aldrich, 123 mg, 0.66 mmol) in toluene (anhydrous, 10 mL) was degassed and purged with nitrogen three times, sodium t-butoxide (Aldrich, 64 mg, 0.66 mmol) and tris(dibenzylideneacetone)dipalladium(0) (Aldrich, 12.1 mg, 0.013 mmol), 4,5-bis(diphenylphosphino)-9,9-dimethylxanthene (Aldrich, 23.0 mg, 0.040 mmol, xantphos) were added, degassed and purged with nitrogen three times. The mixture was then heated to 100° C. and stirred under nitrogen for 15 hours. It was then cooled to ambient temperature and diluted with ethyl acetate (50 mL), washed with brine (2×5 mL), concentrated, purified with chromatography (v. ethyl acetate/hexane=1/1, $R_f$=0.6) to give the title compound. $^1$H NMR (300 MHz, CD$_3$OD) δ 1.49 (s, 9 H), 3.25-3.30 (m, 4 H), 3.56-3.71 (m, 4 H), 7.31 (ddd, J=8.4, 2.6, 0.8 Hz, 1 H), 7.49 (t, J=8.0 Hz, 1 H), 7.64 (ddd, J=8.0, 4.9, 0.7 Hz, 1 H), 7.70 (dt, J=8.0, 1.1 Hz, 1 H), 7.79 (dd, J=2.4, 1.7 Hz, 1 H), 8.56 (dt, J=7.9, 2.0 Hz, 1 H), 8.74 (dd, J=4.9, 1.5 Hz, 1 H), 9.29 (dd, J=2.2, 0.8 Hz, 1 H) ppm; MS (DCI/NH$_3$) m/z 408 (M+H)$^+$.

EXAMPLE 67B 5-(3-(piperazin-1-yl)phenyl)-3-(pyridin-3-yl)-1,2,4-oxadiazole bis(hydrochloric acid)

The title compound was prepared according to the procedure of Example 59 using the product of Example 67A. $^1$H NMR (300 MHz, CD$_3$OD) δ 3.40-3.48 (m, 4 H), 3.54-3.62 (m, 4 H), 7.42 (ddd, J=8.3, 2.8, 0.8 Hz, 1 H), 7.58 (t, J=8.1 Hz, 1 H), 7.78-7.94 (m, 2 H), 8.24-8.39 (m, 1 H), 9.08 (d, J=5.9 Hz, 1 H), 9.32 (dt, J=8.3, 1.8 Hz, 1 H), 9.59 (d, J=1.6 Hz, 1 H) ppm; MS (DCI/NH$_3$) m/z 308 (M+H)$^+$.

EXAMPLE 68

1-(3-(3-(pyridin-3-yl)-1,2,4-oxadiazol-5-yl)phenyl)ethanone

The title compound was prepared according to the procedure of Example 8 using N'-hydroxynicotinimidamide (Aldrich) and 3-acetylbenzoic acid (Aldrich). $^1$H NMR (300 MHz, CD$_3$OD) δ 2.72 (s, 3 H), 7.66 (ddd, J=8.0, 4.9, 1.0 Hz, 1 H), 7.80 (t, J=8.1 Hz, 1 H), 8.31 (ddd, J=8.1, 1.4, 1.2 Hz, 1 H), 8.47 (ddd, J=8.1, 1.4, 1.2 Hz, 1 H), 8.59 (ddd, J=8.1, 2.0, 1.8 Hz, 1 H), 8.75 (dd, J=5.2, 1.6 Hz, 1 H), 8.81 (t, J=1.4 Hz, 1 H), 9.32 (dd, J=2.4, 0.8 Hz, 1 H) ppm; MS (DCI/NH$_3$) m/z 266 (M+H)$^+$.

EXAMPLE 69

3-(6-chloropyridin-3-yl)-5-(2,3-difluorophenyl)-1,2,4-oxadiazole

The title compound was prepared according to the procedure of Example 1 using the product of Example 53A and 2,3-difluorobenzoyl chloride (Aldrich). $^1$H NMR (300 MHz, DMSO-d$_6$) δ 7.41-7.59 (m, 1 H), 7.76-7.93 (m, 2 H), 8.05 (dd, J=7.8, 6.1 Hz, 1 H), 8.48 (dd, J=8.3, 2.5 Hz, 1 H), 9.08 (d, J=2.4 Hz, 1 H) ppm; MS (DCI/NH$_3$) m/z 294 (M+H)$^+$, 296 (M+H)$^+$.

EXAMPLE 70

3-(6-chloropyridin-3-yl)-5-(3,4-difluorophenyl)-1,2,4-oxadiazole

The title compound was prepared according to the procedure of Example 1 using the product of Example 53A and 3,4-difluorobenzoyl chloride (Aldrich). $^1$H NMR (300 MHz, DMSO-d$_6$) δ ppm 7.70-7.83 (m, 2 H), 8.03-8.15 (m, 1 H), 8.22-8.36 (m, 1 H), 8.48 (dd, J=8.1, 2.4 Hz, 1 H), 9.08 (d, J=2.4 Hz, 1 H) ppm; MS (DCI/NH$_3$) m/z 294 (M+H)$^+$, 296 (M+H)$^+$.

EXAMPLE 71

(R)-3-(pyridin-3-yl)-5-(3-(pyrrolidin-2-yl)phenyl)-1,2,4-oxadiazole bis(hydrochloric acid)

EXAMPLE 71A (R)-tert-butyl 2-(3-(3-(pyridin-3-yl)-1,2,4-oxadiazol-5-yl)phenyl)pyrrolidine-1-carboxylate Under nitrogen, to a solution of tert-butyl pyrrolidine-1-carboxylate (Aldrich, 0.52 g, 3.00 mmol) and (−)-sparteine (Aldrich, 0.69 g, 3.0 mmol) in t-butyl methyl ether (Aldrich, anhydrous, 10 mL) was added sec-butyllithium (Aldrich, 1.4 M in cyclohexane, 2.2 mL, 3.1 mmol) at −78° C. After the completion of the addition, it was stirred at −78° C. for 3 hours. Zinc chloride (Aldrich, 1 M in diethyl ether, 2.0 mL, 2.0 mmol) was then added slowly and the resultant solution was stirred at −78° C. for additional 30 minutes and then warmed up to ambient temperature, stirred for another 30 minutes at room temperature before the addition of a solution of the product of the Example 63 (0.30 g, 1.0 mmol) in tetrahydrofuran (anhydrous, 5.0 mL) and bis(tri-t-butylphosphine)palladium(0) (Strem, 10.2 mg, 0.02 mmol). The mixture was stirred at ambient temperature for 15 hours and quenched with ammonium hydroxide (5 mL). The mixture was extracted with ethyl acetate (3×20 mL). The combined extracts were concentrated and purified by chromatography (v. hexanes/ethyl acetate=1/1, $R_f$=0.5) to give the title compound. $^1$H NMR (300 MHz, CD$_3$OD) δ 1.19 (s (broad), 6 H), 1.48 (s (broad), 3 H), 1.83-2.00 (m, 2 H), 2.37-2.55 (m, J=8.1, 8.1 Hz, 1 H), 3.57-3.72 (m, 2 H), 4.90-5.14 (m, 1 H), 7.47-7.73 (m, 3 H), 8.00-8.25 (m, 2 H), 8.56 (dt, J=8.3, 1.8 Hz, 1 H), 8.74 (dd, J=5.1, 1.7 Hz, 1 H), 9.29 (dd, J=2.0, 0.7 Hz, 1 H) ppm; MS (DCI/NH$_3$) m/z 393 (M+H)$^+$.

EXAMPLE 71B (R)-3-(Pyridin-3-yl)-5-(3-(pyrrolidin-2-yl)phenyl)-1,2,4-oxadiazole bis(hydrochloric acid)

The title compound was prepared according to the procedure of Example 59 using the product of Example 71A. $^1$H NMR (300 MHz, DMSO-d$_6$) δ 1.98-2.27 (m, 3 H), 2.39-2.50 (m, 1 H), 3.22-3.51 (m, 2 H), 4.55-4.81 (m, 1 H), 7.71-7.82 (m, 2 H), 7.96 (d, J=7.9 Hz, 1 H), 8.26 (dt, J=7.8, 1.2 Hz, 1 H), 8.40 (s, 1 H), 8.58 (dt, J=8.1, 1.9 Hz, 1 H), 8.89 (dd, J=5.2, 1.6 Hz, 1 H), 9.21-9.53 (m, J=1.6 Hz, 2 H) ppm; MS (DCI/NH$_3$) m/z 293 (M+H)$^+$.

EXAMPLE 72

5-(3-(1H-pyrazol-3-yl)phenyl)-3-(pyridin-3-yl)-1,2,4-oxadiazole

The title compound was prepared according to the procedure of Example 8 using N'-hydroxynicotinimidamide (Aldrich) and 3-(1H-pyrazol-3-yl)benzoic acid (Maybridge). $^1$H NMR (300 MHz, DMSO-d$_6$) δ 6.91 (d, J=2.4 Hz, 1 H), 7.62-7.69 (m, 1 H), 7.72 (t, J=7.8 Hz, 1 H), 7.79-7.92 (m, 1 H), 7.82-7.88 (m, 1H), 8.10-8.20 (m, 3 H), 8.49 (dt, J=8.2, 1.9, 1.7 Hz, 1 H), 8.64 (s, 1 H), 8.83 (dd, J=4.7, 1.7 Hz, 1 H), 9.29 (dd, J=2.2, 0.8 Hz, 1 H) ppm; MS (DCI/NH$_3$) m/z 290 (M+H)$^+$.

EXAMPLE 73

1-(3-(3-(pyridin-3-yl)-1,2,4-oxadiazol-5-yl)phenyl) ethanol

A solution of the product of Example 68 (265 mg, 1.0 mmol) in ethanol (5 mL) was stirred with sodium borohydride (Aldrich, 83 mg, 2.2 mmol) at room temperature for 16 hours. The inorganic solid was filtered off with a syringe filter and the liquid mixture was purified by preparative HPLC (Gilson, column, Xbridge® 5 μm, 30×100 mm. eluting solvent, acetonitrile/water (pH=10, $NH_4HCO_3$—$NH_3.H_2O$ buffer), v. 5/95 to 95/5 over 35 minutes, flow rate, 40 mL/minute, uv, 234 nm). Fractions of the desired product were collected and concentrated to give the desired product. $^1$H NMR (300 MHz, $CD_3OD$) δ 1.51 (d, J=6.7 Hz, 3 H), 4.97 (q, J=6.6 Hz, 1 H), 7.57-7.73 (m, 3 H), 8.13 (dt, J=7.6, 1.5 Hz, 1 H), 8.28 (t, J=1.8 Hz, 1 H), 8.57 (dt, J=7.9, 1.8 Hz, 1 H), 8.74 (dd, J=5.0, 1.8 Hz, 1 H), 9.30 (dd, J=2.2, 1.0 Hz, 1 H) ppm; MS ($DCI/NH_3$) m/z 268 (M+H)$^+$.

EXAMPLE 74

3-(3-(6-chloropyridin-3-yl)-1,2,4-oxadiazol-5-yl) benzonitrile

The title compound was prepared according to the procedure of Example 1 using the product of Example 53A and 3-cyanobenzoyl chloride (Aldrich). $^1$H NMR (300 MHz, $CDCl_3$) δ 7.52 (d, J=7.8 Hz, 1 H), 7.75 (t, J=8.0 Hz, 1 H), 7.93 (d, J=7.8 Hz, 1 H), 8.30-8.50 (m, 2 H), 8.54 (s, 1 H), 9.19 (d, J=2.4 Hz, 1 H) ppm; MS ($DCI/NH_3$) m/z 283 (M+H)$^+$, 300 (M+$NH_4$)$^+$.

EXAMPLE 75

3-(4-fluorophenyl)-5-(pyridin-3-yl)-1,2,4-oxadiazole

4-Fluoro-N'-hydroxybenzimidamide (0.154 g, 1 mmol) was dissolved in pyridine (10 mL) and nicotinoyl chloride (Aldrich, 0.141 g, 1 mmol) was added. The reaction mixture was heated to reflux for 3 hours and then cooled to room temperature. The cooled reaction mixture was quenched with water (25 mL) and filtered. The solid was further purified with flash column chromatography (5% methanol/dichloromethane) to give the titled product. $^1$H NMR (300 MHz, DMSO-$d_6$) δ 7.47 (t, J=6.8 Hz, 2 H), 7.74-7.70 (m, 1 H), 8.20-8.15 (m, 2 H), 8.58-8.54 (m, 1 H), 8.91-8.89 (dd, J=1.7, 1.7 Hz, 1 H), 9.35 (d, J=1.4 Hz, 1 H) ppm; MS ($DCI/NH_3$) m/z 242 (M+H)$^+$.

EXAMPLE 76

3-(5-(6-chloropyridin-3-yl)-1,2,4-oxadiazol-3-yl) benzonitrile

The title compound was prepared according to the procedure of Example 4B using 3-cyano-N'-hydroxybenzimidamide (Example 4A) and 6-chloronicotinoyl chloride (Aldrich). $^1$H NMR (300 MHz, DMSO-$d_6$) δ 7.87 (m, 2 H), 8.17 (m, 1 H), 8.4 (m, 1 H), 8.43 (d, J=1.7 Hz, 1 H), 8.6 (m, 1 H), 9.25 (d, J=1.7 Hz, 1 H) ppm; MS ($DCI/NH_3$) m/z 283 (M+H)$^+$.

EXAMPLE 77

3-(5-(2-fluoropyridin-3-yl)-1,2,4-oxadiazol-3-yl) benzonitrile

The title compound was prepared according to the procedure of Example 4B using 3-cyano-N'-hydroxybenzimidamide (Example 4A) and 2-fluoronicotinoyl chloride (Aldrich). $^1$H NMR (300 MHz, DMSO-$d_6$) δ 7.87 (m, 1 H), 7.95 (m, 1 H), 8.17 (m, 1 H), 8.17 (m, 1 H), 8.43 (m, 1 H), 8.6 (m, 1 H), 8.8 (m, 1 H) ppm; MS ($DCI/NH_3$) m/z 267 (M+H)$^+$.

EXAMPLE 78

3-fluoro-5-(5-(pyridin-3-yl)-1,2,4-oxadiazol-3-yl) benzonitrile

The title compound was prepared according to the procedure of Example 4B using 3-cyano-5-fluoro-N'-hydroxybenzimidamide (Prepared from 5-fluoroisophthalonitrile using the procedure described in Example 4A.) and nicotinoyl chloride (Aldrich). $^1$H NMR (300 MHz, DMSO-$d_6$) δ 7.77 (m, 1 H), 8.2 (m, 2 H), 8.4 (m, 1 H), 8.6 (m, 1 H), 8.9 (m, 1 H), 9.4 (m, 1 H) ppm; MS ($DCI/NH_3$) m/z 267 (M+H)$^+$.

EXAMPLE 79

5-(2,3-Difluorophenyl)-3-(pyrimidin-5-yl)-1,2,4-oxadiazole

EXAMPLE 79A

Pyrimidine-5-carboxamide

A solution of ethyl pyrimidine-5-carboxylate (6.10 g, 40.0 mmol) in methanol (40 mL) was stirred with ammonium hydroxide (4.30 mL, 110 mmol) in a sealed tube at 50° C. for 10 hours. The reaction mixture was then concentrated and the residue was stirred in ethanol/ethyl acetate (v/v 1/4, 50 mL) at ambient temperature for 2 hours. The white precipitate was collected by filtration and dried to give the titled compound. $^1$H NMR (300 MHz, DMSO-$d_6$) δ 7.85 [s (broad), 1 H], 8.33 [s (broad), 1 H], 9.18 (s, 2 H), 9.32 (s, 1 H) ppm; MS (DCI/$NH_3$) m/z 124 (M+H)$^+$, 141 (M+$NH_4$)$^+$.

EXAMPLE 79B

Pyrimidine-5-carbonitrile

To a suspension of the product of Example 79A (6.75 g, 54.8 mmol) and triethylamine (Aldrich, 15.28 mL, 110 mmol) in anhydrous $CH_2Cl_2$ (Aldrich, 400 mL) was slowly added a solution of trifluoroacetic anhydride (Aldrich, 9.30 mL, 65.8 mmol) in anhydrous $CH_2Cl_2$ (100 mL) at 0-10° C. over 1 hours. It was then stirred at 0° C. to ambient temperature for 2 hours. The reaction was then quenched with water (10 mL) and washed with NaOH (1 N, 20 mL) and brine (2×10 mL) before being concentrated under reduced pressure at less than 30° C. to supply the titled compound. $^1$H NMR (300 MHz, DMSO-$d_6$) δ 9.34 (s, 2 H), 9.47 (s, 1 H) ppm; MS ($DCI/NH_3$) m/z 123 (M+$NH_4$)$^+$.

EXAMPLE 79C

N'-Hydroxypyrimidine-5-carboximidamide

A solution of the product of Example 79B (5.47 g, 52 mmol) and aqueous hydroxylamine (Aldrich, 50%, 2.3 mL, 78 mmol) in methanol (50 mL) was stirred at 65° C. for 1 hour and then concentrated under reduced pressure to remove the volatiles. The residue was triturated with EtOAc (30 mL). The precipitates were collected by filtration and dried to give the titled compound. $^1$H NMR (300 MHz, DMSO-$d_6$) δ 6.14 (s, 2 H), 9.03 (s, 2 H), 9.18 (s, 1 H), 10.06 (s, 1 H) ppm; MS (DCI/NH$_3$) m/z 139 (M+H)$^+$, 156 (M+NH$_4$)$^+$.

EXAMPLE 79D 5-(2,3-Difluorophenyl)-3-(pyrimidin-5-yl)-1,2,4-oxadiazole

The titled compound was prepared according to the procedure of Method D using the product of Example 79C and 2,3-difluorobenzoyl chloride (Aldrich). $^1$H NMR (300 MHz, CDCl$_3$) δ 7.27-7.39 (m, 1 H), 7.42-7.56 (m, 1 H), 7.95-8.08 (m, 1 H), 9.39 (s, 1 H), 9.49 (s, 2 H) ppm; MS (DCI/NH$_3$) m/z 261 (M+H)$^+$.

EXAMPLE 80

5-(pyridin-3-yl)-3-(pyrimidin-5-yl)-1,2,4-oxadiazole

The titled compound was prepared according to the procedure of Method D using the product of Example 79C and nicotinoyl chloride hydrochloride (Aldrich). $^1$H NMR (300 MHz, DMSO-$d_6$) δ 7.74 (ddd, J=8.0, 4.9, 0.7 Hz, 1 H), 8.54-8.64 (m, 1 H), 8.93 (dd, J=4.9, 1.5 Hz, 1 H), 9.39 (d, J=1.7 Hz, 1 H), 9.45 (s, 1 H), 9.46 (s, 2 H) ppm; MS (DCI/NH$_3$) m/z 226 (M+H)$^+$.

EXAMPLE 81

2-fluoro-N,N-dimethyl-4-(3-(pyrimidin-5-yl)-1,2,4-oxadiazol-5-yl)aniline

The titled compound was prepared according to the procedure of Method C using the product of Example 79C and 3,4-difluorobenzoic acid (Aldrich). $^1$H NMR (300 MHz, CDCl$_3$) δ 3.06 (s, 3 H), 3.07 (s, 3 H), 6.89 (t, J=8.7 Hz, 1 H), 7.76-7.96 (m, 2 H), 9.36 (s, 1 H), 9.43-9.47 (m, 2 H) ppm; MS (DCI/NH$_3$) m/z 286 (M+H)$^+$.

EXAMPLE 82

3-(3-(pyrimidin-5-yl)-1,2,4-oxadiazol-5-yl)benzonitrile

The titled compound was prepared according to the procedure of Method D using the product of Example 79C and 3-cyanobenzoyl chloride (Aldrich). $^1$H NMR (300 MHz, DMSO-$d_6$) δ 7.91 (t, J=7.9 Hz, 1 H), 8.24 (dt, J=7.7, 1.4, 1.2 Hz, 1 H), 8.53 (dt, J=8.1, 1.4, 1.2 Hz, 1 H), 8.67 (t, J=1.8 Hz, 1 H), 9.45 (s, 1 H), 9.46 (s, 2 H) ppm; MS (DCI/NH$_3$) m/z 250 (M+H)$^+$.

EXAMPLE 83

5-(3,4-Difluorophenyl)-3-(pyridazin-4-yl)-1,2,4-oxadiazole hydrochloride

EXAMPLE 83A

Methyl pyridazine-4-carboxylate

To a solution of pyridazine-4-carboxylic acid (Aldrich, 5.0 g, 40.3 mmol) in methanol (anhydrous, Aldrich, 100 mL) was added sulfuric acid (concentrated, Aldrich, 2 mL). The reaction mixture was then heated to reflux and stirred for 16 hours. The volatiles were removed under reduced pressure. The residue was basified to pH=8-9 with saturated sodium carbonate (20 mL) and then extracted with EtOAc (3×100 mL). The combined extracts were washed with brine (2×20 mL) and dried over magnesium sulfate. The drying agent was filtered off and the organic solution was concentrated and dried to give the titled compound. $^1$H NMR (300 MHz, DMSO-$d_6$) δ 3.34 (s, 3 H), 8.10 (dd, J=5.2, 2.4 Hz, 1 H), 9.52 (dd, J=5.2, 1.2 Hz, 1 H), 9.58 (dd, J=2.2, 1.4 Hz, 1 H) ppm; MS (DCI/NH$_3$) m/z 139 (M+H)$^+$.

EXAMPLE 83B pyridazine-4-carboxamide

The title compound was prepared according to the procedure of Example 79A using the product of Example 83A and ammonium hydroxide (Aldrich). $^1$H NMR (300 MHz, DMSO-$d_6$) δ 8.00 (dd, J=5.2, 2.4 Hz, 1 H), 8.46 [s (broad), 2H], 9.44 (dd, J=5.2, 1.2 Hz, 1 H), 9.55 (dd, J=2.2, 1.4 Hz, 1 H) ppm; MS (DCI/NH$_3$) m/z 124 (M+H)$^+$, 141 (M+NH$_4$)$^+$.

EXAMPLE 83C pyridazine-4-carbonitrile

The title compound was prepared according to the procedure of Example 79B using the product of Example 83B and trifluoroacetic anhydride (Aldrich). $^1$H NMR (300 MHz, DMSO-$d_6$) δ 8.28 (dd, J=5.4, 2.2 Hz, 1 H), 9.57 (dd, J=5.2, 1.2 Hz, 1 H), 9.66 (dd, J=2.2, 1.4 Hz, 1 H) ppm; MS (DCI/NH$_3$) m/z 123 (M+NH$_4$)$^+$.

EXAMPLE 83D

N'-Hydroxypyridazine-4-carboximidamide

The title compound was prepared according to the procedure of Example 79C using the product of Example 83C and hydroxylamine (Aldrich). $^1$H NMR (300 MHz, DMSO-$d_6$) δ 6.19 (s, 2 H), 7.87 (dd, J=5.4, 2.4 Hz, 1 H), 9.25 (dd, J=5.4, 1.4 Hz, 1 H), 9.46 (dd, J=2.4, 1.4 Hz, 1 H), 10.36 (s, 1 H) ppm; MS (DCI/NH$_3$) m/z 139 (M+H)$^+$, 156 (M+NH$_4$)$^+$.

EXAMPLE 83E 5-(3,4-difluorophenyl)-3-(pyridazin-4-yl)-1,2,4-oxadiazole

The titled compound was prepared according to the procedure of Method D using the product of Example 83D and 3,4-difluorobenzoyl chloride (Aldrich). $^1$H NMR (300 MHz, DMSO-$d_6$) δ 7.80 (dt, J=10.5, 8.3 Hz, 1 H), 8.08-8.19 (m, 1 H), 8.29 (dd, J=5.4, 2.4 Hz, 1 H), 8.31-8.38 (m, 1 H), 9.55 (dd, J=5.4, 1.4 Hz, 1 H), 9.82 (dd, J=2.2, 1.2 Hz, 1 H) ppm; MS (DCI/NH$_3$) m/z 261 (M+H)$^+$.

EXAMPLE 83F 5-(3,4-Difluorophenyl)-3-(pyridazin-4-yl)-1,2,4-oxadiazole hydrochloride A solution of the product of Example 83E (140 mg, 0.54 mmol) in ethyl acetate (5.0 mL) was stirred with hydrochloric acid (Aldrich, 4 M in dioxane, 0.25 mL, 1.0 mmol) at ambient temperature for 10 hours. The white precipitates were collected by filtration and dried to give the title compound. $^1$H NMR (300 MHz, DMSO-d$_6$) δ 7.81 (dt, J=10.5, 8.5 Hz, 1 H), 8.08-8.19 (m, 1 H), 8.26-8.39 (m, 2 H), 9.55 (dd, J=5.4, 1.4 Hz, 1 H), 9.83 (dd, J=2.4, 1.4 Hz, 1 H) ppm; MS (DCI/NH$_3$) m/z 261 (M+H)$^+$.

EXAMPLE 84

3-(Pyridazin-4-yl)-5-(pyridin-3-yl)-1,2,4-oxadiazole

The titled compound was prepared according to the procedure of Method D using the product of Example 83D and nicotinoyl chloride hydrochloride (Aldrich). $^1$H NMR (300 MHz, DMSO-d$_6$) δ 7.75 (ddd, J=8.0, 4.9, 0.7 Hz, 1 H), 8.32 (dd, J=5.3, 2.2 Hz, 1 H), 8.61 (dt, J=8.2, 1.8 Hz, 1 H), 8.93 (dd, J=5.1, 1.7 Hz, 1 H), 9.39 (dd, J=2.2, 0.8 Hz, 1 H), 9.55 (dd, J=5.4, 1.4 Hz, 1 H), 9.85 (dd, J=2.2, 1.2 Hz, 1 H) ppm; MS (DCI/NH$_3$) m/z 226 (M+H)$^+$.

EXAMPLE 85

N,N-Dimethyl-N'-(4-(3-(pyrimidin-5-yl)-1,2,4-oxadiazol-5-yl)phenylsulfonyl)formimidamide The titled compound was prepared according to the procedure of Method D using the product of Example 79C and 4-sulfamidobenzoyl chloride dimethylformamide complex (Alfa Aesar). $^1$H NMR (300 MHz, DMSO-d$_6$) δ 2.94 (s, 3 H), 3.18 (s, 3 H), 8.06 (d, J=8.8 Hz, 2 H), 8.30 (s, 1 H), 8.37 (d, J=8.8 Hz, 2 H), 9.45 (s, 1H), 9.46 (s, 2 H) ppm; MS (DCI/NH$_3$) m/z=359 (M+H)$^+$, 376 (M+NH$_4$)$^+$.

EXAMPLE 86

5-(4-fluorophenyl)-3-(pyrimidin-5-yl)-1,2,4-oxadiazole

The titled compound was prepared according to the procedure of Method D using the product of Example 79C and 4-fluorobenzoyl chloride (Aldrich). $^1$H NMR (300 MHz, DMSO-d$_6$) δ 7.51-7.59 (m, 2 H), 8.27-8.34 (m, 2 H), 9.44 (s, 2 H), 9.45 (S, 1H) ppm; MS (DCI/NH$_3$) m/z=243 (M+H)$^+$, 260 (M+NH$_4$)$^+$.

EXAMPLE 87

5-(3-fluorophenyl)-3-(pyrimidin-5-yl)-1,2,4-oxadiazole

The titled compound was prepared according to the procedure of Method D using the product of Example 79C and 3-fluorobenzoyl chloride (Aldrich). $^1$H NMR (300 MHz, DMSO-d$_6$) δ 7.61-7.71 (m, 1 H), 7.72-7.84 (m, 1 H), 8.04 (ddd, J=9.3, 2.5, 1.4 Hz, 1 H), 8.07-8.12 (m, 1 H), 9.45 (s, 3 H) ppm; MS (DCI/NH$_3$) m/z=243 (M+H)$^+$, 260 (M+NH$_4$)$^+$.

EXAMPLE 88

3-(pyrimidin-5-yl)-5-(3,4,5-trifluorophenyl)-1,2,4-oxadiazole

The titled compound was prepared according to the procedure of Method D using the product of Example 79C and 3,4,5-trifluorobenzoyl chloride (Aldrich). $^1$H NMR (300 MHz, DMSO-d$_6$) δ 8.24 (dd, J=8.0, 6.6 Hz, 2 H), 9.44 (s, 2 H), 9.46 (s, 1 H) ppm; MS (DCI/NH$_3$) m/z=279 (M+H)$^+$, 296 (M+NH$_4$)$^+$.

EXAMPLE 89

5-(2-Chloropyridin-4-yl)-3-(pyrimidin-5-yl)-1,2,4-oxadiazole

The titled compound was prepared according to the procedure of Method D using the product of Example 79C and 2-chloroisonicotinoyl chloride (Maybridge). $^1$H NMR (300 MHz, DMSO-d$_6$) δ 8.17 (dd, J=5.1, 1.4 Hz, 1 H), 8.25 (dd, J=1.4, 0.7 Hz, 1 H), 8.78 (dd, J=5.1, 0.7 Hz, 1 H), 9.46 (s, 1 H), 9.47 (s, 2 H) ppm; MS (DCI/NH$_3$) m/z=260 (M+H)$^+$, 262 (M+H)$^+$.

EXAMPLE 90

3-(Pyridin-3-yl)-5-(pyrimidin-5-yl)-1,2,4-oxadiazole

The titled compound was prepared according to the procedure of Method C using N'-hydroxynicotinimidamide (Tyger) and pyrimidine-5-carboxylic acid (Maybridge). $^1$H NMR (300 MHz, DMSO-d$_6$) δ 7.68 (ddd, J=8.0, 4.9, 1.0 Hz, 1 H), 8.48 (dt, J=7.7, 2.1 Hz, 1 H), 8.84 (dd, J=4.7, 1.7 Hz, 1 H), 9.29 (dd, J=2.4, 1.0 Hz, 1 H), 9.51 (s, 1 H), 9.56 (s, 2 H) ppm; MS (DCI/NH$_3$) m/z=226 (M+H)$^+$, 243 (M+NH$_4$)$^+$.

EXAMPLE 91

5-(Pyridazin-4-yl)-3-(pyridin-3-yl)-1,2,4-oxadiazole

The titled compound was prepared according to the procedure of Method C using N'-hydroxynicotinimidamide (Aldrich) and pyridazine-4-carboxylic acid (Aldrich). $^1$H NMR (300 MHz, CD$_3$OD) δ 7.67 (ddd, J=8.1, 5.0, 0.8 Hz, 1 H), 8.45 (dd, J=5.4, 2.4 Hz, 1 H), 8.60 (dt, J=8.1, 1.9 Hz, 1 H), 8.78 (dd, J=5.1, 1.7 Hz, 1 H), 9.34 (dd, J=2.2, 0.8 Hz, 1 H), 9.55 (dd, J=5.4, 1.4 Hz, 1 H), 9.94 (dd, J=2.2, 1.2 Hz, 1 H) ppm; MS (DCI/NH$_3$) m/z=226 (M+H)$^+$.

EXAMPLE 92

3-(3-(Pyridazin-4-yl)-1,2,4-oxadiazol-5-yl)benzonitrile

The titled compound was prepared according to the procedure of Method D using the product of Example 83D and 3-cyanobenzoyl chloride (Aldrich). $^1$H NMR (300 MHz, CD$_3$OD) δ 7.86 (t, J=7.9 Hz, 1 H), 8.09 (ddd, J=8.1, 1.4, 1.2 Hz, 1 H), 8.40 (dd, J=5.4, 2.2 Hz, 1 H), 8.55 (dt, J=7.9, 1.6 Hz, 1 H), 8.64 (t, J=2.0 Hz, 1 H), 9.46 (dd, J=5.4, 1.4 Hz, 1 H), 9.88 (dd, J=2.2, 1.4 Hz, 1 H) ppm; MS (DCI/NH$_3$) m/z=250 (M+H)$^+$.

EXAMPLE 93

5-(3-Fluorophenyl)-3-(pyridazin-4-yl)-1,2,4-oxadiazole

The titled compound was prepared according to the procedure of Method D using the product of Example 83D and 3-fluorobenzoyl chloride (Aldrich). $^1$H NMR (300 MHz, CD$_3$OD) δ 7.45-7.53 (m, 1 H), 7.69 (td, J=8.1, 5.6 Hz, 1 H), 8.00 (ddd, J=9.1, 2.6, 1.4 Hz, 1 H), 8.11 (dt, J=7.9, 1.2 Hz, 1

H), 8.39 (dd, J=5.4, 2.2 Hz, 1 H), 9.45 (dd, J=5.2, 1.2 Hz, 1 H), 9.87 (dd, J=2.2, 1.4 Hz, 1 H) ppm; MS (DCI/NH$_3$) m/z=243 (M+H)$^+$.

EXAMPLE 94

3-(Pyridazin-4-yl)-5-(3,4,5-trifluorophenyl)-1,2,4-oxadiazole

The titled compound was prepared according to the procedure of Method D using the product of Example 83D and 3,4,5-trifluorobenzoyl chloride (Aldrich). $^1$H NMR (300 MHz, CD$_3$OD) δ 8.04-8.16 (m, 2 H), 8.38 (dd, J=5.4, 2.2 Hz, 1 H), 9.46 (dd, J=5.4, 1.4 Hz, 1 H), 9.86 (dd, J=2.4, 1.2 Hz, 1 H) ppm; MS (DCI/NH$_3$) m/z=279 (M+H)$^+$.

EXAMPLE 95

5-(3,5-difluorophenyl)-3-(pyridazin-4-yl)-1,2,4-oxadiazole

The titled compound was prepared according to the procedure of Method D using the product of Example 83D and 3,5-difluorobenzoyl chloride (Aldrich). $^1$H NMR (300 MHz, CD$_3$OD) δ 7.40 (tt, J=8.9, 2.4 Hz, 1 H), 7.85-7.94 (m, 2 H), 8.39 (dd, J=5.4, 2.2 Hz, 1 H), 9.46 (dd, J=5.4, 1.4 Hz, 1 H), 9.87 (dd, J=2.2, 1.4 Hz, 1 H) ppm; MS (DCI/NH$_3$) m/z=261 (M+H)$^+$.

EXAMPLE 96

5-(4-fluorophenyl)-3-(pyridazin-4-yl)-1,2,4-oxadiazole

The titled compound was prepared according to the procedure of Method D using the product of Example 83D and 4-fluorobenzoyl chloride (Aldrich). $^1$H NMR (300 MHz, CD$_3$OD) δ 7.36-7.45 (m, 2 H), 8.29-8.40 (m, 3 H), 9.45 (dd, J=5.6, 1.2 Hz, 1 H), 9.86 (dd, J=2.4, 1.2 Hz, 1 H) ppm; MS (DCI/NH$_3$) m/z=243 (M+H)$^+$.

EXAMPLE 97

3-(pyridazin-4-yl)-5-(pyrimidin-5-yl)-1,2,4-oxadiazole

The titled compound was prepared according to the procedure of Method C using the product of Example 83D and pyrimidine-5-carboxylic acid (Maybridge). $^1$H NMR (300 MHz, CD$_3$OD) δ 8.41 (dd, J=5.4, 2.4 Hz, 1 H), 9.44 (s, 1 H), 9.47 (dd, J=5.4, 1.4 Hz, 1 H), 9.59 (s, 2 H), 9.90 (dd, J=2.2, 1.2 Hz, 1 H) ppm; MS (DCI/NH$_3$) m/z=227 (M+H)$^+$.

EXAMPLE 98

3-(pyridazin-4-yl)-5-(2,36-trifluorophenyl)-1,2,4-oxadiazole

The titled compound was prepared according to the procedure of Method D using the product of Example 83D and 2,3,6-trifluorobenzoyl chloride (Aldrich). $^1$H NMR (300 MHz, CD$_3$OD) δ 7.28-7.37 (m, J=9.5, 9.5, 3.7, 2.4 Hz, 1 H), 7.67-7.79 (m, J=9.6, 9.6, 8.7, 4.9 Hz, 1 H), 8.39 (dd, J=5.3, 2.2 Hz, 1 H), 9.46 (dd, J=5.3, 1.2 Hz, 1 H), 9.88 (dd, J=2.2, 1.2 Hz, 1 H) ppm; MS (DCI/NH$_3$) m/z=279 (M+H)$^+$.

EXAMPLE 99

3-(pyridazin-4-yl)-5-(2,3,4-trifluorophenyl)-1,2,4-oxadiazole

The titled compound was prepared according to the procedure of Method D using the product of Example 83D and 2,3,4-trifluorobenzoyl chloride (Aldrich). $^1$H NMR (300 MHz, CD$_3$OD) δ 7.40-7.50 (m, J=9.3, 9.3, 7.0, 2.2 Hz, 1 H), 8.10-8.20 (m, 1 H), 8.39 (dd, J=5.4, 2.4 Hz, 1 H), 9.46 (dd, J=5.3, 1.2 Hz, 1 H), 9.87 (dd, J=2.2, 1.2 Hz, 1 H) ppm; MS (DCI/NH$_3$) m/z=279 (M+H)$^+$.

EXAMPLE 100

N,N-dimethyl-N'-(4-(3-(pyridazin-4-yl)-1,2,4-oxadiazol-5-yl)phenylsulfonyl)formimidamide The titled compound was prepared according to the procedure of Method D using the product of Example 83D and 4-sulfamidobenzoyl chloride dimethylformamide complex (Alfa Aesar). $^1$H NMR (300 MHz, CD$_3$OD) δ 2.95 (s, 3H), 3.18 (s, 3 H), 8.06 (d, J=8.5 Hz, 2 H), 8.29 (s, 1 H), 8.31 (dd, J=5.3, 2.2 Hz, 1 H), 8.37 (d, J=8.8 Hz, 2 H), 9.54 (dd, J=5.1, 1.4 Hz, 1 H), 9.83 (dd, J=2.4, 1.4 Hz, 1 H) ppm; MS (DCI/NH$_3$) m/z=359 (M+H)$^+$.

EXAMPLE 101

5-(3,4-difluorophenyl)-3-(pyrimidin-5-yl)-1,2,4-oxadiazole tosylate

EXAMPLE 101A 5-(3,4-Difluorophenyl)-3-(pyrimidin-5-yl)-1,2,4-oxadiazole

The titled compound was prepared according to the procedure of Method D using the product of Example 79C and 3,4-difluorobenzoyl chloride (Aldrich). $^1$H NMR (300 MHz, CDCl$_3$) δ 7.35-7.48 (m, 1 H), 7.97-8.13 (m, 2 H), 9.40 (s, 1 H), 9.49 (s, 2 H) ppm; MS (DCI/NH$_3$) m/z 261 (M+H)$^+$.

EXAMPLE 101B 5-(3,4-Difluorophenyl)-3-(pyrimidin-5-yl)-1,2,4-oxadiazole tosylate A solution of the product of Example 101A (52 mg, 0.2 mmol) in ethyl acetate (5 mL) was stirred with a solution of p-toluenesulfonic acid monohydrate (Aldrich, 46.0 mg, 0.24 mmol) in ethyl acetate (1.0 mL) at ambient temperature for 10 hours. The precipitates were collected by filtration and dried to give the title compound. $^1$H NMR (300 MHz, CDCl$_3$) δ 2.40 (s, 3 H), 7.25 (d, J=8.2 Hz, 2 H), 7.36-7.53 (m, 1 H), 7.83 (d, J=8.3 Hz, 2 H), 8.03-8.12 (m, 2 H), 9.57 (s, 1 H), 9.71 (s, 2 H); MS (DCI/NH$_3$) m/z 261 (M+H)$^+$.

EXAMPLE 102

3-(3,4-difluorophenyl)-5-(pyrimidin-5-yl)-1,2,4-oxadiazole

The titled compound was prepared according to the procedure of Method D using 3,4-difluoro-N'-hydroxybenzimidamide (Tyger) and pyrimidine-5-carbonyl chloride. The pyrimidine-5-carbonyl chloride was prepared by the reaction of pyrimidine-5-carboxylic acid (Maybridge, 138 mg, 1.0 mmol) with oxalyl chloride (Aldrich, 2 M, in CH$_2$Cl$_2$, 1.0 mL, 2.0 mmol) and a drop of dimethylformamide at room temperature over 1 hour with subsequent removal of volatiles under reduced pressure. $^1$H NMR (300 MHz, DMSO-d$_6$) δ 7.72 (dt, J=10.5, 8.5 Hz, 1 H), 7.94-8.05 (m, 1 H), 8.11 (ddd, J=10.9, 7.7, 2.0 Hz, 1 H), 8.12 (none, 1H), 9.51 (s, 1 H), 9.54 (s, 2 H) ppm; MS (DCI/NH$_3$) m/z 261 (M+H)$^+$.

EXAMPLE 103

3-(Pyrimidin-5-yl)-5-(2,3,4-trifluorophenyl)-1,2,4-oxadiazole

The titled compound was prepared according to the procedure of Method D using the product of Example 79C and 2,3,4-trifluorobenzoyl chloride (Aldrich). $^1$H NMR (300 MHz, DMSO-d$_6$) δ 7.58-7.75 (m, 1 H), 8.03-8.26 (m, 1 H), 9.44 (s, 2 H), 9.45 (s, 1 H) ppm; MS (DCI/NH$_3$) m/z 279 (M+H)$^+$, 296 (M+NH$_4$)$^+$.

EXAMPLE 104

3-(pyrimidin-5-yl)-5-(2,36-trifluorophenyl)-1,2,4-oxadiazole

The titled compound was prepared according to the procedure of Method D using the product of Example 79C and 2,3,6-trifluorobenzoyl chloride (Aldrich). $^1$H NMR (300 MHz, DMSO-d$_6$) δ 7.48-7.61 (m, 1 H), 7.89-8.07 (m, 1 H), 9.44 (s, 2 H), 9.45 (s, 1 H) ppm; MS (DCI/NH$_3$) m/z 279 (M+H)$^+$, 296 (M+NH$_4$)$^+$.

EXAMPLE 105

3-(pyrimidin-5-yl)-5-(2,3,4,5-tetrafluorophenyl)-1,2,4-oxadiazole

The titled compound was prepared according to the procedure of Method D using the product of Example 79C and 2,3,4,5-tetrafluorobenzoyl chloride (Aldrich). $^1$H NMR (300 MHz, DMSO-d$_6$) δ 8.18-8.42 (m, 1 H), 9.45 (s, 2 H), 9.46 (s, 1 H) ppm; MS (DCI/NH$_3$) m/z 297 (M+H)$^+$, 314 (M+NH$_4$)$^+$.

EXAMPLE 106

5-(imidazo[1,5-a]pyridin-6-yl)-3-(pyridin-3-yl)-1,2,4-oxadiazole

The title compound was prepared according to Method C using imidazo[1,2-a]pyridine-6-carboxylic acid (Maybridge) and N'-hydroxynicotinimidamide (Tyger). $^1$H NMR (300 MHz, DMSO-d$_6$) δ 7.67 (ddd, J=8.1, 4.8, 1.0 Hz, 1 H), 7.76 (d, J=1.4 Hz, 1 H), 7.78-7.92 (m, 2 H), 8.21 (s, 1 H), 8.46 (dt, J=8.2, 1.8 Hz, 1 H), 8.83 (dd, J=4.7, 1.7 Hz, 1 H), 9.27 (dd, J=2.2, 0.8 Hz, 1 H), 9.69 (dd, J=1.7, 1.0 Hz, 1 H) ppm; MS (DCI/NH$_3$) m/z 264 (M+H)$^+$.

EXAMPLE 107

5-(1H-indol-6-yl)-3-(pyridin-3-yl)-1,2,4-oxadiazole

The title compound was prepared according to Method C using 1H-indole-6-carboxylic acid (Aldrich) and N'-hydroxynicotinimidamide (Tyger). $^1$H NMR (300 MHz, DMSO-d$_6$) δ 6.62 (ddd, J=3.0, 1.9, 0.8 Hz, 1 H), 7.62-7.71 (m, 2 H), 7.76-7.89 (m, 2 H), 8.27-8.33 (m, J=1.4 Hz, 1 H), 8.46 (dt, J=8.2, 1.9, 1.7 Hz, 1 H), 8.82 (dd, J=4.7, 1.7 Hz, 1 H), 9.27 (dd, J=2.2, 0.8 Hz, 1 H), 11.66 (s, 1 H) ppm; MS (DCI/NH$_3$) m/z 263 (M+H)$^+$.

EXAMPLE 108

5-(2,7-dimethylpyrazolo[1,5-a]pyrimidin-6-yl)-3-(pyridin-3-yl)-1,2,4-oxadiazole

The title compound was prepared according Method C using 2,7-dimethylpyrazolo[1,5-a]pyrimidine-6-carboxylic acid (Maybridge) and N'-hydroxynicotinimidamide (Tyger). $^1$H NMR (300 MHz, DMSO-d$_6$) δ2.52 (s, 3 H), 3.27 (s, 3 H), 6.77 (s, 1 H), 7.67 (ddd, J=8.0, 4.9, 0.7 Hz, 1 H), 8.48 (dt, J=8.6, 1.9 Hz, 1 H), 8.84 (dd, J=4.7, 1.7 Hz, 1 H), 9.06 (s, 1 H), 9.30 (dd, J=2.2, 0.8 Hz, 1 H), 9.30 (d, J=1.4 Hz, 1 H) ppm; MS (DCI/NH$_3$) m/z 293 (M+H)$^+$.

EXAMPLE 109

5-(2,2-difluorobenzo[d][1,3]dioxol-5-yl)-3-(pyridin-3-yl)-1,2,4-oxadiazole

The title compound was prepared according to Method C using 2,2-difluorobenzo[d][1,3]dioxole-5-carboxylic acid (Aldrich) and N'-hydroxynicotinimidamide (Tyger). $^1$H NMR (300 MHz, DMSO-d$_6$) δ 7.66 (ddd, J=8.1, 4.8, 1.0 Hz, 1 H), 7.73 (d, J=8.5 Hz, 1 H), 8.14 (dd, J=8.5, 1.7 Hz, 1 H), 8.25 (d, J=1.7 Hz, 1 H), 8.44 (dt, J=8.2, 1.9, 1.7 Hz, 1 H), 8.82 (dd, J=4.7, 1.7 Hz, 1 H), 9.25 (dd, J=2.2, 0.8 Hz, 1 H) ppm; MS (DCI/NH$_3$) m/z 304 (M+H)$^+$.

EXAMPLE 110

5-(2-methylbenzofuran-5-yl)-3-(pyridin-3-yl)-1,2,4-oxadiazole

The title compound was prepared according to Method C using 2-methylbenzofuran-5-carboxylic acid (Chembridge) and N'-hydroxynicotinimidamide (Tyger). $^1$H NMR (300 MHz, DMSO-d$_6$) δ 3.33 (s, 3 H), 6.58-6.97 (m, 1 H), 7.66 (ddd, J=8.0, 4.9, 1.0 Hz, 1 H), 7.78 (d, J=8.5 Hz, 1 H), 8.40-8.55 (m, 2 H), 8.82 (dd, J=4.7, 1.7 Hz, 1 H), 9.27 (dd, J=2.2, 0.8 Hz, 1 H) ppm; MS (DCI/NH$_3$) m/z 278 (M+H)$^+$.

EXAMPLE 111

5-(benzo[d][1,2,3]thiadiazol-5-yl)-3-(pyridin-3-yl)-1,2,4-oxadiazole

The title compound was prepared according to Method C using benzo[d][1,2,3]thiadiazole-5-carboxylic acid (Maybridge) and N'-hydroxynicotinimidamide (Tyger). $^1$H NMR (300 MHz, DMSO-d$_6$) δ 7.69 (ddd, J=8.0, 4.9, 0.7 Hz, 1 H), 8.51 (dt, J=8.2, 1.9, 1.7 Hz, 1 H), 8.57 (dd, J=8.5, 1.7 Hz, 1 H), 8.73 (d, J=7.8 Hz, 1 H), 8.85 (dd, J=4.9, 1.5 Hz, 1 H), 9.32 (dd, J=2.4, 1.0 Hz, 1 H), 9.51 (dd, J=1.7, 0.7 Hz, 1 H) ppm; MS (DCI/NH$_3$) m/z 282 (M+H)$^+$.

EXAMPLE 112

5-(1H-benzo[d]imidazol-5-yl)-3-(pyridin-3-yl)-1,2,4-oxadiazole

The title compound was prepared according to Method C using 1H-benzo[d]imidazole-5-carboxylic acid (Aldrich) and N'-hydroxynicotinimidamide (Tyger). $^1$H NMR (300

MHz, DMSO-d$_6$) δ 7.66 (ddd, J=8.1, 4.8, 1.0 Hz, 1 H), 7.75-7.98 (m, 1 H), 7.99-8.17 (m, 1 H), 8.34-8.56 (m, 3 H), 8.82 (dd, J=5.1, 1.7 Hz, 1 H), 9.28 (dd, J=2.2, 0.8 Hz, 1H) ppm; MS (DCI/NH$_3$) m/z 264 (M+H)$^+$.

EXAMPLE 113

5-(1H-benzo[d][1,2,3]triazol-5-yl)-3-(pyridin-3-yl)-1,2,4-oxadiazole

The title compound was prepared according to Method C using 1H-benzo[d][1,2,3]triazole-5-carboxylic acid (Aldrich) and N'-hydroxynicotinimidamide (Tyger). $^1$H NMR (300 MHz, DMSO-d$_6$) δ 7.67 (ddd, J=8.0, 4.9, 0.7 Hz, 1 H), 8.10-8.20 (m, 1 H), 8.22-8.31 (m, 1 H), 8.49 (dt, J=8.1, 2.0, 1.7 Hz, 1 H), 8.75-8.92 (m, 2 H), 9.30 (dd, J=2.2, 0.8 Hz, 1 H) ppm; MS (DCI/NH$_3$) m/z 265 (M+H)$^+$.

EXAMPLE 114

5-(benzo[d]thiazol-5-yl)-3-(pyridin-3-yl)-1,2,4-oxadiazole

The title compound was prepared according to Method C using benzo[d]thiazole-5-carboxylic acid (Apollo) and N'-hydroxynicotinimidamide (Tyger). $^1$H NMR (300 MHz, DMSO-d$_6$) δ 7.64-7.73 (m, 1 H), 8.35 (s, 1 H), 8.36 (s, 1 H), 8.48 (dt, J=8.1, 2.0, 1.7 Hz, 1 H), 8.83 (dd, J=4.7, 1.7 Hz, 1 H), 9.17 (t, J=1.2 Hz, 1 H), 9.29 (dd, J=2.2, 0.8 Hz, 1 H), 9.66 (s, 1 H) ppm; MS (DCI/NH$_3$) m/z 281 (M+H)$^+$.

EXAMPLE 115

3-(pyridin-3-yl)-5-(1H-pyrrolo[2,3-b]pyridin-5-yl)-1,2,4-oxadiazole

The title compound was prepared according to Method C using 1H-pyrrolo[2,3-b]pyridine-5-carboxylic acid (Adesis) and N'-hydroxynicotinimidamide (Tyger). $^1$H NMR (300 MHz, DMSO-d$_6$) δ 6.71 (d, J=3.4 Hz, 1 H), 7.66 (ddd, J=7.9, 4.8, 0.8 Hz, 1 H), 7.70 (d, J=3.4 Hz, 1 H), 8.47 (dt, J=8.1, 1.9 Hz, 1 H), 8.78-8.86 (m, 2 H), 9.05 (d, J=2.0 Hz, 1 H), 9.28 (dd, J=2.2, 0.8 Hz, 1 H) ppm; MS (DCI/NH$_3$) m/z 264 (M+H)$^+$.

EXAMPLE 116

5-(1H-indol-5-yl)-3-(pyridin-3-yl)-1,2,4-oxadiazole

The title compound was prepared according to Method C using 1H-indole-5-carboxylic acid (Aldrich) and N'-hydroxynicotinimidamide (Tyger). $^1$H NMR (300 MHz, DMSO-d$_6$) δ 6.69 (dt, J=2.3, 1.4 Hz, 1 H), 7.55 (t, J=2.7 Hz, 1 H), 7.62-7.70 (m, 2 H), 7.94 (dd, J=8.8, 1.7 Hz, 1 H), 8.46 (dt, J=8.1, 1.9 Hz, 1 H), 8.49-8.52 (m, 1 H), 8.81 (dd, J=4.7, 1.7 Hz, 1 H), 9.27 (dd, J=2.2, 0.8 Hz, 1 H) ppm; MS (DCI/NH$_3$) m/z 263 (M+H)$^+$.

EXAMPLE 117

5-(benzofuran-5-yl)-3-(pyridin-3-yl)-1,2,4-oxadiazole

The title compound was prepared according to Method C using benzofuran-5-carboxylic acid (Aldrich) and N'-hydroxynicotinimidamide (Tyger). $^1$H NMR (300 MHz, DMSO-d$_6$) δ 7.20 (dd, J=2.0, 1.0 Hz, 1 H), 7.66 (ddd, J=7.9, 4.8, 0.8 Hz, 1 H), 7.91 (dt, J=8.6, 1.0, 0.8 Hz, 1 H), 8.14-8.24 (m, 2 H), 8.47 (dt, J=7.9, 2.0 Hz, 1 H), 8.60 (d, J=1.4 Hz, 1 H), 8.82 (dd, J=4.7, 1.7 Hz, 1 H), 9.28 (dd, J=2.2, 0.8 Hz, 1 H) ppm; MS (DCI/NH$_3$) m/z 264 (M+H)$^+$.

EXAMPLE 118

5-(1-methyl-1H-benzo[d]imidazol-5-yl)-3-(pyridin-3-yl)-1,2,4-oxadiazole

The title compound was prepared according to Method C using 1-methyl-1H-benzo[d]imidazole-5-carboxylic acid (Maybridge) and N'-hydroxynicotinimidamide (Tyger). $^1$H NMR (300 MHz, DMSO-d$_6$) δ7.65 (ddd, J=8.0, 4.9, 0.7 Hz, 1 H), 7.68-7.88 (m, J=8.8 Hz, 1 H), 7.87-8.10 (m, 2 H), 8.14-8.37 (m, 1 H), 8.46 (dt, J=8.1, 1.9 Hz, 1 H), 8.82 (dd, J=4.7, 1.7 Hz, 1 H), 9.27 (dd, J=2.0, 0.7 Hz, 1 H) ppm; MS (DCI/NH$_3$) m/z 278 (M+H)$^+$.

EXAMPLE 119

3-(imidazo[1,2-a]pyridin-6-yl)-5-(pyridin-3-yl)-1,2,4-oxadiazole

The title compound was prepared according to Method D using N'-hydroxyimidazo[1,2-a]pyridine-6-carboximidamide (Bionet) and nicotinoyl chloride, hydrochloric Acid (Aldrich). $^1$H NMR (300 MHz, DMSO-d$_6$) δ 7.62-7.91 (m, 4 H), 8.20 (s, 1 H), 8.56 (dt, J=8.1, 1.9 Hz, 1 H), 8.92 (dd, J=4.7, 1.7 Hz, 1 H) ppm; MS (DCI/NH$_3$) m/z 264 (M+H)$^+$.

EXAMPLE 120

5-(6-chloropyridin-3-yl)-3-(imidazo[1,2-a]pyridin-6-yl)-1,2,4-oxadiazole

The title compound was prepared according to Method D using N'-hydroxyimidazo[1,2-a]pyridine-6-carboximidamide (Bionet) and 6-chloronicotinoyl chloride (Aldrich). $^1$H NMR (300 MHz, DMSO-d$_6$) δ 7.70 (d, J=1.2 Hz, 1 H), 7.74-7.84 (m, 2 H), 7.87 (d, J=8.3 Hz, 1 H), 8.20 (s, 1 H), 8.59 (dd, J=8.5, 2.6 Hz, 1 H), 9.20 (dd, J=2.4, 0.8 Hz, 1 H), 9.47 (t, J=1.4 Hz, 1 H) ppm; MS (DCI/NH$_3$) m/z 298 (M+H)$^+$, 300 (M+H)$^+$.

EXAMPLE 121

5-(6-fluoropyridin-3-yl)-3-(imidazo[1,2-a]pyridin-6-yl)-1,2,4-oxadiazole

The title compound was prepared according to Method C using N'-hydroxyimidazo[1,2-a]pyridine-6-carboximidamide (Bionet) and 6-fluoronicotinic acid (Frontier). $^1$H NMR (300 MHz, DMSO-d$_6$) δ 7.55 (ddd, J=8.5, 2.7, 0.7 Hz, 1 H), 7.70 (d, J=1.4 Hz, 1 H), 7.73-7.86 (m, 2 H), 8.20 (s, 1 H), 8.75 (ddd, J=8.1, 2.5 Hz, 1 H), 9.08 (dt, J=1.7, 0.8 Hz, 1 H), 9.46 (dd, J=1.7, 1.0 Hz, 1 H) ppm; MS (DCI/NH$_3$) m/z 282 (M+H)$^+$.

EXAMPLE 122

5-(5-fluoropyridin-3-yl)-3-(imidazo[1,2-a]pyridin-6-yl)-1,2,4-oxadiazole

The title compound was prepared according to method C using N'-hydroxyimidazo[1,2-a]pyridine-6-carboximidamide (Bionet) and 5-fluoronicotinic acid (Frontier). $^1$H NMR (300 MHz, DMSO-d$_6$) δ 7.71 (d, J=1.4 Hz, 1 H), 7.74-7.88

(m, 2 H), 8.20 (s, 1 H), 8.51 (ddd, J=9.0, 2.9, 1.7 Hz, 1 H), 8.97 (d, J=3.1 Hz, 1 H), 9.24 (t, J=1.5 Hz, 1 H), 9.47 (t, J=1.4 Hz, 1 H) ppm; MS (DCI/NH$_3$) m/z 282 (M+H)$^+$.

EXAMPLE 123

5-(1H-indazol-5-yl)-3-(pyridin-3-yl)-1,2,4-oxadiazole

The title compound was prepared according to Method C using 1H-indazole-5-carboxylic acid (ABCR) and N'-hydroxynicotinimidamide (Tyger). $^1$H NMR (300 MHz, DMSO-d$_6$) δ 7.7 (dd, J=7.9, 4.8 Hz, 1 H), 7.8 (d, J=8.7 Hz, 1 H), 8.2 (dd, J=8.7, 1.6 Hz, 1 H), 8.4 (s, 1 H) 8.5 (dt, J=7.9, 1.8 Hz, 1 H), 8.7 (s, 1 H) 8.8 (dd, J=4.8, 1.6 Hz, 1 H), 9.3 (d, J=2.0 Hz, 1 H), 13.6 (s, 1 H) ppm; MS (DCI/NH$_3$) m/z 264 (M+H)$^+$.

EXAMPLE 124

5-([1,2,4]triazolo[4,3-a]pyridin-6-yl)-3-(pyridin-3-yl)-1,2,4-oxadiazole

EXAMPLE 124A 5-(6-Chloropyridin-3-yl)-3-(pyridin-3-yl)-1,2,4-oxadiazole

The title compound was prepared according to Method D using N'-hydroxynicotinimidamide (Tyger) and 6-chloronicotinoyl chloride (Aldrich). $^1$H NMR (300 MHz, CDCl$_3$) δ 7.48 (dd, J=7.6, 5.3 Hz, 1 H), 7.57 (d, J=8.5 Hz, 1 H), 8.40-8.48 (m, 2 H), 8.80 (dd, J=4.7, 1.7 Hz, 1 H), 9.24 (d, J=2.4 Hz, 1 H), 9.40 (d, J=2.4 Hz, 1 H) ppm; MS (DCI/NH$_3$) m/z 259 (M+H)$^+$, 261 (M+H)$^+$.

EXAMPLE 124B 5-(6-Hydrazinylpyridin-3-yl)-3-(pyridin-3-yl)-1,2,4-oxadiazole

A suspension of the product of Example 126A (260 mg, 1 mmol) in EtOH (15 mL) was stirred with hydrazine (Aldrich, 50 mg, 2.5 mmol) at refluxing temperature for 2 h and then cooled to room temperature. The precipitates were collected by filtration, washed with addition cooled EtOH (5 mL) and dried to gave the title compound. $^1$NMR (DMSO-d$_6$): δ 6.77-7.08 (m, 1 H), 7.35-7.44 (m, 2 H), 7.63 (ddd, J=8.0, 4.9, 1.0 Hz, 1 H), 7.79 (tt, J=7.6, 1.9 Hz, 1 H), 8.12 (dd, J=8.8, 2.4 Hz, 1 H), 8.41 (dt, J=8.1, 1.9 Hz, 1 H), 8.58 (dt, J=4.0, 1.9 Hz, 1 H), 8.75-8.84 (m, 1 H), 9.22 (dd, J=2.2, 0.8 Hz, 1 H) ppm, MS (DCI/NH$_3$) m/z=255 (M+H)$^+$.

EXAMPLE 124C 5-([1,2,4]triazolo[4,3-a]pyridin-6-yl)-3-(pyridin-3-yl)-1,2,4-oxadiazole A suspension of the product of Example 126B (80 mg, 0.31 mmol) in triethoxymethane (Aldrich, 4 mL) was heated to reflux for 16 hours. The reaction mixture was cooled to room temperature and the volatiles were removed under vacuum. The residue was purified with chromatography (SiO$_2$, EtOAc/CH$_2$Cl$_2$=1/9) to give the title compound. $^1$H NMR (DMSO-d$_6$): δ 7.68 (dd, J=8.1, 5.0 Hz, 1 H), 7.90-8.11 (m, 2 H), 8.46 (dt, J=7.9, 2.0 Hz, 1 H), 8.84 (dd, J=4.8, 1.6 Hz, 1 H), 9.27 (d, J=2.0 Hz, 1 H), 9.44 (s, 1 H), 9.68 (s, 1 H) ppm; MS (DCI/NH$_3$) m/z=265 (M+H)$^+$.

EXAMPLE 125

5-(3-(pyridin-3-yl)-1,2,4-oxadiazol-5-yl)benzo[d]oxazol-2(3H)-one

The title compound was prepared according to Method C using 2-oxo-2,3-dihydrobenzo[d]oxazole-5-carboxylic acid (Matrix) and N'-hydroxynicotinimidamide (Tyger). $^1$H NMR (300 MHz, CD$_3$OD) δ 7.40 (d, J=8.5 Hz, 1 H), 7.64 (ddd, J=8.0, 5.0, 0.9 Hz, 1 H), 7.90 (d, J=1.7 Hz, 1 H), 8.01 (dd, J=8.3, 1.9 Hz, 1 H), 8.55 (dt, J=7.8, 1.9 Hz, 1 H), 8.74 (dd, J=4.8, 1.7 Hz, 1 H), 9.29 (dd, J=2.2, 0.9 Hz, 1 H). ppm; MS (DCI/NH$_3$) m/z 281 (M+H)$^+$.

EXAMPLE 126

5-(3-(pyridin-3-yl)-1,2,4-oxadiazol-5-yl)-1H-benzo[d]imidazole-2(3H)-thione

The title compound was prepared according to Method C using 2-mercapto-5-benzimidazolecarboxylic acid (Princeton) and N'-hydroxynicotinimidamide (Tyger). $^1$H NMR (300 MHz, CD$_3$OD) δ 7.38 (d, J=8.5 Hz, 1 H), 7.65 (ddd, J=8.0, 4.9, 0.7 Hz, 1 H), 7.86 (d, J=1.0 Hz, 1 H), 8.00 (dd, J=8.1, 1.7 Hz, 1 H), 8.45 (dt, J=8.0, 1.9 Hz, 1 H), 8.81 (dd, J=4.9, 1.5 Hz, 1 H), 9.26 (dd, J=2.2, 0.9 Hz, 1 H) ppm; MS (DCI/NH$_3$) m/z 296 (M+H)$^+$.

EXAMPLE 127

1,3-dimethyl-5-(3-(pyridin-3-yl)-1,2,4-oxadiazol-5-yl)-1H-benzo[d]imidazol-2(3H)-one The title compound was prepared according to Method C using 1,3-dimethyl-2-oxo-2,3-dihydro-1H-benzoimidazole-5-carboxylic acid (Matrix) and N'-hydroxynicotinimidamide (Tyger). $^1$H NMR (300 MHz, CD$_3$OD) δ 3.49 (s, 3 H), 3.53 (s, 3H), 7.36 (d, J=8.3 Hz, 1 H), 7.64 (ddd, J=8.0, 5.1, 0.8 Hz, 1 H), 7.98 (d, J=1.6 Hz, 1 H), 8.08 (dd, J=8.3, 1.6 Hz, 1 H), 8.55 (dt, J=8.0, 1.9 Hz, 1 H), 8.73 (dd, J=4.8, 1.6 Hz, 1 H) 9.29 (d, J=1.2 Hz, 1 H). MS (DCI/NH$_3$) m/z 308 (M+H)$^+$.

EXAMPLE 128

6-(3-(pyridin-3-yl)-1,2,4-oxadiazol-5-yl)benzo[d]oxazol-2(3H)-one

The title compound was prepared according to Method C using 2-oxo-2,3-dihydrobenzo[d]oxazole-6-carboxylic acid (Eur. J. Med. Chem. 1974, 9, 491-6.) and N'-hydroxynicotinimidamide (Tyger). $^1$H NMR (300 MHz, DMSO-d$_6$) δ 7.35 (d, J=8.7 Hz, 1 H), 7.65 (dd, J=7.5, 4.4 Hz, 1 H), 8.04 (d, J=1.6 Hz, 1 H), 8.07 (s, 1 H), 8.44 (dt, J=7.9, 2.0 Hz, 1 H), 8.82 (dd, J=4.8, 1.6 Hz, 1 H), 9.25 (d, J=1.6 Hz, 1 H) ppm; MS (DCI/NH$_3$) m/z 281 (M+H)$^+$.

EXAMPLE 129

5-(3-(pyridin-3-yl)-1,2,4-oxadiazol-5-yl)-1H-benzo[d]imidazol-2(3H)-one trifluoroacetic Acid A solution of 2-oxo-2,3-dihydro-1H-benzo[d]imidazole-5-carboxylic acid (Princeton, 178 mg, 1.0 mmol) in CH$_2$Cl$_2$ (anhydrous, 5.0 mL) was stirred with oxalyl chloride (Aldrich, 2 M, in CH$_2$Cl$_2$, 1.0 mL) in the presence of 2 drops dimethylformamide at room temperature for 1 hour. It was then concentrated and dried under reduced pressure. The residue was dissolved in pyridine (5.00 mL) and then stirred with N'-hydroxynicotinimidamide (Tyger, 137 mg, 1.0 mmol) at 100° C. for 16 hours. The reaction mixture was cooled to ambient temperature, diluted with EtOAc (50 mL), washed with water (2×10 mL) and brine. The organic solution was concentrated under reduced pressure, purified with preparative HPLC [Waters, column: Xbridge™ Prep C18 5 µm, OBD™ 30×100 mm, solvent: acetonitrile/water (v. 1% TFA), 5/95 to 95/5, flow rate of 40 mL/minute. Fractions were collected based upon UV signal threshold.] the title compound. $^1$H NMR (300 MHz, CD$_3$OD) δ 7.25 (d, J=8.3 Hz, 1 H), 7.75 (ddd, J=7.9, 5.2, 0.8 Hz, 1 H), 7.88 (d, J=1.6 Hz, 1 H), 7.99 (dd, J=8.3, 1.6 Hz, 1 H), 8.68 (dt, J=7.9, 1.8 Hz, 1 H), 8.79 (dd, J=5.2, 1.6 Hz, 1 H), 9.33 (d, J=1.2 Hz, 1 H) ppm. MS (DCI/NH$_3$) m/z 280 (M+H)$^+$.

EXAMPLE 130

6-(3-(Pyridin-3-yl)-1,2,4-oxadiazol-5-yl)benzo[d]oxazol-2-amine

EXAMPLE 130A 2-nitro-5-(3-(pyridin-3-yl)-1,2,4-oxadiazol-5-yl)phenol

The title compound was prepared according to Method C using 3-hydroxy-4-nitrobenzoic acid (Aldrich) and N'-hydroxynicotinimidamide (Tyger). $^1$H NMR (300 MHz, DMSO-d$_6$) δ 7.67 (ddd, J=7.9, 4.8, 0.8 Hz, 1 H), 7.76 (dd, J=8.5, 1.8 Hz, 1 H), 7.92 (d, J=1.6 Hz, 1 H), 8.12 (d, J=8.3 Hz, 1 H), 8.45 (dt, J=7.9, 2.0 Hz, 1 H), 8.83 (dd, J=4.8, 1.6 Hz, 1 H), 9.26 (d, J=1.2 Hz, 1 H)) ppm; MS (DCI/NH$_3$) m/z 285 (M+H)$^+$.

EXAMPLE 130B 2-amino-5-(3-(pyridin-3-yl)-1,2,4-oxadiazol-5-yl)phenol

A solution of the product of Example 132A (1.0 g, 3.52 mmol) in THF (20.0 mL) was stirred with Raney nickel (Aldrich, 4.0 g) under H$_2$ (30 psi) for 2 hours. The catalyst was then carefully removed by filtration and the reaction mixture was concentrated to give the title compound. $^1$H NMR (300 MHz, DMSO-d$_6$) δ 5.67 (s, 2 H), 6.74 (d, J=8.1 Hz, 1 H), 7.40-7.52 (m, 2 H), 7.62 (dd, J=8.0, 4.2 Hz, 1 H), 8.39 (dt, J=8.0, 2.0, 1.9 Hz, 1 H), 8.78 (dd, J=4.7, 1.7 Hz, 1 H), 9.20 (d, J=1.7 Hz, 1 H), 9.65-9.98 (m, J=3.4 Hz, 1 H) ppm; MS (DCI/NH$_3$) m/z 255 (M+H)$^+$.

EXAMPLE 130C 6-(3-(Pyridin-3-yl)-1,2,4-oxadiazol-5-yl)benzo[d]oxazol-2-amine To a solution of the product of Example 132B (254 mg, 1.0 mmol) in THF (20 ml) was added cyanic bromide (Aldrich, 106 mg, 1.0 mmol) and triethylamine (Aldrich, 0.14 ml, 1.0 mmol). The mixture was then stirred at 50° C. for 10 h, cooled to ambient temperature, triturated with water (40 mL). The precipitate was filtered and dried under vacuum to give the titled compound. $^1$H NMR (300 MHz, DMSO-d$_6$) δ 7.42 (d, J=8.1 Hz, 1 H), 7.65 (dd, J=7.8, 5.1 Hz, 1 H), 7.98 (s, 2 H), 8.02 (dd, J=8.1, 1.7 Hz, 1 H), 8.12 (d, J=1.7 Hz, 1 H), 8.44 (dt, J=8.1, 1.9 Hz, 1 H), 8.81 (dd, J=4.7, 1.7 Hz, 1 H), 9.26 (d, J=1.4 Hz, 1 H) ppm; MS (DCI/NH$_3$) m/z 280 (M+H)$^+$.

EXAMPLE 131

6-(3-(pyridin-3-yl)-1,2,4-oxadiazol-5-yl)benzo[d]oxazole

To a solution of the product of Example 132B (508 mg, 2.0 mmol) in triethyl orthoformate (Aldrich, 20 mL, 120 mmol) was stirred at 100° C. for 10 hours. It was then cooled to ambient temperature, and then triturated with hexanes (50 mL). The precipitate was filtered and dried under vacuum to give the titled compound. $^1$H NMR (300 MHz, DMSO-d$_6$) δ 7.67 (ddd, J=7.9, 4.8, 0.8 Hz, 1 H), 8.10 (d, J=8.3 Hz, 1 H), 8.28 (dd, J=8.3, 1.6 Hz, 1 H), 8.48 (dt, J=7.9, 2.0 Hz, 1 H), 8.66 (d, J=1.6 Hz, 1 H), 8.83 (dd, J=4.8, 1.6 Hz, 1 H), 9.04 (s, 1 H), 9.29 (d, J=2.4 Hz, 1 H) ppm; MS (DCI/NH$_3$) m/z 265 (M+H)$^+$.

EXAMPLE 132

5-(5-(pyridin-3-yl)-1,2,4-oxadiazol-3-yl)benzo[d]oxazol-2(3H)-one

EXAMPLE 132A 2-oxo-2,3-dihydrobenzo[d]oxazole-5-carbonitrile

A solution of 3-Amino-4-hydroxybenzonitrile (Betapharma, 537 mg, 4 mmol) in CH$_2$Cl$_2$ (20 ml) was stirred with N,N'-carbonyldiimidazole (Aldrich, 713 mg, 4.40 mmol) at room temperature for 16 hours. It was then concentrated under reduced pressure. The residue was stirred with water (10 mL) for 5 minutes, and extracted with EtOAc (3×10 mL). The combined extracts were concentrated to the title compound. $^1$H NMR (300 MHz, CD$_3$OD) δ 7.17-7.22 (m, 1 H), 7.28-7.34 (m, 2 H) ppm; MS (DCI/NH$_3$) m/z 178 (M+NH$_4$)$^+$.

EXAMPLE 132B

N'-Hydroxy-2-oxo-2,3-dihydrobenzo[d]oxazole-5-carboximidamide

A solution of the product from Example 134A (300 mg, 1.9 mmol), hydroxylammonium chloride (Aldrich, 64.0 mg, 1.9 mmol) and triethylamine (Aldrich, 227 mg, 2.3 mmol), in methanol (10 mL) was stirred at 65° C. for 2 h, cooled to ambient temperature, then concentrated under reduced pressure. The residue was triturated with EtOAc (10 mL). The precipitate was filtered and dried under vacuum to give the titled compound. $^1$H NMR (300 MHz, CD$_3$OD) δ 7.22 (d, J=8.33 Hz, 1 H) 7.34-7.43 (m, 2 H). MS (DCI/NH$_3$) m/z 194 (M+H)$^+$.

EXAMPLE 132C 5-(5-(pyridin-3-yl)-1,2,4-oxadiazol-3-yl)benzo[d]oxazol-2(3H)-one The title compound was prepared according to Method D using the product of Example 134B and nicotinoyl chloride (Aldrich). $^1$H NMR (300 MHz, CD$_3$OD) δ 7.51 (d, J=8.7 Hz, 1 H), 7.68-7.75 (m, 2 H), 7.87 (dd, J=8.3, 2.0 Hz, 1 H), 8.57

(dt, J=7.9, 2.0 Hz, 1 H), 8.90 (dd, J=5.0, 1.8 Hz, 1 H), 9.36 (d, J=1.6 Hz, 1 H) ppm. MS (DCI/NH$_3$) m/z 281 (M+H)$^+$.

EXAMPLE 133

5-(5-(6-chloropyridin-3-yl)-1,2,4-oxadiazol-3-yl) benzo[d]oxazol-2(3H)-one

The title compound was prepared according to Method D using the product of Example 134B and 6-chloronicotinoyl chloride (Aldrich). $^1$H NMR (300 MHz, CD$_3$OD) δ 7.33 (d, J=8.3 Hz, 1 H), 7.73 (dd, J=8.3, 0.8 Hz, 1 H), 7.82 (d, J=1.6 Hz, 1 H), 7.91 (dd, J=8.3, 1.6 Hz, 1 H), 8.57 (dd, J=8.3, 2.4 Hz, 1 H), 9.19 (d, J=2.4 Hz, 1 H) ppm. MS (DCI/NH$_3$) m/z 315 317 (M+H)$^+$.

EXAMPLE 134

5-(benzo[d][1,3]dioxol-5-yl)-3-(pyridin-3-yl)-1,2,4-oxadiazole

The title compound was prepared according to method C using benzo[d][1,3]dioxole-5-carboxylic acid (Aldrich) and N'-hydroxynicotinimidamide (Tyger). $^1$H NMR (300 MHz, DMSO-d$_6$) δ 6.22 (s, 2 H), 7.20 (d, J=8.1 Hz, 1 H), 7.61-7.69 (m, 2 H), 7.81 (dd, J=8.1, 1.7 Hz, 1 H), 8.42 (dt, J=8.2, 1.9, 1.7 Hz, 1 H), 8.81 (dd, J=4.7, 1.7 Hz, 1 H), 9.24 (dd, J=2.2, 0.8 Hz, 1 H) ppm; MS (DCI/NH$_3$) m/z 268 (M+H)$^+$.

In addition to the specific compounds, one of ordinary skill in the art would readily recognize that a variety of pharmaceutically acceptable salts, esters, amides, and prodrugs of a parent compound also could be incorporated into a composition, method, or article of manufacture of the present invention.

Suitable pharmaceutically acceptable basic addition salts include, but are not limited to cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Other possible compounds include pharmaceutically acceptable amides and esters. For a description of pharmaceutically acceptable esters as prodrugs, see Bundgaard, E., ed., (1985) Design of Prodrugs, Elsevier Science Publishers, Amsterdam, which is hereby incorporated by reference. These esters are typically formed from the corresponding carboxylic acid and an alcohol. Generally, ester formation can be accomplished via conventional synthetic techniques. (See, e.g., March Advanced Organic Chemistry, 3rd Ed., John Wiley & Sons, New York p. 1157 (1985) and references cited therein, and Mark et al. Encyclopedia of Chemical Technology, John Wiley & Sons, New York (1980), both of which are hereby incorporated by reference. The alcohol component of the ester will generally comprise (i) a C2-C12 aliphatic alcohol that can or can not contain one or more double bonds and can or can not contain branched carbons or (ii) a C7-C12 aromatic or heteroaromatic alcohols. This invention also contemplates the use of those compositions, which are both esters as described herein, and at the same time are the pharmaceutically acceptable salts thereof.

For a description of pharmaceutically acceptable amides as prodrugs, see Bundgaard, H., Ed., (1985) Design of Prodrugs, Elsevier Science Publishers, Amsterdam. These amides are typically formed from the corresponding carboxylic acid and an amine. Generally, amide formation can be accomplished via conventional synthetic techniques. (See, e.g., Advanced Organic Chemistry, 3rd Ed., John Wiley & Sons, New York, p. 1152 (1985) and Mark et al. Encyclopedia of Chemical Technology, John Wiley & Sons, New York (1980), both of which are hereby incorporated by reference. This invention also contemplates the use of those compositions, which are amides, as described herein, and at the same time are the pharmaceutically acceptable salts thereof.

It also will be readily apparent to one with skill in the art that the compounds can be generated in vivo by administration of a drug precursor which, following administration, releases the drug in vivo via a chemical or physiological process (e.g., a parent compound on being brought to the physiological pH or through enzyme action is converted to the desired drug form).

Administration

As noted above, it has been discovered that pain can be treated by concurrently administering to a patient (e.g., a mammal, such as a human) in need thereof, an α4β2 PAM and an α4β2 receptor ligand. Such combination may be especially useful in expanding the dosage range for obtaining therapeutically beneficial effects.

The dosage range at which the α4β2 PAM and an α4β2 receptor ligand will be administered concurrently can vary widely. The specific dosage will be chosen by the patient's physician taking into account the particular compounds chosen, the severity of the patient's illness, any other medical conditions or diseases the patient is suffering from, other drugs the patient is taking and their potential to cause an interaction or adverse event, the patient's previous response to medication, and other factors. Suitable dosage ranges for the α4β2 PAM are from about 0.0001 mg/kg to 100 mg/kg of body weight. Suitable dosage ranges for the α4β2 receptor ligand are from about 0.0001 mg/kg to 100 mg/kg of body weight.

The α4β2 PAM and an α4β2 receptor ligand should be administered concurrently in amounts that are effective to treat the patient's pain, cognitive disorder, or related condition. In more general terms, one would create a combination of the present invention by choosing a dosage of an α4β2 PAM and an α4β2 receptor ligand according to the spirit of the guidelines presented above.

The invention also is carried out by administering an α4β2 PAM together with an α4β2 receptor ligand in any manner which provides effective levels of the compounds in the body at the same time. Typically, the combination will be administered orally.

However, the invention is not limited to oral administration. The invention should be construed to cover any route of administration that is appropriate for the medications involved and for the patient. For example, transdermal administration may be very desirable for patients who are forgetful or petulant about taking oral medicine. Injections may be appropriate for patients refusing their medication. One of the drugs may be administered by one route, such as oral, and the others may be administered by the transdermal, percutaneous, intravenous, intramuscular, intranasal, or intrarectal route, in particular circumstances. The route of administration may be varied in any way, limited by the physical properties of the drugs and the convenience of the patient and the caregiver.

Based on the diversity of the mechanisms underlying chronic pain (e.g. nociceptive or neuropathic, degrees of pain intensity, various etiologies etc), currently available pain medications are not efficacious in all patients or in all pain conditions. Analgesics can be broadly categorized as non-opioid analgesics (acetaminophen and non-steroidal anti-inflammatory drugs (NSAIDs)), opioid analgesics (morphine) and adjuvant analgesics or co-analgesics (antiepileptic drugs and antidepressants). In a simplified classification, non-opioid analgesics are mostly used to relieve mild to moderate nociceptive pain, adjuvant analgesics (gabapentin, pregabalin) are used to relieve neuropathic pain, and opioid analgesics are used to treat severe pain of all origins, depending on the dose prescribed.

Nicotinic acetylcholine receptor ligands act at multiple locations throughout the pain pathway to relieve pain. Nicotinic acetylcholine receptor ligands are found on primary sensory neurons (periphery) where nociceptive information is initiated, in the cell body regions of these neurons (i.e. the dorsal root ganglion or DRG), the dorsal spinal cord where the first pain synapse is located, in the brainstem cell body regions that control descending innervation, as well as in the higher brain regions that integrate and perceive sensory information such as the thalamus and the cortex. The current theory supported by evidence from multiple sources (reviewed in Decker et al., Curr Topics Med Chem, 4: 369, 2004) is that anti-nociceptive effects of nAChR ligands are mediated by activation of brain stem nuclei with descending inhibitory inputs to the spinal cord. Additional pathways may also mediate analgesic effects of nAChR agonists in persistent or neuropathic pain.

Another aspect of the invention is the potential to enhance efficacy of other medications used for treating pain when combined with an α4β2 PAM. As noted above, examples of currently used drugs include opioids, gabapentin, pregabalin, duloxetine and others. Novel mechanisms such as cannabinoids, vanilloid receptor antagonists, calcium channel blockers and sodium channel blockers are also being developed for the treatment of pain. For many of these mechanisms, it is emerging that a component of efficacy may be driven by activation of descending inhibitory inputs. For example, opioid analgesics can block pain transmission, in part by increasing descending inhibitory pathways to modulate pain transmission at the spinal level (Pasternack, G. W., Clin Neuropharmcol. 16: 1, 1993; Lauretti, G. T., Expert Reviews in Neurotherapeutics, 6: 613-622. 2006). Since these drugs exert their effect via activating descending inhibitory inputs, and these pathways can be shared or commonly activated by α4β2 nAChR ligands, it is anticipated that co-administration of α4β2 selective PAMs can lead to enhanced efficacy of other analgesic agents by amplifying the descending inhibitory control of spinal cord activation. Thus, combination with α4β2 PAMs enables the opportunity to create analgesic medications with either a broader or superior spectrum of efficacy that would improve the treatment of chronic pain.

Other nAChR-mediated diseases or disorders also can benefit from such concurrent administration. The combination of α4β2 nAChR ligands and α4β2 selective PAMs can be used for treatment of diseases or disorders related to the cholinergic system of the central nervous system, the peripheral nervous system, diseases or disorders related to smooth muscle contraction, endocrine diseases or disorders, diseases or disorders related to neuro-degeneration, diseases or disorders related to inflammation, and withdrawal symptoms caused by the termination of abuse of chemical substances, in for example nicotine, as well as pain. In a particular embodiment, the combination is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's Disease, dementia associated with Lewy bodies, dementia associated with Down's syndrome, schizophrenia, smoking cessation, substance abuse, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities. The method is useful for conditions and disorders related to conditions and disorders characterized by neuropyschological and cognitive dysfunction, for example in Alzheimer's disease, bipolar disorder, schizophrenia, schizoaffective disorder, and other related disorders characterized by neuropyschological and cognitive dysfunction, in particular.

For example, one embodiment relates to a method of use for treating or preventing a condition or disorder characterized by attention or cognitive dysfunction, such as Alzhimer's disease and ADHD, among other condition and disorders. The method comprises the step of administering a therapeutically effective amount of a nicotinic acetylcholine receptor subtype α4β2 positive allosteric modulator to a subject in need thereof in combination with a drug that improves cholinergic function. Examples of such drugs are nicotinic acetylcholine receptor ligands and acetylcholinesterase inhibitors.

Another method of use relates to treating or preventing a condition or disorder characterized by neuropyschological dysfunction, for example schizophrenia, wherein the method comprises the step of administering a therapeutically effective amount of a nicotinic acetylcholine receptor subtype α4β2 positive allosteric modulator to a subject in need thereof in combination with an antipsychotic agent.

Biological Activity

EXAMPLE A

α4β2 Positive Allosteric Modulator Enhances the Effects of Nicotinic Agonists

Calcium Flux Assays Using Cells Expressing nAChR Subtypes

Experimental Procedure: Human embryonic kidney (HEK) 293 cells stably expressing human α4β2 or α3β4 combinations are grown to confluency in 162 cm² tissue culture flasks in DMEM media supplemented with 10% FBS and 25 µg/ml zeocin and 200 µg/ml hygromycin B. IMR-32 neuroblastoma cells (ATCC) are grown to confluency in 162 cm² tissue culture flasks in minimum essential media supplemented with 10% FBS and 1 mM sodium pyruvate, 1% non-essential amino acids and 1% antibiotic-antimycotic. The cells are then dissociated using cell dissociation buffer and 100-150 µl per well of 3.5×10⁵ cells/ml cell suspension (~50,000-100,000 cells/well) was plated into 96-well black plates (poly-D-lysine precoated) with clear bottom and maintained for 24-48 hours in a tissue culture incubator at 37° C. under an atmosphere of 5% CO₂: 95% air. Other clonal cell lines or primary cell cultures that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM $CaCl_2$ containing 10 mM HEPES, The stock solution was diluted 1:20 using the same buffer before use. The growth media was removed from the cells. The cells were loaded with 100 μl of the dye per well and incubated at room temperature for up to one hour for HEK 293 clonal stable cell lines or 30 minutes-45 minutes at 37° C. for IMR-32 cells Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 μl and incubated for five minutes. The fluorescence intensity was captured every second for the first 1 minute followed by every 5 seconds for an additional 4 minutes. This procedure was followed by 50 μl of 4× concentration of agonist and readings were taken for a period of 3-5 minutes as described above. Data was normalized to maximal responses and plotted as a function of concentration. The concentration dependence of changes fluorescence responses was fitted by non-linear regression analysis (GraphPad Prism, San Diego, Calif.) to obtain $EC_{50}$ values.

Figure 1B:
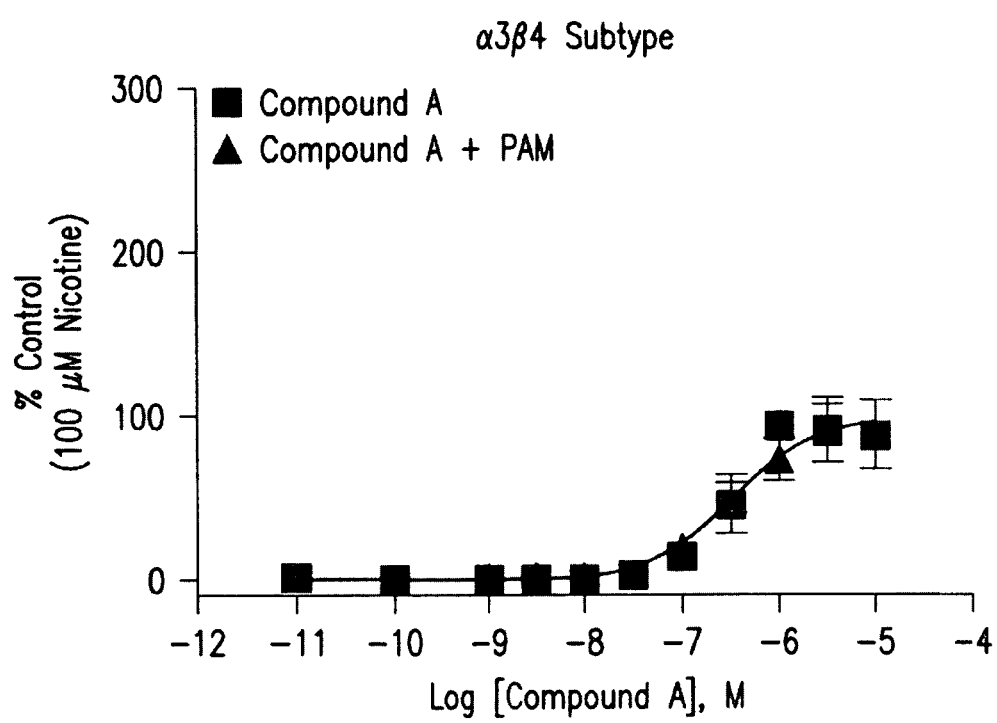
Figure 2A:
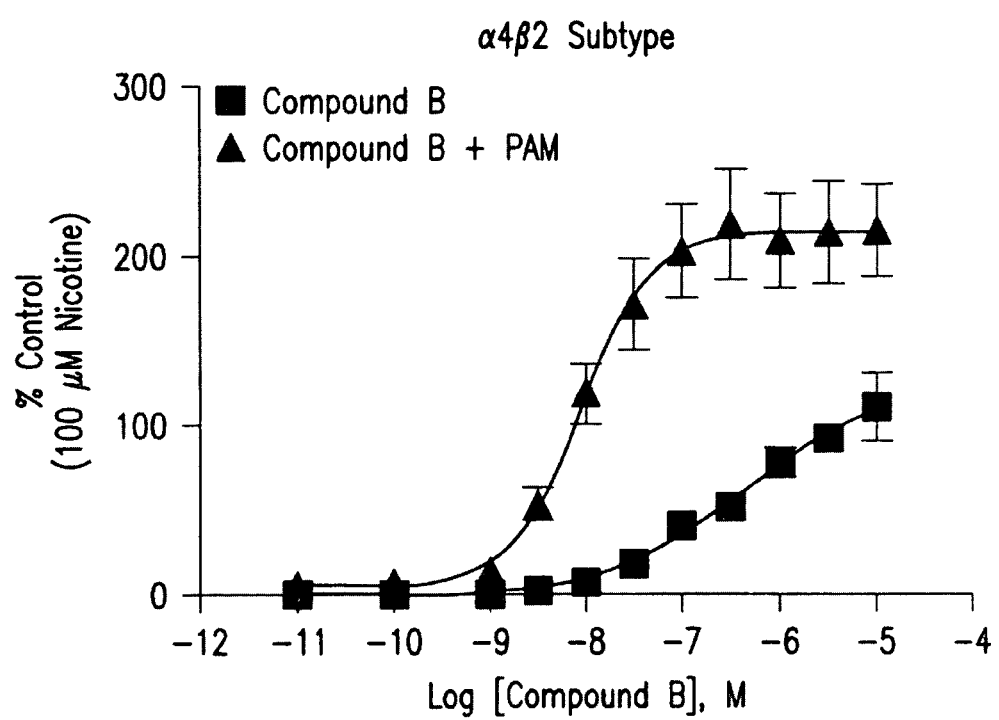
FIGS. 2A and 2B depict responses of another representative nicotinic acetylcholine receptor ligand, (3R)-1-pyridin-3-ylpyrrolidin-3-amine (Compound B), in the absence and presence of an α4β2 positive allosteric modulator, 3-(3-(pyridin-3-yl)-1,2,4-oxadiazol-5-yl)benzonitrile (PAM, Compound 1), at human α4β2 or α3β4 nicotinic receptor subtypes expressed in HEK-293 cells. Again, the data demonstrate a leftward shift in potency (EC$_{50}$ value) of the nAChR agonist at α4β2, but not α3β4 nAChRs.
Figure 2B:
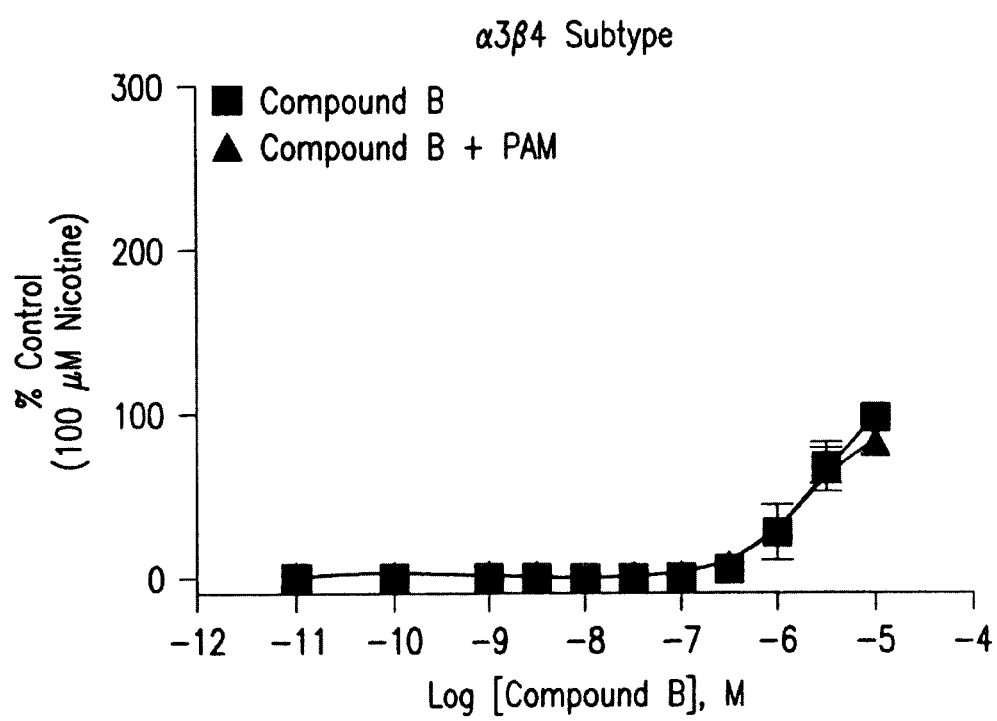

The positive allosteric modulator effects on α4β2 nAChRs exemplified by 3-(3-pyridin-3-yl-1,2,4-oxadiazol-5-yl)benzonitrile (Compound 1) and 3,5-di(pyridin-3-yl)-1,2,4-oxadiazole (Compound 2) can be identified by measuring their potentiating effect to fluorescence changes in intracellular calcium using a fluorimetric plate reader. The potentiating effect of an α4β2 modulator on α4β2 receptor can also be illustrated by concentration responses to α4β2 agonists, for example 5-[(2R)-azetidin-2-ylmethoxy]-2-chloropyridine (Compound A) and (3R)-1-pyridin-3-ylpyrrolidin-3-amine (Compound B), in presence of a fixed concentration of PAM. As shown in FIGS. 1A and 2A, in the presence of an α4β2 PAM (for example, 3-(3-(pyridin-3-yl)-1,2,4-oxadiazol-5-yl) benzonitrile (Compound 1) at 10 μM), the concentration-responses to α4β2 agonists, for example 5-[(2R)-azetidin-2-ylmethoxy]-2-chloropyridine (Compound A) and (3R)-1-pyridin-3-ylpyrrolidin-3-amine (Compound B), are shifted typically by 1-2 log units (10-100-fold) to the left resulting in more potent $EC_{50}$ values to agonists. In addition to compound A and B, other known nicotinic agonists can be left-shifted in presence of α4β2 PAM such as 3-(3-(pyridin-3-yl)-1,2,4-oxadiazol-5-yl)benzonitrile (Compound 1, FIG. 2C). When these experiments are done with cells expressing other nAChR subunits such as α3β4 (see FIGS. 1B and 2B), the PAM is unable to affect the concentration responses to the agonists. This shows that PAMs can selective enhance potency of the compound selectively at α4β2, but not other (e.g. α3β4) subtypes. This could lead to preferential effects of the agonist at the desired subtype, viz., α4β2, without effects at other nicotinic receptor subtypes and thus enhancing in vivo selectivity of the agonist.

Table 1 lists the results for the compounds of the present invention. The activity (allosteric effects—potentiation of fluorescence responses) ranges are defined as follows; "a" denotes as activity range from 200-400%, "b" denotes an activity range from 150-200%, "c" denotes an activity range from 120-150% and "d" denotes an activity range 90-120%.

TABLE 1

Examples of Selected α4β2 positive allosteric modulators

| Example No. | Structure | Activity |
|---|---|---|
| 1 | 3-pyridyl-1,2,4-oxadiazole-3-cyanophenyl | a |
| 2 | 3-pyridyl-1,2,4-oxadiazole-3-pyridyl | a |
| 3 | 3-cyanophenyl-1,2,4-oxadiazole-3-pyridyl | a |
| 4 | 3-cyanophenyl-1,2,4-oxadiazole-(6-fluoropyridin-3-yl) | b |
| 5 | 3-pyridyl-1,2,4-oxadiazole-(5-bromopyridin-3-yl) | c |
| 7 | (6-methylpyridin-3-yl)-1,2,4-oxadiazole-3-cyanophenyl | b |
| 9 | 3-pyridyl-1,2,4-oxadiazole-(5-hydroxypyridin-3-yl) | d |
| 10 | 3-pyridyl-1,2,4-oxadiazole-(3,4-difluorophenyl) | a |
| 19 | 3-pyridyl-1,2,4-oxadiazole-(4-cyanophenyl) | b |
| 35 | 3-pyridyl-1,2,4-oxadiazole-(3-sulfamoylphenyl) | a |

TABLE 1-continued

Examples of Selected α4β2 positive allosteric modulators

| Example No. | Structure | Activity |
|---|---|---|
| 40 | 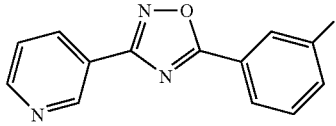 | a |
| 41 | 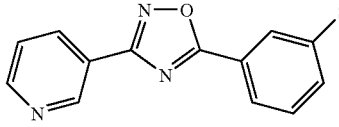 | c |
| 42 | 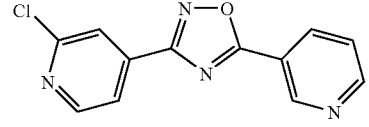 [SMILES: Clc1cc(-c2noc(-c3cccnc3)n2)ccn1] | c |
| 52 | 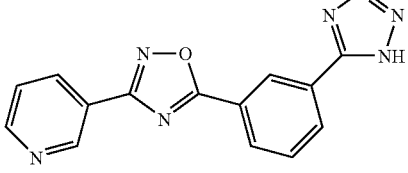 | d |
| 55 | 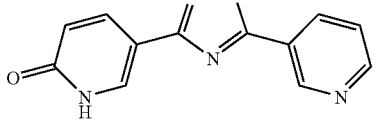 | c |
| 68 | 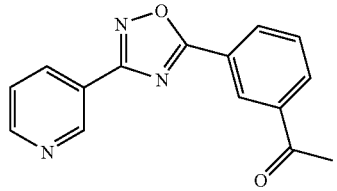 [SMILES: CC(=O)c1cccc(-c2nc(-c3cccnc3)no2)c1] | b |
| 11 | 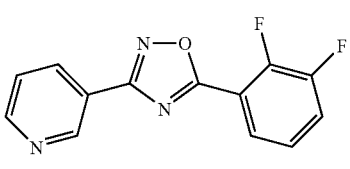 [SMILES: Fc1cccc(-c2nc(-c3cccnc3)no2)c1F] | a |
| 125 | 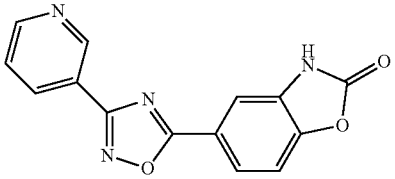 [SMILES: O=c1[nH]c2cc(-c3nc(-c4cccnc4)no3)ccc2o1] | a |
| 101 | 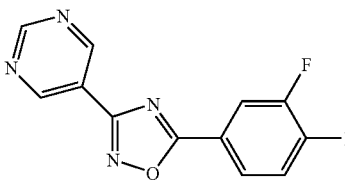 | a |
| 76 | 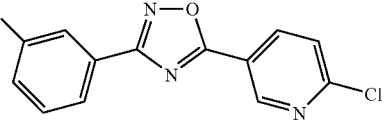 | b |
| 83 | 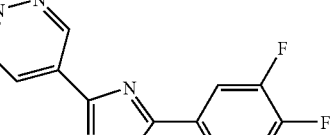 | a |
| 132 | 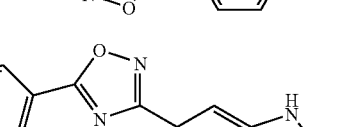 | a |

Figure 3A:
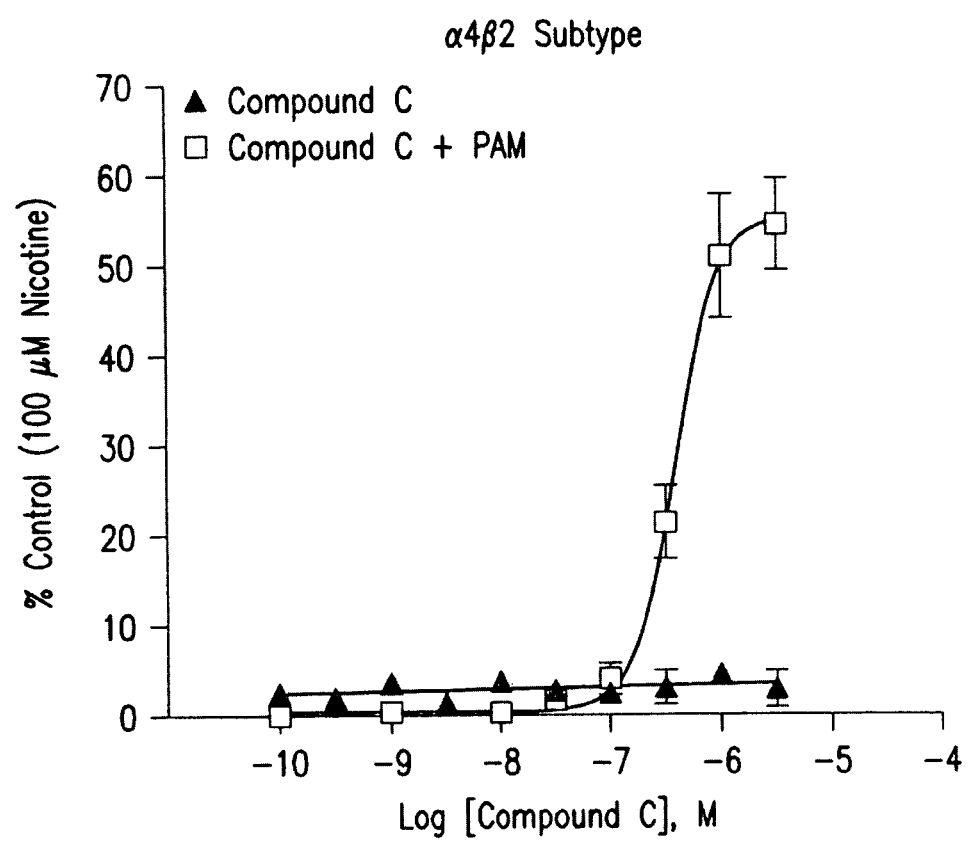
FIGS. 3A and 3B graphically represent the effect of α4β2 positive allosteric modulator in enhancing the effect of a nAChR partial agonist, such as 2-methyl-3-(2-(S)-pyrrolidinylmethoxy)pyridine (Compound C, also known as ABT-089; Reuter, L. E., et al., CNS Drug Rev., 10 (2), 167-182, 2004). Compound C alone does not evoke a calcium response, but when co-applied with the PAM, 3-(3-(pyridin-3-yl)-1,2,4-oxadiazol-5-yl)benzonitrile (Compound 1), evoked robust responses at α4β2 nAChRs (FIG. 3A), but not at α3β4 nAChRs (FIG. 3B). Compound C is a representative of other nicotinic partial agonists.
Figure 3B:
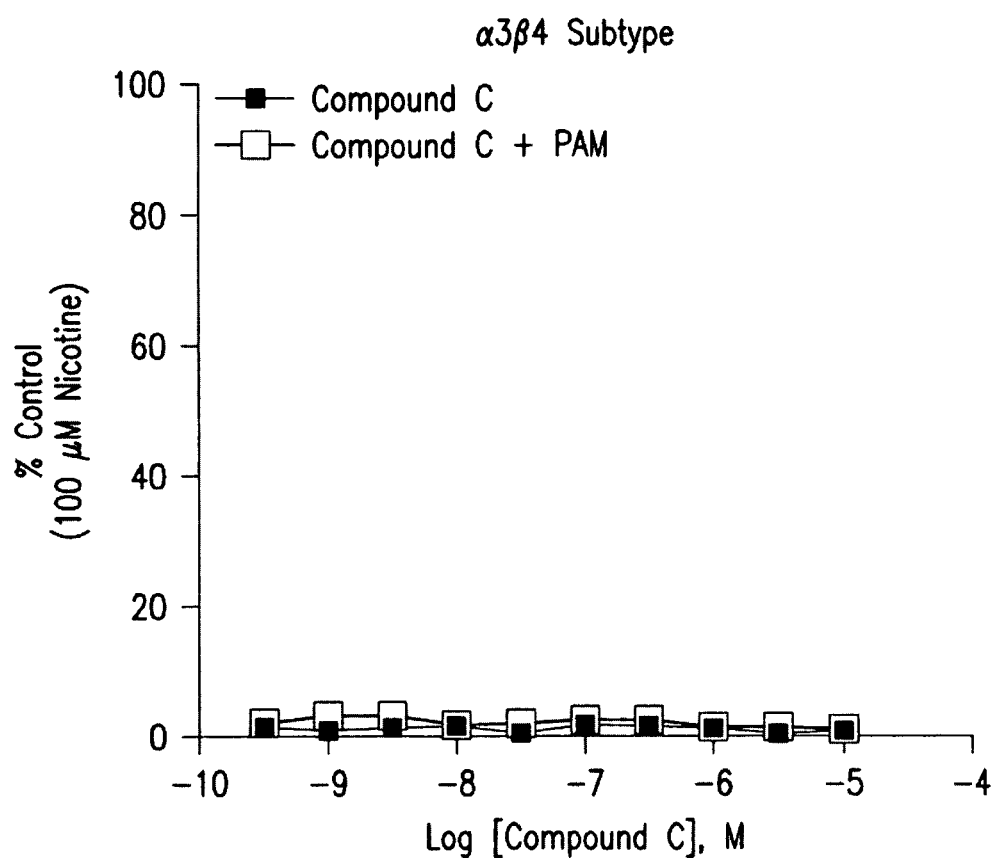
Figure 4A:
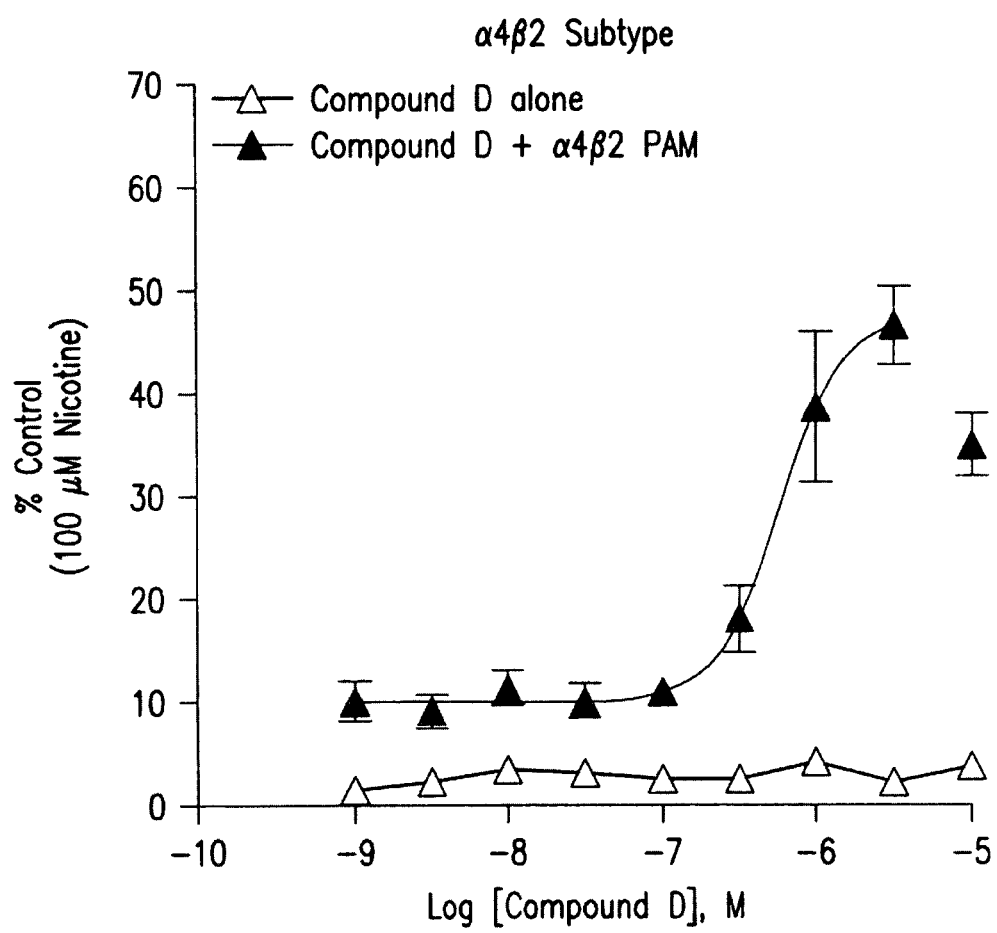
FIGS. 4A and 4B graphically represent the effect of an α4β2 positive allosteric modulator in enhancing the effect of another nAChR partial agonist (1S,5S)-3-(3,6-diaza-bicyclo[3.2.0]hept-3-yl)-quinoline (Compound D; α4β2 [$^3$H] cytisine K$_i$=6 nM)). Compound D alone does not evoke a response, but when co-applied with the PAM, 3-(3-(pyridin-3-yl)-1,2,4-oxadiazol-5-yl)benzonitrile (Compound 1), evoked robust responses at α4β2 nAChRs (FIG. 4A), but not at α3β4 nAChRs (FIG. 4B). Compound D is a representative of other nicotinic partial agonists.
Figure 4B:
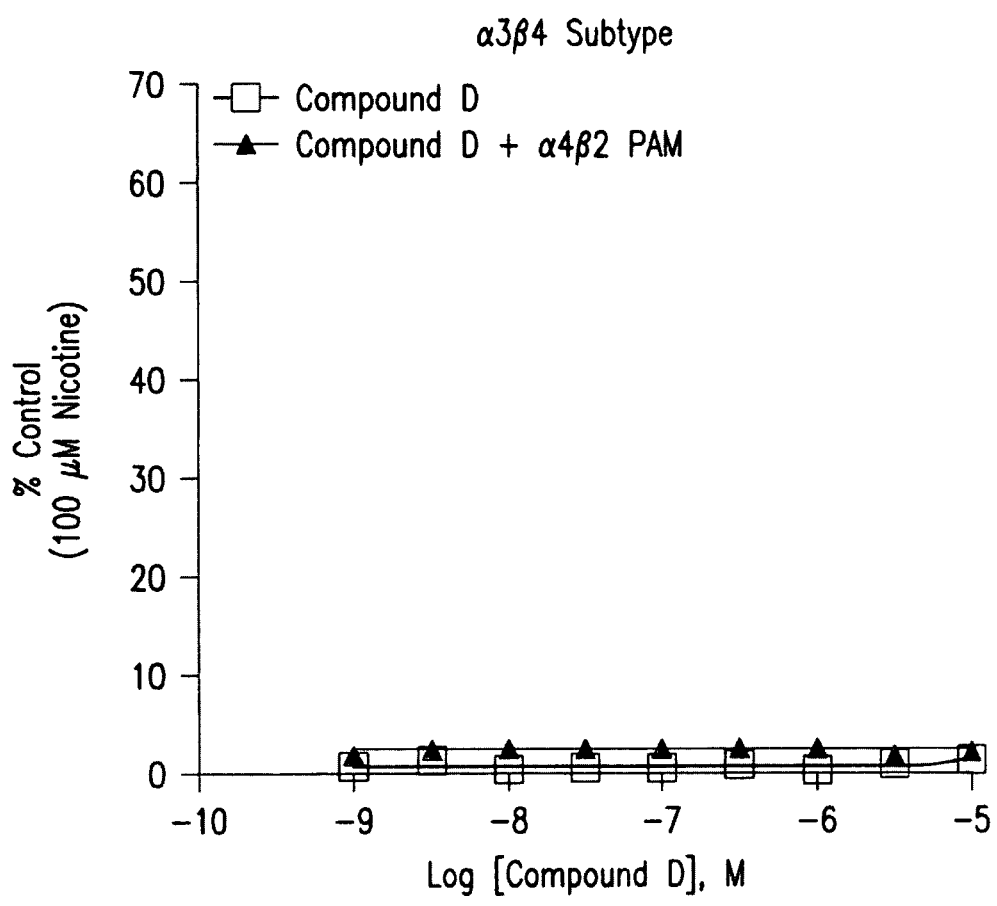

EXAMPLE B

α4β2 Positive Allosteric Modulator Enhances the Effects of Nicotinic Ligands with Very Low Intrinsic Agonist Efficacy Calcium Flux Assays: HEK-293 cells stably expressing human α4β2 or α3β4 are to confluency in 162 cm² tissue culture flasks in DMEM media supplemented with 10% FBS and 25 µg/ml zeocin and 200 µg/ml hygromycin B. IMR-32 neuroblastoma cells (ATCC) are grown to confluency in 162 cm² tissue culture flasks in minimum essential media supplemented with 10% FBS and 1 mM sodium pyruvate, 1% non-essential amino acids and 1% antibiotic-antimycotic. The cells are then dissociated using cell dissociation buffer and 100-150 µl per well of 3.5×10⁵ cells/ml cell suspension (~50,000-100,000 cells/well) was plated into 96-well black plates (poly-D-lysine precoated) with clear bottom and maintained for 24-48 hours in a tissue culture incubator at 37° C. under an atmosphere of 5% $CO_2$: 95% air. Other clonal cell lines or dissociated primary cortical neurons that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM $CaCl_2$ containing 10 mM HEPES. The stock solution was diluted 1:20 using the same buffer before use. The growth media was removed from the cells. The cells were loaded with 100 µl of the dye per well and incubated at room temperature for up to one hour for HEK 293 clonal stable cell lines or 30 minutes-45 minutes at 37° C. for IMR-32 cells. Fluorescence measurements were read simultaneously from all the wells by a Fluorometric Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 μl and incubated for five minutes. The fluorescence intensity was captured every second for the first 1 minute followed by every 5 seconds for an additional 4 minutes. This procedure was followed by 50 μl of 4× concentration of agonist and readings were taken for a period of 3-5 minutes as described above. Data was normalized to maximal responses and plotted as a function of concentration. The concentration dependence of changes fluorescence responses was fitted by nonlinear regression analysis (GraphPad Prism, San Diego, Calif.) to obtain $EC_{50}$ values.

α4β2 PAMs can also enhance the efficacy of partial agonists (compounds that bind, but activate α4β2 nAChRs with low intrinsic efficacy leading to otherwise barely detectable effects on calcium responses). For example, responses to 2-methyl-3-(2-(S)-pyrrolidinylmethoxy)pyridine (Compound C) in the presence and absence of PAM is shown in FIG. 3. The results show in the presence of an α4β2 PAM (for example, 3-(3-(pyridin-3-yl)-1,2,4-oxadiazol-5-yl)benzonitrile (Compound 1)), the maximum fluorescence calcium signal was substantially enhanced to application of 2-methyl-3-(2-(S)-pyrrolidinylmethoxy)pyridine at the α4β2 receptor (FIG. 3A), but again, not at the α3β4 receptor (FIG. 3B). Another example is provided by Compound D, (1S,5S)-3-(3,6-diaza-bicyclo[3.2.0]hept-3-yl)-quinoline; compound with toluene-4-sulfonic acid which also binds to α4β2 nAChR ([$^3$H]cyt Ki=6 nM), but does not show substantial calcium responses alone; however, when co-incubated with α4β2 PAM, responses are substantially enhanced at α4β2 nAChR (FIG. 4A), but not at α3β4 nAChRs (FIG. 4B). These observations provides mechanistic support for compounds like 2-methyl-3-(2-(S)-pyrrolidinylmethoxy)pyridine and (1S, 5S)-3-(3,6-Diaza-bicyclo[3.2.0]hept-3-yl)-quinoline being more effective when co-applied with the PAM. The potentiation of α4β2 effects by PAM may potential for optimizing and enhancing efficacy in indications such as ADHD, cognitive deficits, Alzheimer's disease, and pain.

Figure 5:
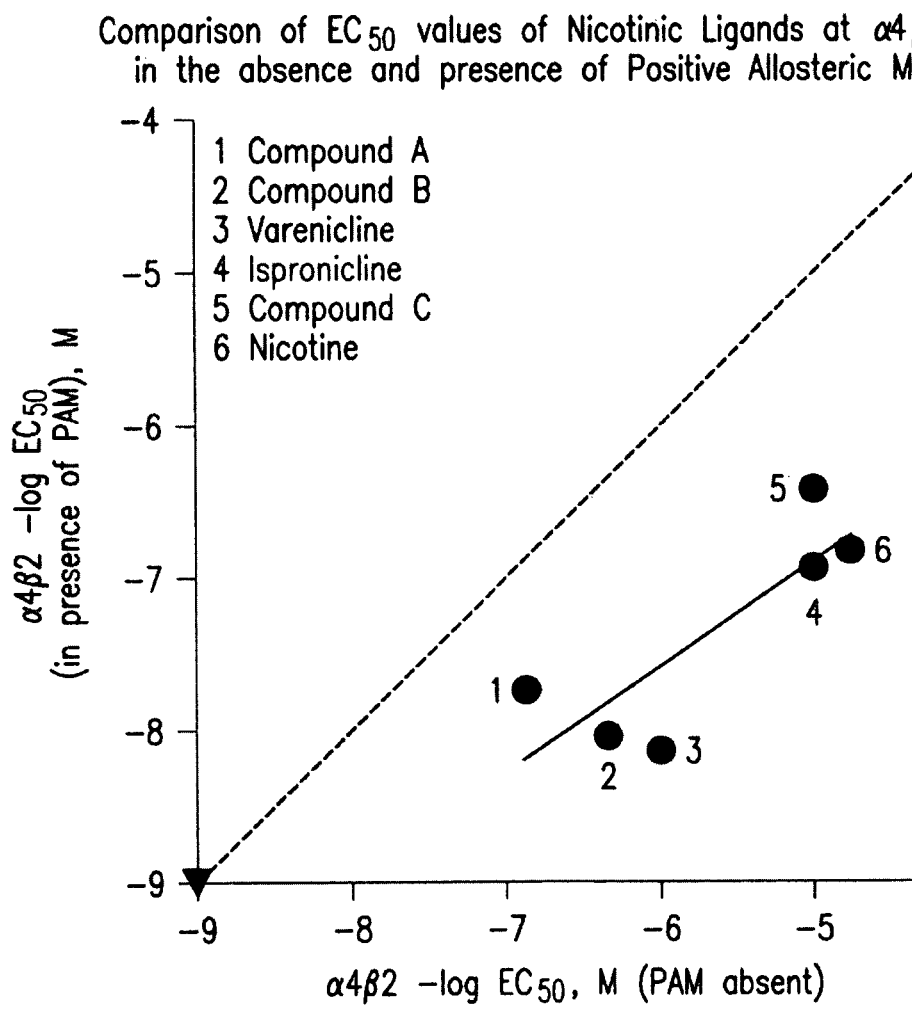
FIG. 5 shows correlation of potencies for activation of α4β2 nAChRs by various nicotinic acetylcholine receptor ligands in the presence and absence of an α4β2 PAM, 3-(3-(pyridin-3-yl)-1,2,4-oxadiazol-5-yl)benzonitrile (Compound 1). In general, these nicotinic ligands are found to be more potent in activating α4β2 nAChRs in the presence of α4β2 PAM (Compound 1).

FIG. 5 shows a comparison of $EC_{50}$ values from calcium fluorescence (FLIPR) assays using α4β2 nAChRs of several nicotinic agonists including varenicline and ispronicline in the presence and absence of positive allosteric modulator. The potency ($EC_{50}$ values) of the nicotinic agonists increase in the presence of the positive allosteric modulator.

EXAMPLE C

α4β2 PAM Enhances the Efficacy of Compound A in an In Vivo Model of Neuropathic Pain To assess whether α4β2 PAM can increase antinociceptive responses of agonists in vivo, the following study was conducted. The materials and methods used to accomplish the study follow.

Animals: Male Sprague-Dawley rats (Charles River, Wilmington, Mass.) weighing 120-150 grams at time of surgery were utilized. These animals were group housed in AAALAC approved facilities at Abbott Laboratories in a temperature-regulated environment with lights on between 0700 and 2000 hours. Food and water was available ad libitum except during testing. All animal handling and experimental protocols were approved by an institutional animal care and use committee (IACUC). All experiments were performed during the light cycle.

Chemicals: 5-[(2R)-Azetidin-2-ylmethoxy]-2-chloropyridine (Compound A, 1-100 nmol/kg) and 3-(3-pyridin-3-yl)-1,2,4-oxadiazol-5-yl)benzonitrile (α4β2 PAM Compound 1, 1-35 μmol/kg, i.p.) was used. Compound A and D was prepared in saline and injected in solution in a volume of 2 ml/kg body weight 30 minutes before behavioral evaluation. Compound 1,3-(3-(pyridin-3-yl)-1,2,4-oxadiazol-5-yl)benzonitrile, was prepared in 30% hydroxybetacyclodextrin and injected in solution in a volume of 4 ml/kg body weight immediately before Compound A. For studies with Compound D, the doses tested ranged from 0.3-30 μmol/kg i.p.

Experimental Procedure: To produce neuropathic pain, tight ligation of the L5-L6 spinal nerves was performed. As previously described in detail by Kim and Chung (Kim S H and Chung J M (1992), Pain 50: 355), following sterilization procedures, a 1.5 cm incision was made dorsal to the lumbosacral plexus. The paraspinal muscles (left side) were separated from the spinous processes, the L5 and L6 spinal nerves isolated, and tightly ligated with 3-0 silk thread. Following hemostasis, the wound was sutured and coated with antibiotic ointment. The rats were allowed to recover and then placed in a cage with soft bedding for 7-14 days before behavioral testing for mechanical allodynia.

Tactile allodynia was measured using calibrated (force; g) von Frey filaments (Stoelting, Wood Dale, Ill.). Briefly, rats were placed into individual plexiglass containers and allowed to acclimate for 15-20 minutes before testing. Withdrawal threshold was determined by increasing and decreasing stimulus intensity and estimated using a Dixon non-parametric test (Chaplan et al., 1994; Chaplan S R, Bach F W, Pogrel J W, Chung J M and Yaksh T L (1994) J Neurosci Methods 53:55-63). Only rats with threshold scores ≦4.5 g were considered allodynic and utilized in further testing. A percent of maximal possible effect (% M.P.E.) of the tested compounds was calculated according to the formula: ([post-drug threshold]−[baseline threshold])/([maximum threshold]−[baseline threshold])×100%, where maximum threshold was equal to 15 g.

Statistical analysis: Analysis of the in vivo data was carried out using analysis of variance. Where appropriate, Bonferroni's Multiple Comparison Test was used for post-hoc analysis. The level of significance was set at p less than 0.05. Data are presented as mean ±S.E.M.

Figure 6A:
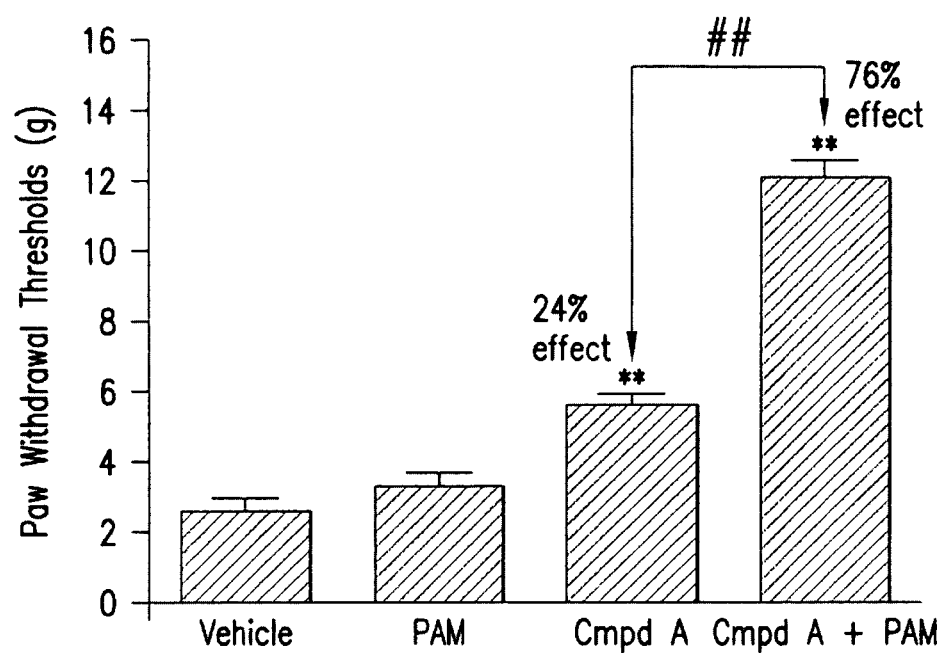
FIG. 6A graphically represents the effect of an α4β2 PAM, 3-(3-(pyridin-3-yl)-1,2,4-oxadiazol-5-yl)benzonitrile (Compound 1), on enhancing the efficacy by 5-[(2R)-azetidin-2-ylmethoxy]-2-chloropyridine (Compound A) in reversing neuropathic pain.

Results: As shown in FIG. 6A, tight ligation of L5-L6 spinal nerves induced pronounced mechanical allodynia with a decrease in mechanical paw withdrawal threshold (PWT) in the vehicle group to 2.6±0.4 g. Compound 1,3-(3-(pyridin-3-yl)-1,2,4-oxadiazol-5-yl)benzonitrile (PAM, 10 mg/kg, i.p.) did not produce significant reversal of nerve injury induced mechanical allodynia (PWT: 3.3±0.4 g, P greater than 0.05 vs. vehicle group). Compound A (0.03 μmol/kg, i.p.) produced weak but significant reversal of mechanical allodynia (PWT: 5.6±0.3 g, P less than 0.001 vs. vehicle group). When co-administered, Compound A+3-(3-(pyridin-3-yl)-1,2,4-oxadiazol-5-yl)benzonitrile (Compound 1, PAM) produced a pronounced reversal of nerve injury-induced mechanical allodynia (PWT: 12.1±0.5 g) that was significantly different from vehicle (P less than 0.001), but also from Compound A alone (P less than 0.001) and 3-(3-(pyridin-3-yl)-1,2,4-oxadiazol-5-yl)benzonitrile, Compound 1, alone (P less than 0.001). This study demonstrates that the co-administration of a α4β2 positive allosteric modulator to a α4β2 agonist potentiate the antiallodynic effects of the agonist. Since the efficacy of the α4β2 ligand in neuropathic pain is robustly improved in presence of a PAM, an overall improvement in therapeutic window for the treatment of pain may be envisaged utilizing a combination approach (agonist in combination with the α4β2 PAM).

Figure 6B:
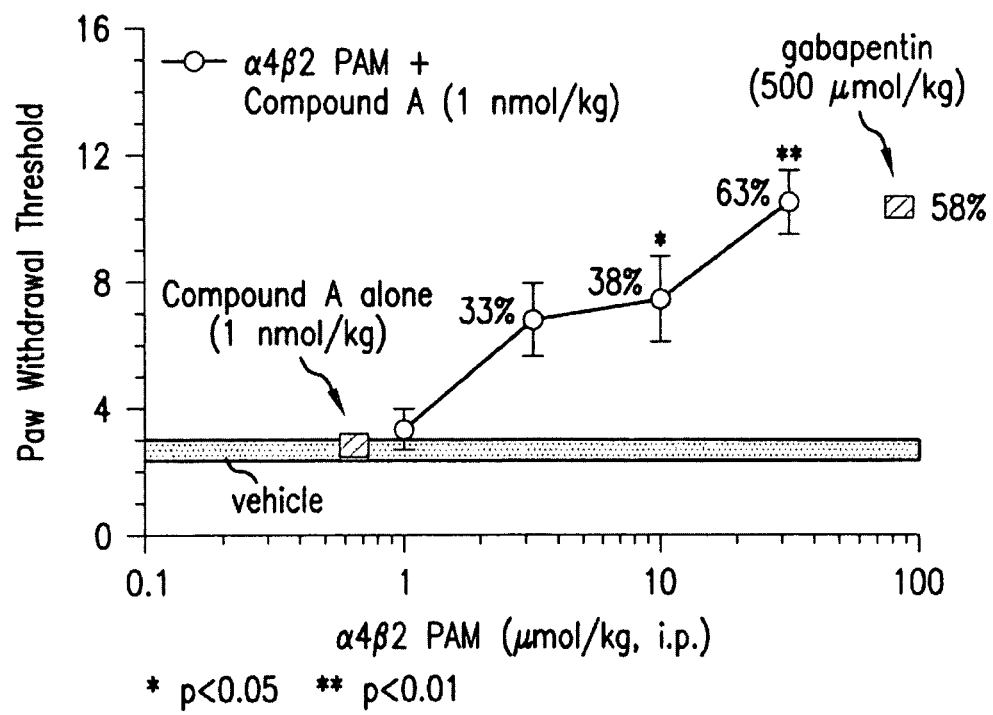
FIG. 6B graphically represents the dose dependent effect of an α4β2 PAM, 3-(3-(pyridin-3-yl)-1,2,4-oxadiazol-5-yl)benzonitrile (Compound 1), on enhancing the neuropathic pain efficacy of 5-[(2R)-azetidin-2-ylmethoxy]-2-chloropyridine (Compound A). An ineffective dose of Compound A (1 nmol/kg) demonstrates effect when combined with various doses of α4β2 PAM (Compound 1).

FIG. 6B shows that the effects of PAM (3-(3-(pyridin-3-yl)-1,2,4-oxadiazol-5-yl)benzonitrile, Compound 1) are dose-dependent. An ineffective dose of Compound A (1 nmol/kg), when combined with varying doses of PAM (3-(3-

(pyridin-3-yl)-1,2,4-oxadiazol-5-yl)benzonitrile, Compound 1) results in dose-dependent increase in efficacy, approaching at least that of gabapentin, a drug clinically used for the treatment of neuropathic pain.

Figure 7A:
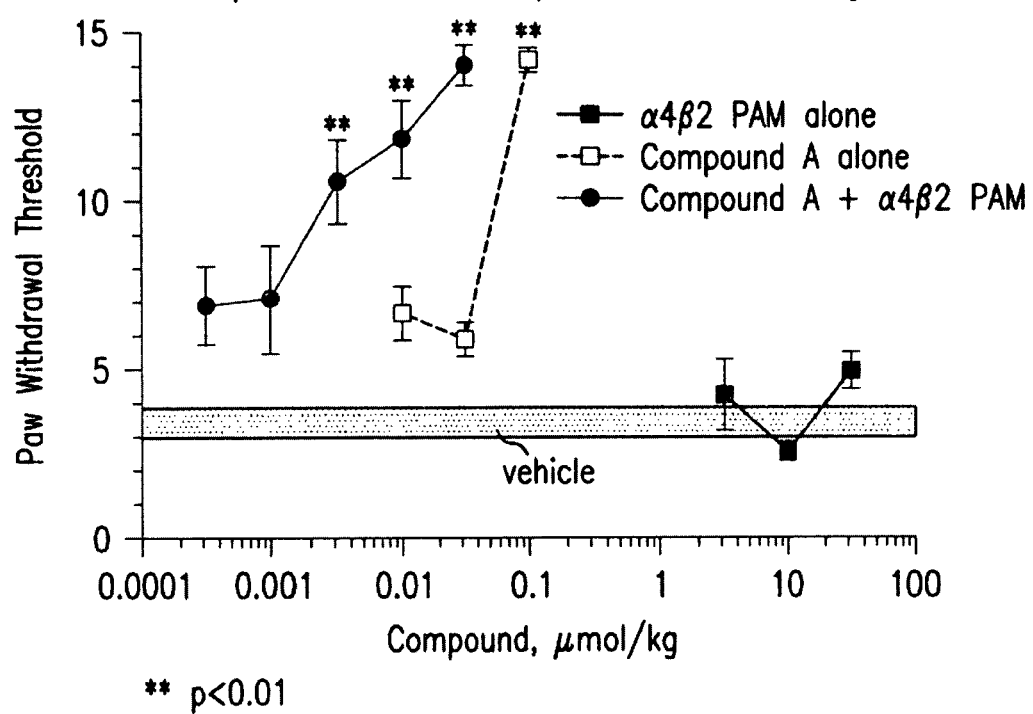
FIG. 7A shows dose-dependent effects in neuropathic pain of 5-[(2R)-azetidin-2-ylmethoxy]-2-chloropyridine (Compound A) alone, α4β2 PAM, 3-(3-pyridin-3-yl)-1,2,4-oxadiazol-5-yl)benzonitrile (Compound 1), alone and a combination of Compound 1 (3.5 µmol/kg) with various doses of Compound A. An α4β2 PAM (Compound 1) alone is ineffective. However, in the presence of Compound 1 the dose response curve of Compound A in the Chung model of neuropathic pain shifts to the left.

FIG. 7A shows dose dependent effects in neuropathic pain of 5-[(2R)-azetidin-2-ylmethoxy]-2-chloropyridine (Compound A) alone, α4β2 PAM (3-(3-(pyridin-3-yl)-1,2,4-oxadiazol-5-yl)benzonitrile, Compound 1) alone and a combination of Compound 1 (3.5 µmol/kg) with various doses of Compound A. α4β2 PAM (Compound 1) alone is ineffective, but is capable of left-shifting the dose response curve of Compound A in the Chung model of neuropathic pain.

EXAMPLE D

Analysis of Compound Effects on Emesis in Ferrets

Fasted male ferrets (Marshall BioResources, North Rose, N.Y.) weighing between 1.0 and 1.7 kg are used to determine the emetic effects. α4β2 PAM (Compound 1) was administered first and thirty minutes later, Compound A was administered at various doses. After dosing, the animals were observed for emesis and behaviors characteristic of nausea for a period of 90 minutes. The percentage of animals that experienced emesis at a given dose was recorded.

Figure 7B:
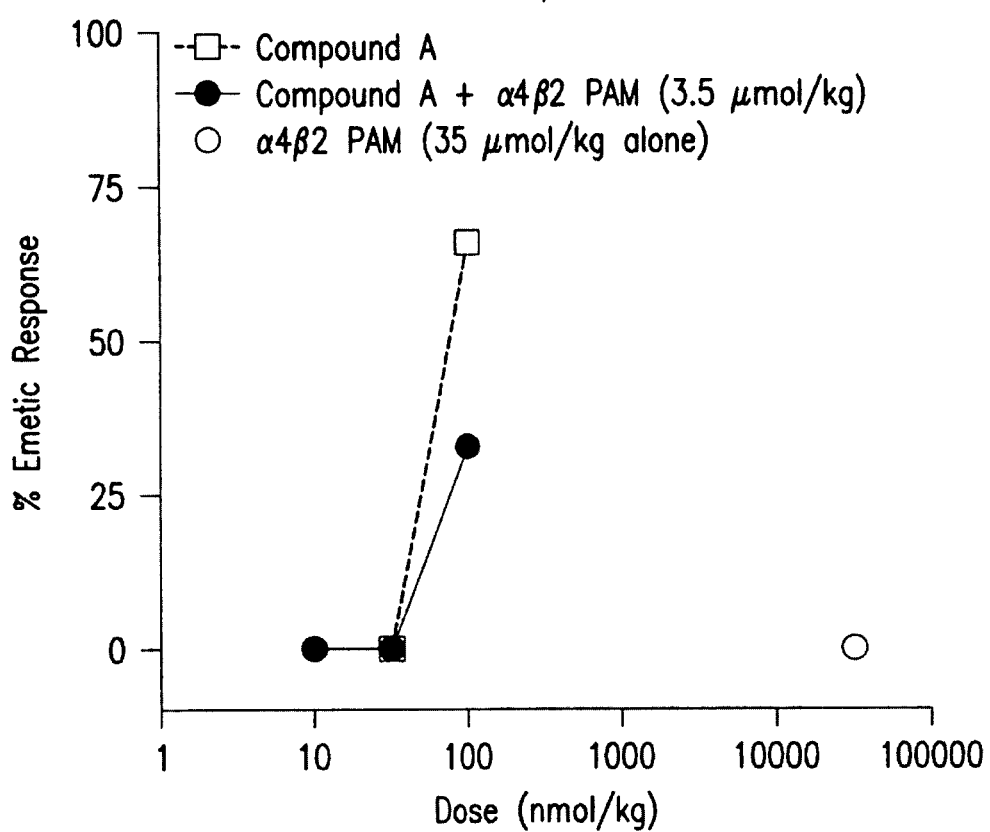
FIG. 7B shows the effects on emesis in ferrets. The effects of 5-[(2R)-azetidin-2-ylmethoxy]-2-chloropyridine (Compound A) alone, α4β2 PAM, 3-(3-(pyridin-3-yl)-1,2,4-oxadiazol-5-yl)benzonitrile (Compound 1), alone and a combination of Compound 1 (3.5 µmol/kg) with various doses of Compound A are shown. An α4β2 PAM (Compound 1) alone does not cause emesis, and does not shift the dose response curve of Compound A in the ferret model of emesis.

FIG. 7B shows effects on emesis. Shown are effects of 5-[(2R)-azetidin-2-ylmethoxy]-2-chloropyridine (Compound A) alone, α4β2 PAM (Compound 1) alone and a combination of Compound 1 (3.5 µmol/kg) with various doses of compound A. α4β2 PAM (Compound 1) alone does not cause emesis, and does not shift the dose response curve of Compound A in the ferret model of emesis.

Figure 8A:
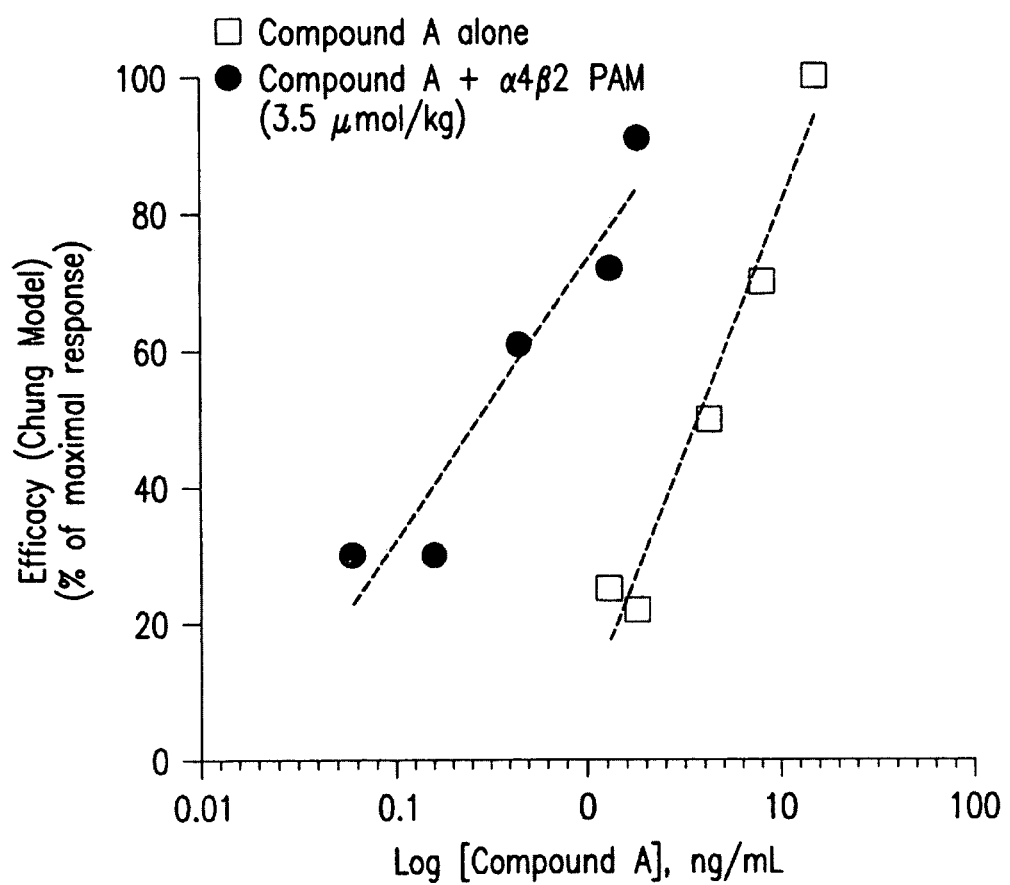
FIGS. 8A and 8B show plasma level analysis in models of neuropathic pain and emesis. The efficacy of Compound A is shifted left-ward as shown in FIG. 8A, but no shift in effects on emesis are shown in FIG. 8B. The maximal efficacy of Compound A can be realized in neuropathic pain without incidence of emesis, in presence of α4β2 PAM, 3-(3-(pyridin-3-yl)-1,2,4-oxadiazol-5-yl)benzonitrile (Compound 1). The data demonstrates that the therapeutic window of α4β2 nAChR agonists is wider in the presence of α4β2 PAM.
Figure 8B:
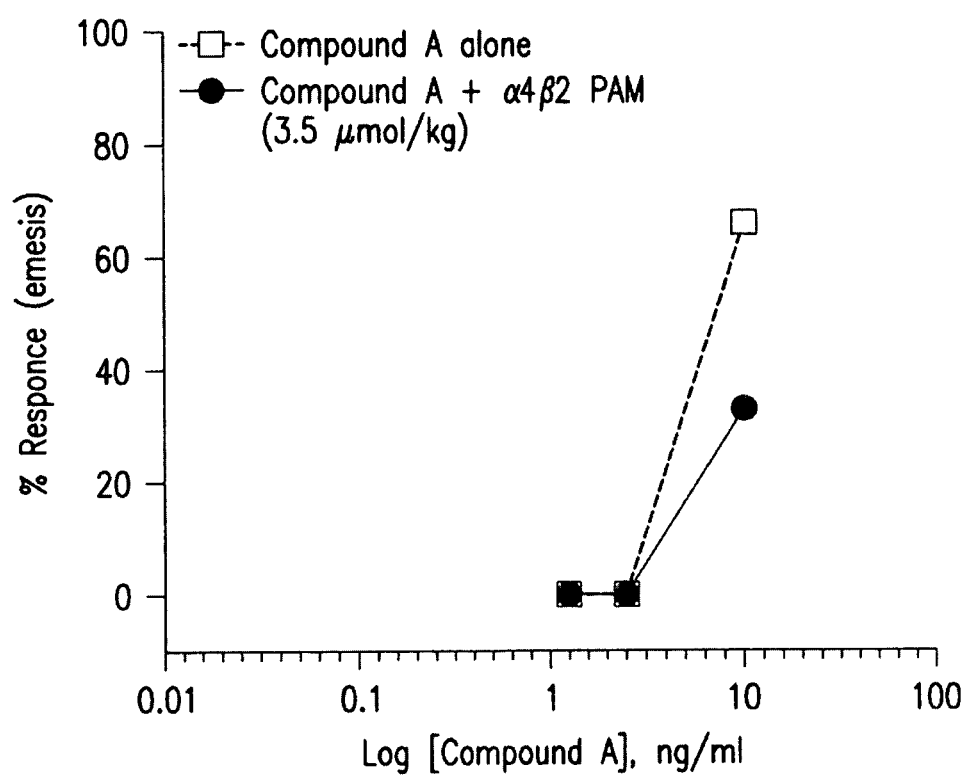

FIGS. 8A and 8B show plasma level analysis in models of neuropathic pain and emesis. Note the left ward shift in efficacy of Compound A in FIG. 8A, but no shift in effects on emesis in FIG. 8B. In other words, maximal efficacy of Compound A can be realized in neuropathic pain without incidence of emesis, in presence of α4β2 PAM (Compound 1), thus widening the therapeutic window of α4β2 nAChR agonists

Figure 9:
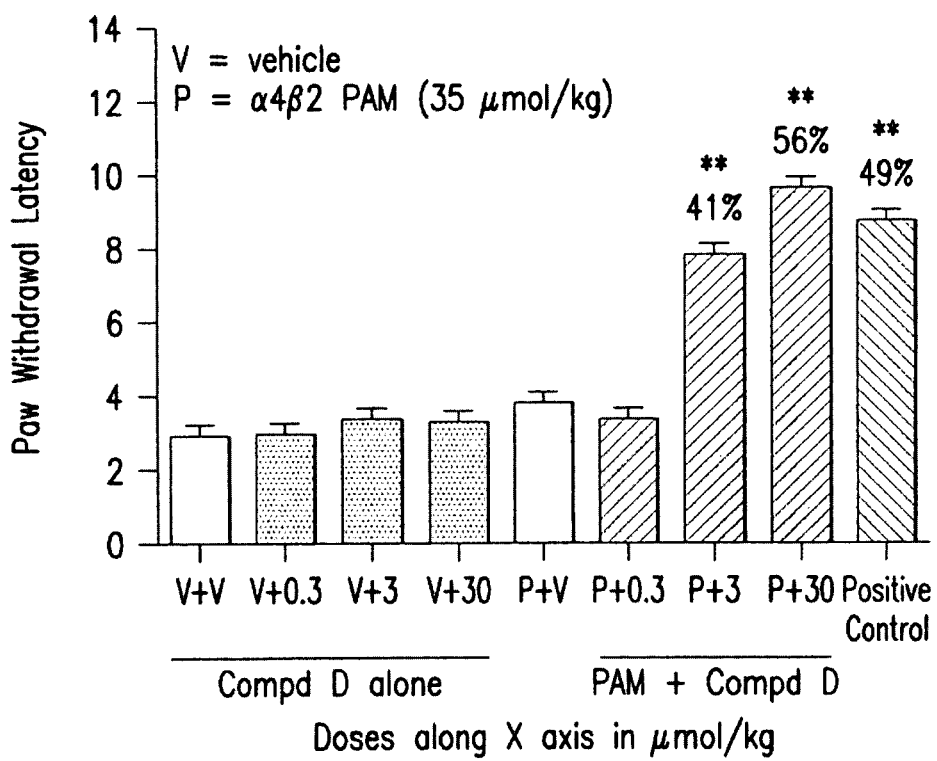
FIG. 9 shows the efficacy of a partial agonist, Compound D, in the presence and absence of α4β2 PAM, 3-(3-(pyridin-3-yl)-1,2,4-oxadiazol-5-yl)benzonitrile (Compound 1). In the example illustrated, Compound D when administered alone is ineffective in relieving pain. When co-dosed with α4β2 PAM (Compound 1), Compound D demonstrates effect, and the data demonstrate that Compound D provides significant relief of neuropathic pain in rats.

EXAMPLE E

α4β2 Partial Agonists can be Effective in Reversing Neuropathic Pain in the Presence of α4β2 Positive Allosteric Modulators To further examine effects in neuropathic pain, the effects of Compound D, another α4β2 ligand with low intrinsic efficacy (partial agonist) was examined in the Chung model. Alone, Compound D is ineffective in reversing neuropathic pain, but when combined with the PAM (Compound 1), significant efficacy can be realized. FIG. 9 shows the efficacy of partial agonist, Compound D in the presence and absence of α4β2 PAM (Compound 1). Compound D when administered alone is ineffective in relieving pain. When co-dosed with α4β2 PAM (Compound 1), Compound D is now effective, and shows significant relief of neuropathic pain in rats. As shown previously, PAM (Compound 1) alone is ineffective (P+V).

Characterization of Nicotinic Acetylcholine Receptor Ligands

In addition to the assays previously described for assessing nicotinic acetylcholine receptor positive allosteric modulators (fluorescence-based measurements, electrophysiology measurements using *Xenopus* oocytes or cell lines), the receptor interactions of positive allosteric modulators at α4β2 nAChRs also can be evaluated according to the [$^3$H]-POB binding assay, which was performed as described below.

[$^3$H]-3-(5-(Pyridin-3-yl)-1,2,4-oxadiazol-3-yl)benzonitrile ([$^3$H]-POB) Binding

Figure 10:
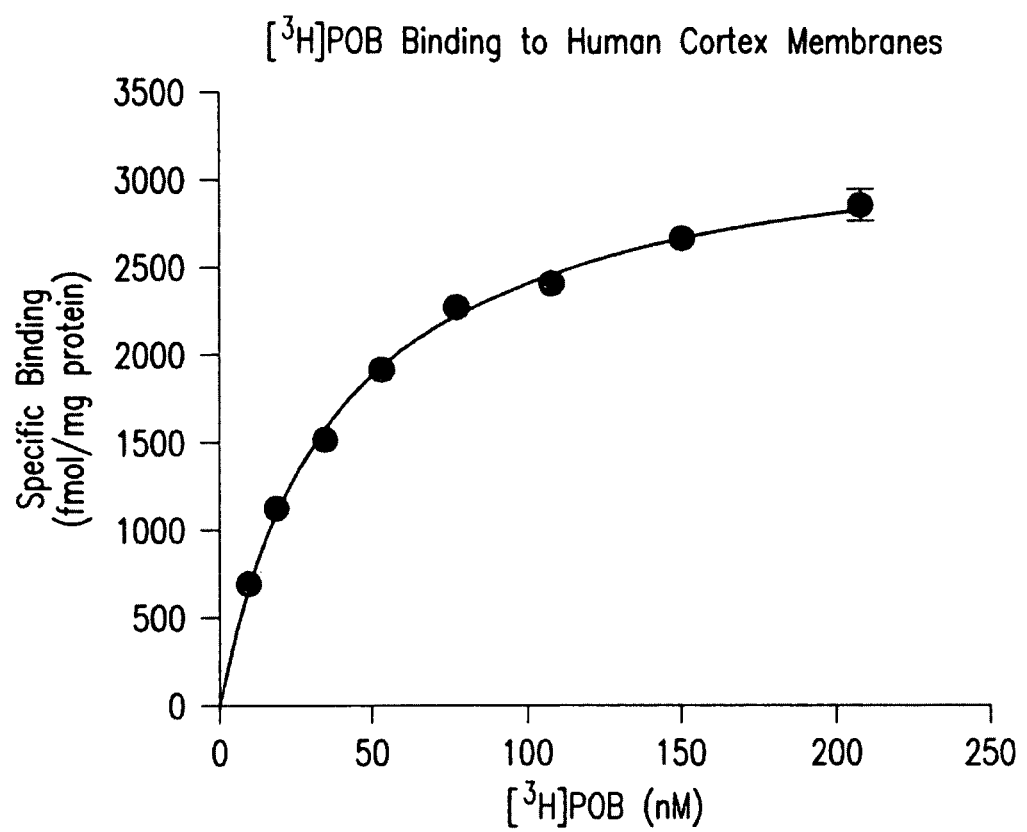
FIG. 10 is a graphical representation of specific binding to receptor sites in human brain membranes (fmoles per mg protein) as a function of the concentration of a radioligand [$^3$H]-3-(5-(pyridin-3-yl)-1,2,4-oxadiazol-3-yl)benzonitrile ([$^3$H]-POB, nM).

[$^3$H]-POB ([$^3$H]-3-(5-(pyridin-3-yl)-1,2,4-oxadiazol-3-yl)benzonitrile) binding to a α4β2 nAChR modulator site was determined using membrane enriched fractions from human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). For saturation binding isotherms, eight concentrations of [$^3$H]-POB (10-250 nM) in quadruplicate and homogenate containing 100-200 µg of protein were incubated in a final volume of 500 µL for 75 minutes at 4° C. Non-specific binding was determined in the presence of 30 µM unlabeled 3-(5-(pyridin-3-yl)-1,2,4-oxadiazol-3-yl)benzonitrile. Under these conditions, saturable binding of [$^3$H]-POB binding was measured in membrane enriched fractions from human frontal cortex (FIG. 10). The K$_d$ and B$_{max}$ values were 60±16 nM and 2900±500 fmol/mg protein, respectively. Membrane preparations from other species (rat, mouse, ferret) and from clonal or transfected cell lines that express α4β2 nAChRs cloned from various species may also be used in this binding assay.

For use in concentration-inhibition assays, seven log-dilution concentrations of test compounds containing 100-200 µg of protein, and 50 nM [$^3$H]-POB (16.4 Ci/mmol) were incubated in a final volume of 500 µL for 75 minutes at 4° C. in duplicate. Non-specific binding was determined in the presence of 30 µM 3-(5-(pyridin-3-yl)-1,2,4-oxadiazol-3-yl)benzonitrile. Bound radioactivity was collected on Millipore MultiScreen® harvest plates FB presoaked with 0.3% polyethyleneimine using a PerkinElmer cell harvester, washed with 2.5 mL of ice-cold buffer, and radioactivity was determined using a PerkinElmer TopCount Microplate beta counter. Dissociation constant (K$_d$) and maximum binding (B$_{max}$) values from saturation binding experiments were determined using GraphPad Prism (Graphpad Software, San Diego, Calif.). IC$_{50}$ values were determined by nonlinear regression in Microsoft® Excel or Assay Explorer. K$_i$ values were calculated from the IC$_{50}$s using the Cheng-Prusoff equation, where K$_i$=IC$_{50}$/(1+[Ligand]/K$_D$]).

[$^3$H]-POB was obtained according to the preparation procedures generally described in Example 135 shown below.

EXAMPLE 135

[$^3$H]-3-(5-(pyridin-3-yl)-1,2,4-oxadiazol-3-yl)benzonitrile

EXAMPLE 135A 3-(5-(5-bromopyridin-3-yl)-1,2,4-oxadiazol-3-yl)benzonitrile

The title compound was prepared according to the procedure of Example 4B using 3-cyano-N'-hydroxybenzimidamide and 5-bromonicotinoyl chloride (Alfa). $^1$H NMR (300 MHz, DMSO-d$_6$) δ 7.67 (m, 1 H), 7.74 (m, 1 H), 8.41 (m, 1 H), 8.49 (m, 1 H), 8.64 (s, 1 H), 8.93 (s, 1 H), 9.4 (s, 1 H) ppm; MS (DCI/NH$_3$) m/z 327 (M+H)$^+$.

EXAMPLE 135B

[$^3$H]-3-(5-(pyridin-3-yl)-1,2,4-oxadiazol-3-yl)benzonitrile ([$^3$H]-POB)

The compound of Example 135A was dissolved in a mixture of dichloromethane, triethylamine, and 5% palladium on carbon. The reaction solution was then saturated with tritium gas (1.2 Ci). The reaction mixture was stirred at room temperature for 3.5 hours, the catalyst was removed by filtration, ant the filtrate was concentrated to yield crude tritiated product. Further purification of the crude material by reverse-phase HPLC using a 30 minute 40% isocratic acetonitrile run (column LunaC18, 254 nm) to provide a total of 200 mCi (1 mL, methanol).

The radiochemical purity of [$^3$H]-POB was found to be 99% and the specific activity was determined to be 16.4 Ci/mmol.

Nicotinic acetylcholine receptor ligands suitable for the invention exhibit $K_i$ values ranging about 1 nanomolar to about 10 micromolar when tested by the [$^3$H]-POB assay, many having a $K_i$ of less than 5 micromolar. Compounds that modulate the function of α4β2 nAChRs by altering the activity of the receptor or signaling are suitable for the composition. More specifically, the compounds that function as allosteric modulators enhancing the efficacy and/or potency of acetylcholine or a nicotinic agonist are desired. Multiple binding sites at α4β2 nAChRs may exist for such compounds, of which only one site may be defined by [$^3$H]POB binding.

Also contemplated is compound of formula (II*):

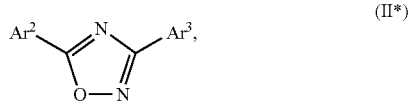

(II*)

wherein $Ar^2$ is aryl or heteroaryl, wherein the aryl or heteroaryl is substituted or unsubstituted, and, when substituted, the aryl or heteroaryl is substituted with 1, 2, 3, or 4 substituents selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_4$-$C_{10}$ heterocycle, $C_1$-$C_6$ alkyl, —($C_1$-$C_6$ alkyl)NHC(O)O—($C_1$-$C_6$ alkyl), $C_1$-$C_6$ hydroxyalkyl, $C_1$-$C_6$ alkylcarbonyl, amino, hydroxyl, haloalkyl-C(O)—, haloalkyl-$SO_2$—, alkyl-$SO_2$—, —$SO_2NH_2$, —$SO_2NH(C_1$-$C_6$ alkyl), —$SO_2N(C_1$-$C_6$ alkyl)$_2$, cyano, nitro, $C_1$-$C_6$ acylamino, $C_1$-$C_6$ alkoxy, —C(O)NH$_2$, —C(O)O—($C_1$-$C_6$ alkyl), and carboxy; and $Ar^3$ is aryl or heteroaryl, wherein the aryl or heteroaryl is substituted or unsubstituted, and, when substituted, the aryl or heteroaryl is substituted with a substituent selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_1$-$C_6$ alkyl, $C_1$-$C_6$ hydroxyalkyl, amino, hydroxyl, haloalkyl-$SO_2$—, cyano, nitro, $C_1$-$C_6$ acylamino, $C_1$-$C_6$ alkoxy, —N($C_1$-$C_6$ alkyl)$_2$, and carboxy; wherein at least one of the available atoms within a compound of formula (II*) is replaced with a radio-isotope. A particular radiolabelled compound of formula (II*) is [$^3$H]-3-(5-(pyridin-3-yl)-1,2,4-oxadiazol-3-yl)benzonitrile. Such compounds are suitable for use in determining the binding affinity of nicotinic acetylcholine receptor subtype α4β2 positive allosteric modulators.

Another embodiment of the invention is a radiolabeled compound of formula (II*), wherein $Ar^2$ and $Ar^3$ are independently phenyl, pyrazinyl, pyridinyl, pyrimidinyl, pyridazine, triazinyl, or a bicyclic heteroaryl, substituted independently with 0, 1, 2, 3, or 4 substitutents selected from the group consisting of alkoxy, alkoxycarbonyl, alkoxycarbonylamino, alkoxycarbonylaminoalkyl, alkyl, alkylamino, alkylcarbonyl, alkylsulfonyl, amido, amino, aminoalkyl, carboxy, dialkylamino, dialkylaminoalkyl, halo, haloalkyl, haloalkylcarbonyl, heteroaryl, heterocycle, hydroxy, hydroxyalkyl, cyano, nitro, sulfonamide and dialkylsulfonylformimidamide; provided that when one of $Ar^2$ and $Ar^3$ is pyridinyl or aryl, the other is not pyridinyl; when $Ar^3$ is pyridinyl, $Ar^2$ is not pyrazinyl.

It is understood that the foregoing detailed description and accompanying examples are merely illustrative and are not to be taken as limitations upon the scope of the invention, which is defined solely by the appended claims and their equivalents. The compositions, methods, and articles of manufacture have been described with reference to various specific embodiments and techniques. However, various changes and modifications, including without limitation those relating to the compounds, substituents, syntheses, and/or methods of use of the invention, may be made without departing from the spirit and scope thereof. The examples described herein are intended only to illustrate and do not limit the scope of the invention as defined in the appended claims and equivalents thereof.

What is claimed is:

1. A compound of formula (II):

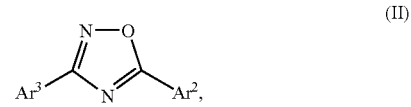

(II)

wherein $Ar^2$ is bicyclic heteroaryl selected from the group consisting of azaindolyl, benzimidazolyl, benzo[d][1,3]dioxolyl, benzofuranyl, benzoxadiazolyl, benzo[d]imidazolyl, benzo[d]imidazole-2(3H)-thione, benzoisoxazole, benzoisothiazole, benzooxazole, benzooxazolone, benzo[d][1,2,3]thiadiazolyl, 1,3-benzothiazolyl, benzothiophenyl, benzo[d][1,2,3]triazolyl, 2,2-difluorobenzo[d][1,3]dioxolyl, furopyridine, imidazopyridinyl, indolyl, indazolyl, isobenzofuran, isoindolyl, oxazolopyridine, pyrazolopyrimidinyl, pyrrolopyridinyl, thienopyridinyl, and [1,2,4]triazolopyridinyl; and $Ar^3$ is independently pyrazinyl, pyridazinyl, pyridinyl, pyrimidinyl, or triazinyl, substituted independently with 0, 1, 2, 3, or 4 substituents selected from the group consisting of alkoxy, alkoxycarbonyl, alkoxycarbonylamino, alkoxycarbonylaminoalkyl, alkyl, alkylamino, alkylcarbonyl, alkylsulfonyl, amido, amino, aminoalkyl, carboxy, dialkylamino, dialkylaminoalkyl, halo, haloalkyl, haloalkylcarbonyl, heteroaryl, heterocycle, hydroxy, hydroxyalkyl, cyano, nitro, oxo, sulfonamide and dialkylsulfonylformimidamide;

or a pharmaceutically acceptable salt thereof.

2. The compound of claim 1 or a pharmaceutically acceptable salt thereof, wherein $Ar^3$ is pyrimidinyl or pyridazinyl.

3. The compound of claim 1 or a pharmaceutically acceptable salt thereof, wherein $Ar^3$ is independently pyridazinyl, pyridinyl, or pyrimidinyl.

4. The compound of claim 1, selected from the group consisting of
  5-(imidazo[1,5-a]pyridin-6-yl)-3-(pyridin-3-yl)-1,2,4-oxadiazole;
  5-(1H-indol-6-yl)-3-(pyridin-3-yl)-1,2,4-oxadiazole;
  5-(2,7-dimethylpyrazolo[1,5-a]pyrimidin-6-yl)-3-(pyridin-3-yl)-1,2,4-oxadiazole;
  5-(2,2-difluorobenzo[d][1,3]dioxol-5-yl)-3-(pyridin-3-yl)-1,2,4-oxadiazole;
  5-(2-methylbenzofuran-5-yl)-3-(pyridin-3-yl)-1,2,4-oxadiazole;

5-(benzo[d][1,2,3]thiadiazol-5-yl)-3-(pyridin-3-yl)-1,2,4-oxadiazole;
5-(1H-benzo[d]imidazol-5-yl)-3-(pyridin-3-yl)-1,2,4-oxadiazole;
5-(1H-benzo[d][1,2,3]triazol-5-yl)-3-(pyridin-3-yl)-1,2,4-oxadiazole;
5-(benzo[d]thiazol-5-yl)-3-(pyridin-3-yl)-1,2,4-oxadiazole;
3-(pyridin-3-yl)-5-(1H-pyrrolo[2,3-b]pyridin-5-yl)-1,2,4-oxadiazole;
5-(1H-indol-5-yl)-3-(pyridin-3-yl)-1,2,4-oxadiazole;
5-(benzofuran-5-yl)-3-(pyridin-3-yl)-1,2,4-oxadiazole;
5-(1-methyl-1H-benzo[d]imidazol-5-yl)-3-(pyridin-3-yl)-1,2,4-oxadiazole;
5-(1H-indazol-5-yl)-3-(pyridin-3-yl)-1,2,4-oxadiazole;
5-([1,2,4]triazolo[4,3-a]pyridin-6-yl)-3-(pyridin-3-yl)-1,2,4-oxadiazole;
5-(3-(pyridin-3-yl)-1,2,4-oxadiazol-5-yl)benzo[d]oxazol-2(3H)-one;
5-(3-(pyridin-3-yl)-1,2,4-oxadiazol-5-yl)-1H-benzo[d]imidazole-2(3H)-thione;
1,3-dimethyl-5-(3-(pyridin-3-yl)-1,2,4-oxadiazol-5-yl)-1H-benzo[d]imidazol-2(3H)-one;
6-(3-(pyridin-3-yl)-1,2,4-oxadiazol-5-yl)benzo[d]oxazol-2(3H)-one;
5-(3-(pyridin-3-yl)-1,2,4-oxadiazol-5-yl)-1H-benzo[d]imidazol-2(3H)-one;
6-(3-(pyridin-3-yl)-1,2,4-oxadiazol-5-yl)benzo[d]oxazol-2-amine;
6-(3-(pyridin-3-yl)-1,2,4-oxadiazol-5-yl)benzo[d]oxazole; and
5-(benzo[d][1,3]dioxol-5-yl)-3-(pyridin-3-yl)-1,2,4-oxadiazole;

or a pharmaceutically acceptable salt thereof.

5. A pharmaceutical composition comprising a therapeutically effective amount of a compound of claim 1, or a salt thereof, and a pharmaceutically acceptable carrier or excipient.

6. The composition of claim 5, further comprising a nicotinic acetylcholine receptor ligand.

7. The composition of claim 6, wherein the nicotinic acetylcholine receptor ligand is a nicotinic acetylcholine receptor subtype α4β2 ligand demonstrating a Ki value that as measured by [3H]-cytisine binding assay (Ki Cyt) of about 0.001 nanomolar to about 100 micromolar.

8. The composition of claim 6, wherein the nicotinic acetylcholine receptor ligand is a nicotinic acetylcholine receptor subtype α4β2 agonist or partial agonist.

\* \* \* \* \*